US011865176B2

(12) United States Patent
Wong

(10) Patent No.: US 11,865,176 B2
(45) Date of Patent: Jan. 9, 2024

(54) COMPOSITIONS AND METHODS OF MODULATING ANTI-TUMOR IMMUNITY

(71) Applicant: Dana-Farber Cancer Institute, Inc., Boston, MA (US)

(72) Inventor: Kwok-Kin Wong, Arlington, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 55 days.

(21) Appl. No.: 16/347,999

(22) PCT Filed: Nov. 8, 2017

(86) PCT No.: PCT/US2017/060669
§ 371 (c)(1),
(2) Date: May 7, 2019

(87) PCT Pub. No.: WO2018/089518
PCT Pub. Date: May 17, 2018

(65) Prior Publication Data
US 2019/0328874 A1 Oct. 31, 2019

Related U.S. Application Data

(60) Provisional application No. 62/419,160, filed on Nov. 8, 2016.

(51) Int. Cl.
*A61K 39/395* (2006.01)
*C07K 16/28* (2006.01)
*A61K 31/519* (2006.01)
*A61K 31/506* (2006.01)
*A61P 35/00* (2006.01)
*A61K 39/00* (2006.01)

(52) U.S. Cl.
CPC ...... *A61K 39/39541* (2013.01); *A61K 31/506* (2013.01); *A61K 31/519* (2013.01); *A61P 35/00* (2018.01); *C07K 16/2818* (2013.01); *A61K 2039/505* (2013.01); *C07K 2317/76* (2013.01)

(58) Field of Classification Search
CPC ............ A61K 39/39541; A61K 31/506; A61K 31/519; A61K 2039/505; A61P 35/00; C07K 16/2818; C07K 2317/76
See application file for complete search history.

(56) References Cited

U.S. PATENT DOCUMENTS

| 8,598,186 B2 | 12/2013 | Tavares et al. |
| 8,598,197 B2 | 12/2013 | Tavares et al. |
| 8,691,830 B2 | 4/2014 | Tavares et al. |
| 8,822,683 B2 | 9/2014 | Tavares et al. |
| 8,829,012 B2 | 9/2014 | Tavares et al. |
| 9,102,682 B2 | 8/2015 | Tavares et al. |
| 9,260,442 B2 | 2/2016 | Tavares |

| 2007/0179118 A1 | 8/2007 | Barvian et al. |
| 2011/0224227 A1 | 9/2011 | Sharpless et al. |
| 2014/0275066 A1 | 9/2014 | Sharpless et al. |

FOREIGN PATENT DOCUMENTS

| WO | WO 2005/052147 A2 | 6/2005 | |
| WO | WO 2006/074985 A1 | 7/2006 | |
| WO | WO 2009/061345 A2 | 5/2009 | |
| WO | WO 2010/020675 A1 | 2/2010 | |
| WO | WO 2010/039997 A2 | 4/2010 | |
| WO | WO 2011/101409 A1 | 8/2011 | |
| WO | WO 2012/061156 A1 | 5/2012 | |
| WO | WO-2014193898 A1 * | 12/2014 | .......... A61K 31/506 |
| WO | WO-2015084892 A1 * | 6/2015 | ............. A61K 31/35 |
| WO | WO 2016/040858 A1 | 3/2016 | |
| WO | WO 2016/040892 A1 * | 3/2016 | .......... A61K 31/506 |
| WO | WO 2016/100882 A1 | 6/2016 | |
| WO | WO 2017/158570 A1 | 9/2017 | |
| WO | WO 2017/181073 A1 | 10/2017 | |
| WO | WO 2017/205213 A1 | 11/2017 | |

OTHER PUBLICATIONS

Sun, L., Zhang, L., Yu, J. et al. Clinical efficacy and safety of anti-PD-1/PD-L1 inhibitors for the treatment of advanced or metastatic cancer: a systematic review and meta-analysis. Sci Rep 10, 2083 (2020) (Year: 2020).*
Lewis AL, Chaft J, Girotra M, Fischer GW. Immune checkpoint inhibitors: a narrative review of considerations for the anaesthesiologist. Br J Anaesth. Mar. 2020;124(3):251-260 (Year: 2020).*
Parylo S, Vennepureddy A, Dhar V, Patibandla P, Sokoloff A. Role of cyclin-dependent kinase 4/6 inhibitors in the current and future eras of cancer treatment. Journal of Oncology Pharmacy Practice. 2019;25(1):110-129. (Year: 2019).*
Eli Lilly and Company, A Phase 1a/1b Study of a Novel Anti-PD-L1 Checkpoint Antibody (LY3300054) Administered Alone or in Combination With Other Agents in Advanced Refractory Solid Tumors (Phase 1a/1b Anti-PD-L1 Combinations in Tumors-PACT); NCT02791334; Oct. 7, 2016 (Year: 2016).*
Bisi JE, Sorrentino JA, Roberts PJ, Tavares FX, Strum JC. Preclinical Characterization of G1T28: A Novel CDK4/6 Inhibitor for Reduction of Chemotherapy-Induced Myelosuppression. Mol Cancer Ther. May 2016;15(5):783-93. doi: 10.1158/1535-7163.MCT-15-0775. Epub Jan. 29, 2016. PMID: 26826116. (Year: 2016).*
Adams, J. L. et al., "Big opportunities for small molecules in immune-oncology," Nature Reviews Drug Discovery, 14:603-622 (2015).
Akbay, E. A. et al., "Activation of the PD-1 Pathway Contributes to Immune Escape in EGFR-Driven Lung Tumors," Cancer Discov, 3(12):1355-63 (2013).
Anders, L. et al., "A Systematic Screen for CDK4/6 Substrates Links FOXM1 Phosphorylation to Senescence Suppression in Cancer Cells," Cancer Cell, 20:620-634 (2011).
Anonymous, "A Study of Anti-PD-L1 Checkpoint Antibody (LY3300054) Alone and in Combination in Participants With Advanced Refractory Solid Tumors (PACT) Full Text View—Clinical Trials. gov," Jun. 1, 2016, https://clinical trails.gov/show/NCT02791334, 9 pages.

(Continued)

*Primary Examiner* — Hong Sang
(74) *Attorney, Agent, or Firm* — Baker Donelson

(57) ABSTRACT

The present invention provides methods of treating cancer by combination therapy with CDK4/6 inhibitors and immune checkpoint inhibition.

7 Claims, 31 Drawing Sheets
Specification includes a Sequence Listing.

(56) References Cited

OTHER PUBLICATIONS

Aref, A. R. et al., "Screening therapeutic EMT blocking agents in a three-dimensional microenvironment," Integr. Biol., 5:381-389 (2013).

Asghar, U. et al., "The history and future of targeting cyclin-dependent kinases in cancer therapy," Nature Reviews Drug Discovery, 14(2):130-146 (2015).

Balkwill, F. R. & Mantovani, A., "Cancer-related inflammation: Common themes and therapeutic opportunities," Seminars in Cancer Biology, 22:33-40 (2012).

Berglund, L. M. et al., "NFAT regulates the expression of AIF-1 and IRT-1: yin and yang splice variants of neointima formation and atherosclerosis," Cardiovascular Research, 93:414-423 (2012), doi:10.1093/cvr/cvr309.

Bhattacharyya, S. et al., "NFATc1 affects mouse splenic B cell function by controlling the calcineurin-NFAT signaling network," J. Exp. Med., 208(4):823-839 (2011).

Bienkiewicz, E. A. & Lumb, K. J. et al., "Random-coil chemical shifts of phosphorylated amino acids," Journal of Biomolecular NMR, 15:203-206 (1999), doi:10.1023/A:100837502974699.

Bisi, J. E. et al., "Preclinical Characterization of G1T28: A Novel CDK4/6 Inhibitor for Reduction of Chemotherapy-Induced Myelosuppression," Molecular Cancer Therapeutics, 15:783-793 (2016).

Blomberg, K. E. M. et al., "Transcriptional signatures of Itk-deficient CD3+, CD4+ and CD8+ T-cells," BMC Genomics, 10:233 (2009), doi:10.1186/1471-2164-10-233, 19 pages.

Borghaei, H. et al., "Nivolumab versus Docetaxel in Advanced Nonsquamous Non-Small-Cell Lung Cancer," The New England Journal of Medicine, 373(17):1627-1639 (2015).

Brahmer, J. R. et al., "Phase I Study of Single-Agent Anti-Programmed Death-1 (MDX-1106) in Refractory Solid Tumors: Safety, Clinical Activity, Pharmacodynamics, and Immunologic Correlates," Journal of Clinical Oncology, 28(19):3167-3175 (2010).

Bray, N. L. et al., "Near-optimal probabilistic RNA-seq quantification," Nature Biotechnology, 34(5):525-527 (2016), and Supplementary Materials, 2 pages.

Busch, R. et al., "NFATc1 releases BCL6-dependent repression of CCR2 agonist expression in peritoneal macrophages from *Saccharomyces cerevisiae* infected mice," Eur. J. Immunol., 46:634-646 (2016), doi:10.1002/eji.201545925.

Buss, H. et al., "Cyclin-Dependent Kinase 6 Phosphorylates NF-kB P65 at Serine 536 and Contributes to the Regulation of Inflammatory Gene Expression," PLoS One, 7(12):e51847 (2012), doi:10.1371/journal.pone.0051847, 13 pages.

Cadoo, K. A. et al., "Palbociclib: an evidence-based review of its potential in the treatment of breast cancer," Breast Cancer: Targets and Therapy, 6:123-133 (2014).

Chang, J. T. et al., "Asymmetric Proteasome Segregation as a Mechanism for Unequal Partitioning of the Transcription Factor T-bet during T Lymphocyte Division," Immunity, 34:492-504 (2011).

Chen, Z. et al., "A murine lung cancer co-clinical trial identifies genetic modifiers of therapeutic response," Nature, 483:613-617 (2012).

Crawford, A. et al., "Molecular and Transcriptional Basis of CD4+ T Cell Dysfunction during Chronic Infection," Immunity, 40:289-302 (2014).

Crespo, J. et al., "T cell anergy, exhaustion, senescence, and stemness in the tumor microenvironment," Current Opinion in Immunology, 25:214-221 (2013).

Deng, J. et al., "CDK4/6 Inhibition Augments Antitumor Immunity by Enhancing T-cell Activation," Cancer Discov, 8(2):216-33 (2017).

Denkert, C. et al., "Tumor-Associated Lymphocytes As an Independent Predictor of Response to Neoadjuvant Chemotherapy in Breast Cancer," Journal of Clinical Oncology, 28(1):105-113 (2010).

De Simone, M. et al., "Transcriptional Landscape of Human Tissue Lymphocytes Unveils Uniqueness of Tumor-Infiltrating T Regulatory Cells," Immunity, 45:1135-1147 (2016).

Dobin, A. et al., "STAR: ultrafast universal RNA-seq aligner," Bioinformatics, 29(1):15-21 (2013).

Dong, H. et al., "Tumor-associated B7-H1 promotes T-cell apoptosis: A potential mechanism of immune evasion," Nature Medicine, 8(8):793-800 (2002).

Duraiswamy, J. et al., "Dual Blockade of PD-1 and CTLA-4 Combined with Tumor Vaccine Effectively Restores T-Cell Rejection Function in Tumors," Cancer Res, 73(12):3591-3603 (2013).

Ebert, P. J. R. et al., "MAP Kinase Inhibition Promotes T Cell and Antitumor Activity in Combination with PD-L1 Checkpoint Blockade," Immunity, 44:609-621 (2016).

Eden, E. et al., "GOrilla: a tool for discovery and visualization of enriched GO terms in ranked gene lists," BMC Bioinformatics, 10:48 (2009), doi:10.1186/1471-2105-10-48, 7 pages.

Ester, M. et al., "A Density-Based Algorithm for Discovering Clusters in Large Spatial Databases with Noise," Published in Proceedings of 2nd International Conference on Knowledge Discovery and Data Mining (KDD-96, http://citeseerx.ist.psu.edu/viewdoc/summary?doi=10.1.1.71.1980 (1996), 6 pages.

Fabian, M. A. et al., "A small molecule-kinase interaction map for clinical kinase inhibitors," Nature Biotechnology, 23(3):329-336 (2005).

Garcia, C. A. et al., "Antigenic Experience Dictates Functional Role of Glycogen Synthase Kinase-3 in Human CD4+ T Cell Responses," J Immunol, 181:8363-8371 (2008).

Goel, S. et al., "CDK4/6 inhibition triggers anti-tumour immunity," Nature, 548:471-475 (2017), and 16 pages Supplemental Methods, 5 pages Reporting Summaries.

Grivennikov, S. et al., "IL-6 and Stat3 Are Required for Survival of Intestinal Epithelial Cells and Development of Colitis-Associated Cancer," Cancer Cell, 15:103-113 (2009).

Handschick, K. et al., "Cyclin-Dependent Kinase 6 Is a Chromatin-Bound cofactor for NF-κB-Dependent Gene Expression," Molecular Cell, 53:193-208 (2014).

He, S. et al., "Transient CDK4/6 inhibition protects hematopoietic stem cells from chemotherapy-induced exhaustion," Sci. Transl. Med., 9:eaal3986 (2017), doi:10.1126/scitranslmed.aal3986, 11 pages.

Infante, J. R. et al., "A Phase I Study of the Cyclin-Dependent Kinase 4/6 Inhibitor Ribociclib (LEE011) in Patients with Advanced Solid Tumors and Lymphomas," Clin Cancer Res, 22(23):5696-5705 (2016).

Jenkins, R. W. et al., "EX Vivo Profiling of PD-1 Blockade Using Organotypic Tumor Spheroids," Cancer Discov, 8(2):196-215 (2017).

Jung, H. & Miller, R. J., "Activation of the nuclear factor of activated T-cells (NFAT) mediates upregulation of CCR2 chemokine receptors in dorsal root ganglion (DRG) neurons: A possible mechanism for activity-dependent transcription in DRG neurons in association with neuropathic pain," Mol. Cell. Neurosci., 37:170-177 (2008).

Kaluza, K. M. et al., "Adoptive T cell therapy promotes the emergence of genomically altered tumor escape variants," Int. J. Cancer, 131:844-854 (2012).

Karpurapu, M. et al., "Cyclin D1 Is a Bona Fide Target Gene of NFATc1 and Is Sufficient in the Mediation of Injury-induced Vascular Wall Remodeling," Journal of Biological Chemistry, 285(5):3510-3523 (2010), and 2 pages Supplemental Material.

Kelderman, S. et al., "Acquired and intrinsic resistance in cancer immunotherapy," Molecular Oncology, 8:1132-1139 (2014).

Kim, H.-P. & Leonard, W. J., "The basis for TCR-mediated regulation of the IL-2 receptor α chain gene: role of widely separated regulatory elements," The EMBO Journal, 21(12):3051-3059 (2002).

Kollmann, K. et al., "A Kinase-Independent Function of CDK6 Links the Cell Cycle to Tumor Angiogenesis," Cancer Cell, 24:167-181 (2013), and 2 pages Corrections.

Korthauer, K. D. et al., "A statistical approach for identifying differential distributions in single-cell RNA-seq experiments," Genome Biology, 17:222 (2019), doi:10.1186/s13059-016-1077-y, 15 pages.

Koyama, S. et al., "Adaptive resistance to therapeutic PD-1 blockade is associated with upregulation of alternative immune checkpoints," Nature Communications, 7:10501, doi:10.1038/ncomms10501 (2016), 9 pages.

Leach, D. R. et al., "Enhancement of Antitumor Immunity by CTLA-4 Blockade," Science, 271(5256):1734-1736 (1996), doi:10.1126/science.271.5256.1734.

(56) References Cited

OTHER PUBLICATIONS

Lopez, P. G. et al., "Efficacy and safety of abemaciclib combined with either LY3023414 or pembrolizumab in stage IV NSCLC," Annals of Oncology, 28, Supp 5 (2017), doi:10.1093/annonc/mdx380, 1 page.
Macián, F. et al., "Gene expression elicited by NFAT in the presence or absence of cooperative recruitment of Fos and Jun," The EMBO Journal, 19(17):4783-4795 (2000).
Macián, F., "NFAT Proteins: Key Regulators of T-Cell Development and Function," Nature Reviews Immunology, 5(6):472-84 (2005).
Mahoney, K. M. et al., "Combination cancer immunotherapy and new immunomodulatory targets," Nature Reviews Drug Discovery, 14:561-584 (2015).
Martinez, G. J. et al., "The Transcription Factor NFAT Promotes Exhaustion of Activated CD8+ T Cells," Immunity, 42:265-278 (2015).
McFadden, D. G. et al., "Mutational landscape of EGFR-, MYC-, and Kras-driven genetically engineered mouse models of lung adenocarcinoma," PNAS, 113(42):E6409-E6417 (2016), https://doi.org/10.1073/pnas.1613601113, 9 pages.
Min, I. M. et al., "The Transcription Factor EGR1 Controls Both the Proliferation and Localization of Hematopoietic Stem Cells," Cell Stem Cell, 2:380-391 (2008).
Mognol, G. P. et al., "Cell cycle and apoptosis regulation by NFAT transcription factors: new roles for an old player," Cell Death and Disease, 7:e2199 (2016), http://dx.doi.org/10.1038/cddis.2016.97, 13 pages.
NCBI Accession No. GSE89477, Nov. 26, 2017, 3 pages.
Ngiow, S. F. et al., "A Threshold Level of Intratumor CD8+ T-cell PD1 Expression Dictates Therapeutic Response to Anti-PD1," Cancer Res, 75(18):3800-11 (2015).
Nishimura, H. et al., "Development of Lupus-like Autoimmune Diseases by Disruption of the PD-1 Gene Encoding an ITIM Motif-Carrying Immunoreceptor," Immunity, 11:141-151 (1999).
Ohteki, T. et al., "Negative Regulation of T Cell Proliferation and Interleukin 2 Production by the Serine Threonine Kinase GSK-3," J. Exp. Med., 192(1):99-104 (2000).
Paine, A. et al., "IL-2 Upregulates CD86 Expression on Human CD4+ and CD8+ T Cells," J Immunol, 188:1620-1629 (2012), doi:https://doi.org/10.4049/jimmunol.1100181.
Pardoll, D. M., "The blockade of immune checkpoints in cancer immunotherapy," Nature Reviews Cancer, 12(4):252-264 (2012).
Peng, D. et al., "Epigenetic silencing of TH1-type chemokines shapes tumour immunity and immunotherapy," Nature, 527:249-253 (2015) and Supplementary Materials, 11 pages.
Phan, G. Q. et al., "Cancer regression and autoimmunity induced by cytotoxic T lymphocyte-associated antigen 4 blockade in patients with metastatic melanoma," PNAS, 100(14):8372-8377 (2003).
Porter, C. M. et al., "Identification of Amino Acid Residues and Protein Kinases Involved in the Regulation of NFATc Subcellular Localization," The Journal of Biological Chemistry, 275(5):3543-3551 (2000).
Puyol, M. et al., "A Synthetic Lethal Interaction between K-Ras Oncogenes and Cdk4 Unveils a Therapeutic Strategy for Non-small Cell Lung Carcinoma," Cancer Cell, 18:63-73 (2010).
Quigley, M. et al., "Transcriptional analysis of HIV-specific CD8+ T cells shows that PD-1 inhibits T cell function by upregulating BATF," Nature Medicine, 16(10):1147-1151 (2010), and 1 page Online Methods.
Risso, D. et al., "Normalization of RNA-seq data using factor analysis of control genes or samples," Nature Biotechnology, 32(9):896-902 (2014), and Online Methods, 3 pages.
Rizvi, N. A. et al., "Mutational landscape determines sensitivity to PD-1 blockade in non-small cell lung cancer," Science, 348(6230):124-128 (2015).
Robert, C. et al., "Pembrolizumab versus Ipilimumab in Advanced Melanoma, The New England Journal of Medicine," 372(26):2521-2532 (2015).
Scheicher, R. et al., "CDK6 as a key regulator of hematopoietic and leukemic stem cell activation," Blood, 125(1):90-101 (2015).
Schumacher, T. N. & Schreiber, R. D., "Neoantigens in cancer immunotherapy," Science, 348:69-74 (2015).
Scialdone, A. et al., "Computational assignment of cell-cycle stage from single-cell transcriptome data," Methods, 85:54-61 (2015).
Sharma, P. & Allison, J. P., "Immune Checkpoint Targeting in Cancer Therapy: Toward Combination Strategies with Curative Potential," Cell, 161:205-214 (2015).
Soneson, C. et al., "Differential analyses for RNA-seq: transcript-level estimates improve gene-level inferences [version 1; peer review: 2 approved]," F1000 Research, 4:1521 (2015), https://doi.org/10.12688/f1000research.7563.1, 21 pages.
Sullivan, R. J. et al., "The Intersection of Immune-Directed and Molecularly Targeted Therapy in Advanced Melanoma: Where We Have Been, Are, and Will Be," Clin Cancer Res; 19(19):5283-5291 (2013).
Tholey, A. et al., "Direct Effects of Phosphorylation on the Preferred Backbone Conformation of Peptides: A Nuclear Magnetic Resonance Study," Biophysical Journal, 76:76-87 (1999).
Tumeh, P. C. et al., "PD-1 blockade induces responses by inhibiting adaptive immune resistance," Nature, 515:568-571 (2014), and 12 pages Supplemental Methods.
Veinotte, L. et al., "CXCL16-positive dendritic cells enhance invariant natural killer T cell-dependent IFNγ production and tumor control," Oncoimmunology, 5(6):e1160979 (2016), doi:10.1080/2162402X.2016.1160979, 13 pages.
Wells, A. D. & Morawski, P. A., "New roles for cyclin-dependent kinases in T cell biology: linking cell division and differentiation," Nature Reviews Immunology, 14:261-270 (2014).
Yu, H.-B. et al., "NFATc2 mediates epigenetic modification of dendritic cell cytokine and chemokine responses to dectin-1 stimulation," Nucleic Acids Research, 43(2):836-847 (2015).
Zhang, S. et al., "Nuclear Factor of Activated T Cells Regulates Neutrophil Recruitment, Systemic Inflammation, and T-Cell Dysfunction in Abdominal Sepsis," Infection and Immunity, 82(8):3275-3288 (2014).
Zhou, B. et al., "Characterization of Nfatc1 regulation identifies an enhancer required for gene expression that is specific to pro-valve endocardial cells in the developing heart," Development and Disease, 132:1137-1146 (2005).
Stedman's Medical Dictionary, 27th edition. (Baltimore: Lippincott Williams & Wilkins, 2000), s.v. "intermittent".

\* cited by examiner

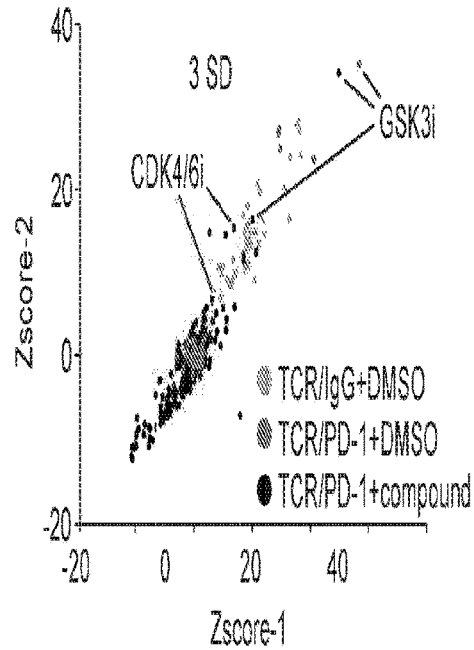
FIG.1A
FIG.1B
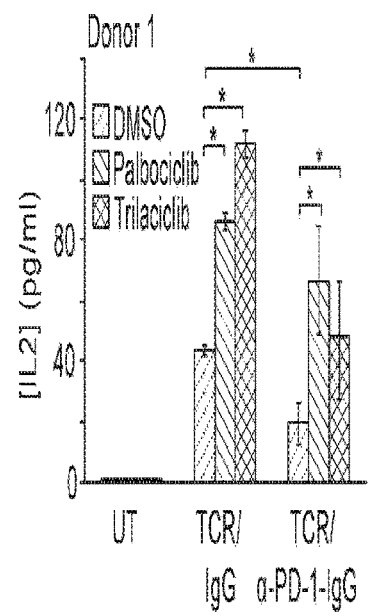
FIG.1C
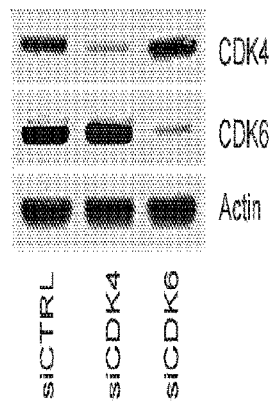
FIG.1D
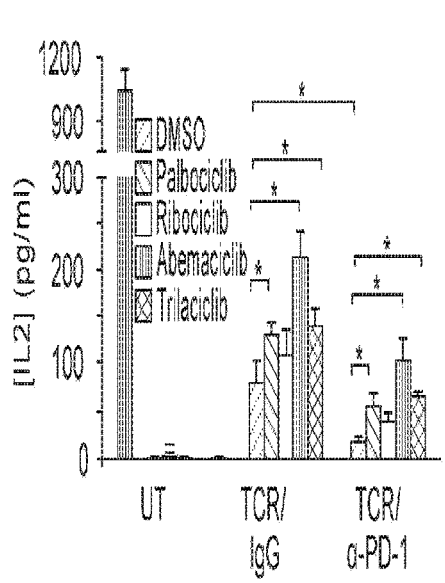
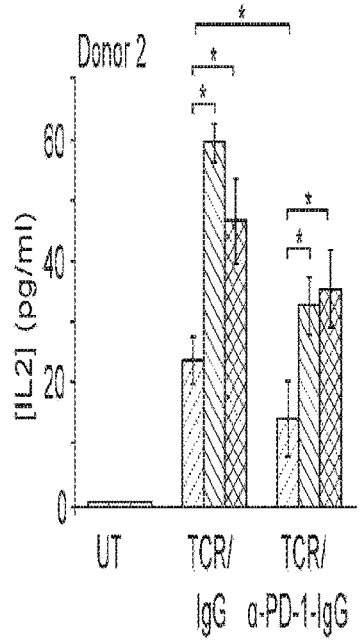
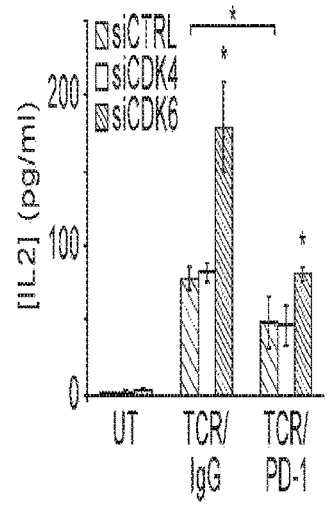
FIG.1E

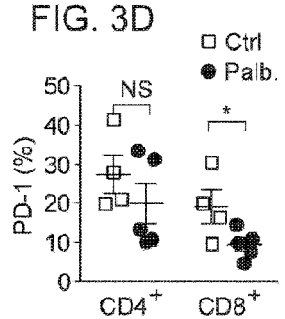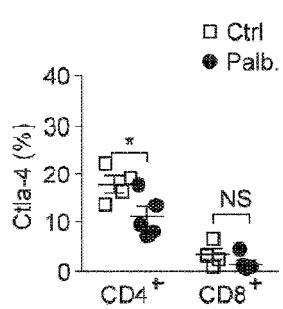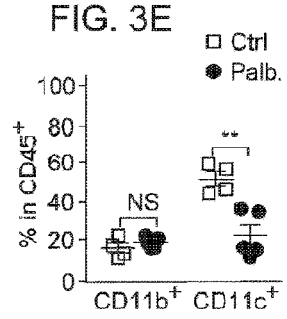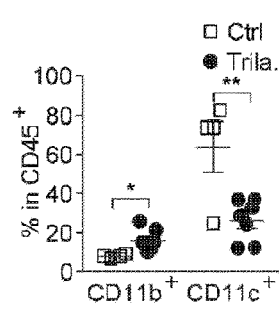

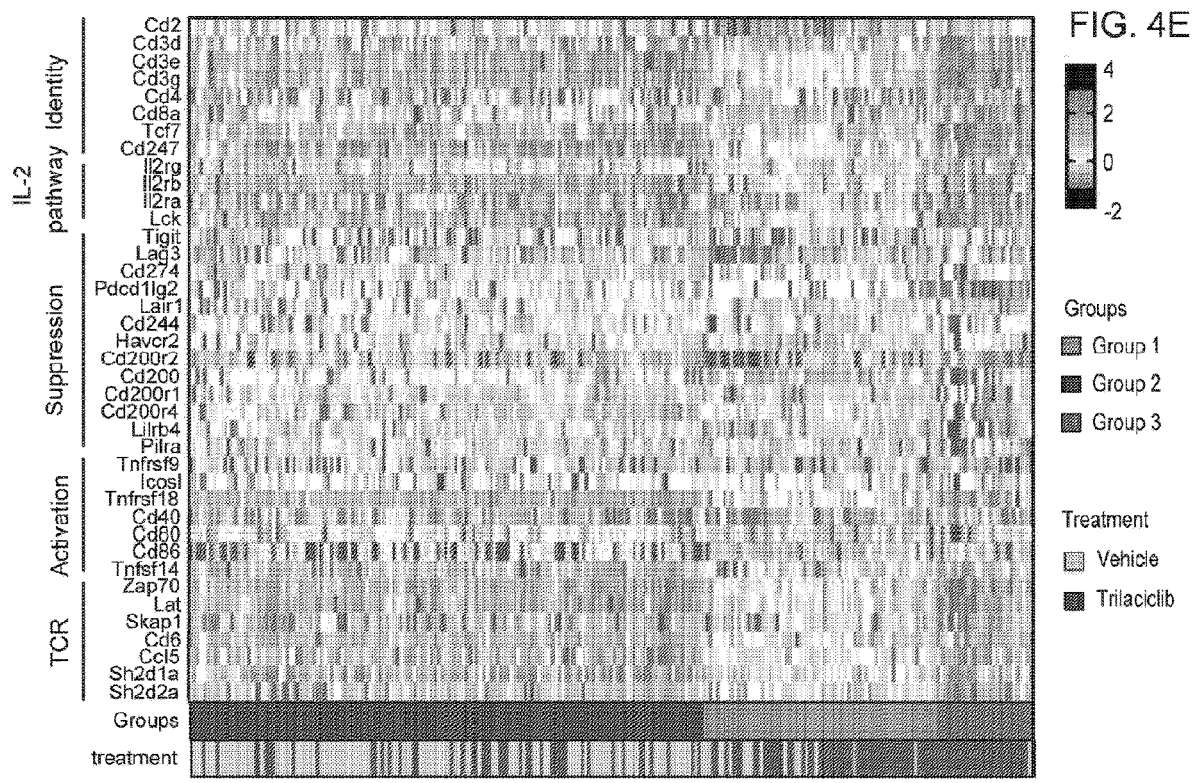

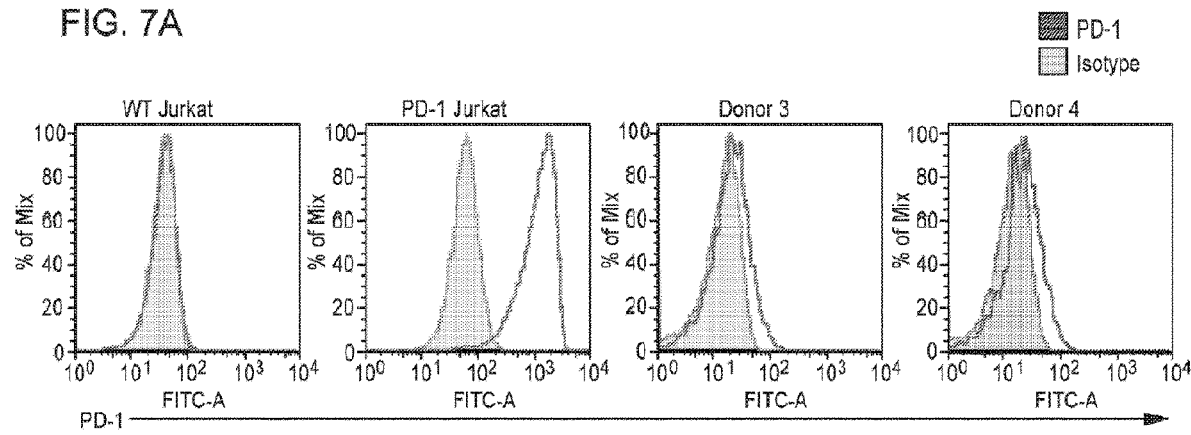

| Compound | IC50 (nM) | |
|---|---|---|
| | GSK3 α | GSK3 β |
| Palbociclib | 721 ± 273 | 728 ± 134 |
| Abemaciclib | 8.67 ± 0.271 | 16.7 ± 0.638 |
| Trilaciclib | 305 ± 9.52 | 325 ± 12.9 |

FIG. 7D  6 h

FIG.9A
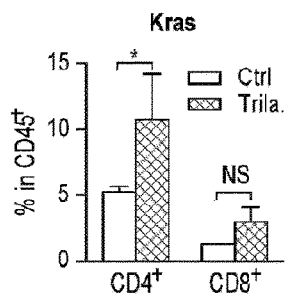 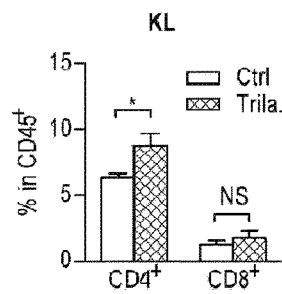 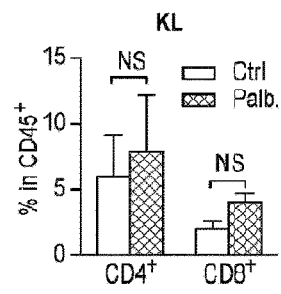 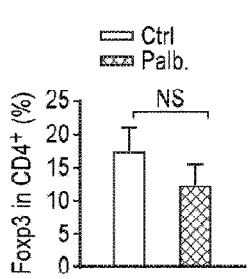
FIG.9C
FIG.9B
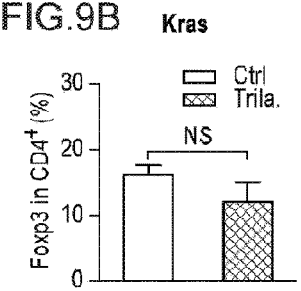 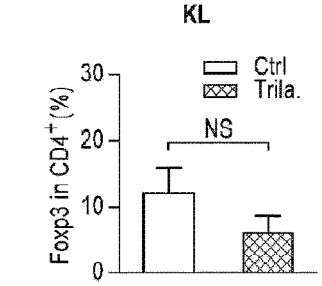 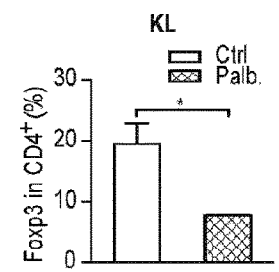 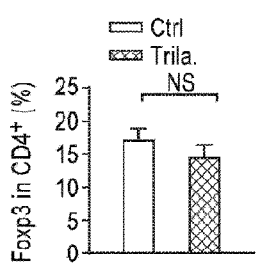

SEQUENCE LISTING

```
<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: Forward IL-3 primer

<400> SEQUENCE: 1
caacctcaat ggggaagacc a                                             21

<210> SEQ ID NO 2
<211> LENGTH: 19
<212> TYPE: DNA
<213> ORGANISM: Artificial Sequence
<220> FEATURE:
<223> OTHER INFORMATION: Reverse IL-3 primer

<400> SEQUENCE: 2
tggattggat gtcgcgtgg                                                19

<210> SEQ ID NO 3
<211> LENGTH: 24
<212> TYPE: DNA
<213> ORGANISM: Artificial Sequence
<220> FEATURE:
<223> OTHER INFORMATION: Forward GM-CSF primer

<400> SEQUENCE: 3
tgctgagatg aatgaaacag taga                                          24

<210> SEQ ID NO 4
<211> LENGTH: 19
<212> TYPE: DNA
<213> ORGANISM: Artificial Sequence
```

```
<220> FEATURE:
<223> OTHER INFORMATION: Reverse GM-CSF primer

<400> SEQUENCE: 4
ctgggttgca caggaagtt                                               19

<210> SEQ ID NO 5
<211> LENGTH: 20
<212> TYPE: DNA
<213> ORGANISM: Artificial Sequence
<220> FEATURE:
<223> OTHER INFORMATION: Forward Actin primer

<400> SEQUENCE: 5
cgcaccactg gcattgtcat                                              20

<210> SEQ ID NO 6
<211> LENGTH: 20
<212> TYPE: DNA
<213> ORGANISM: Artificial Sequence
<220> FEATURE:
<223> OTHER INFORMATION: Reverse Actin primer

<400> SEQUENCE: 6
ttctccttga tgtcacgcac                                              20
```

US 11,865,176 B2

COMPOSITIONS AND METHODS OF MODULATING ANTI-TUMOR IMMUNITY

CROSS-REFERENCE TO RELATED APPLICATIONS

This application is a U.S. National Phase application, filed under 35 U.S.C. § 371, of International Application No. PCT/US2017/060669, filed on Nov. 8, 2017, which claims priority to, and the benefit of U.S. Provisional Application No. 62/419,160 filed on Nov. 8, 2016, the contents of each of which are incorporated herein by reference in their entireties.

GOVERNMENT INTEREST

This invention was made with government support under [ ] awarded by the [ ]. The government has certain rights in the invention.

INCORPORATION OF THE SEQUENCE LISTING

The contents of the text file named "DFCI148N01US SeqList.txt", which was created on May 7, 2019, and is 2 KB in size, are hereby incorporated by reference in their entirety.

FIELD OF THE INVENTION

The present invention relates generally to modulating ant-tumor immunity be combining CDK4/6 inhibitors with immune checkpoint inhibition.

BACKGROUND OF THE INVENTION

Immunotherapies that harness or enhance a patient's immune system to target their tumors have recently been developed. The discovery of immune checkpoint receptors, such as CTLA-4 and PD-1, that repress the activity of anti-tumor T cells, led to the development of blocking antibodies directed against these co-inhibitory receptors or their ligands, including ipilimumab (anti-CTLA-4), pembrolizumab (anti-PD-1), nivolumab (anti-PD-1), atezolizumab (anti-PD-L1) and durvalumab (anti-PD-L1). Strikingly, some patients treated with checkpoint inhibitors experience durable tumor regression, in contrast to targeted small molecule therapies where tumor relapse is a common occurrence.

However, despite promising clinical results, checkpoint blockade therapies are only successful in a subset of patients, and certain tumor types respond more favorably than others. Furthermore, it is increasingly appreciated that, as in the case of targeted therapies, tumors can acquire resistance against immunotherapies.

There remains a need for treatments that will broaden the types of tumors that respond to immunotherapy, and further enhance the specificity and efficacy of anti-tumor activity of existing approaches.

SUMMARY OF THE INVENTION

In various aspects, the invention provides methods of treating a tumor, decreasing tumor burden or increasing T-cell infiltration of a tumor in a subject by administering to the subject a CDK4/6 inhibitor and an immune checkpoint inhibitor. The CDK4/6 inhibitor is administered in an amount sufficient to increase IL-2 and/or IFN-γ production in a tumor infiltrating lymphocyte (TIL). In another aspect, the CDK4/6 inhibitor is administered the in an amount sufficient to increase CXCL-9 and/or CXCL-10 production In another aspect, the invention provides methods of increasing IL-2 and/or IFN-γ production in a tumor infiltrating lymphocyte (TIL) by contacting the TIL with or administering to a subject having a tumor a CDK4/6 inhibitor. Optionally the TIL is contacted with or the subject is administered an immune checkpoint inhibitor.

In a further aspect, the invention provides method of augmenting anti-tumor immunity in a subject comprising administering to the subject a CDK4/6 inhibitor in an amount sufficient to increase T-cell activation. Optionally the TIL is contacted with or the subject is administered an immune checkpoint inhibitor.

The subject is receiving a cancer therapy. The cancer therapy is a targeted therapy such as immunotherapy.

In yet another aspect, the invention provides a method of inhibiting the phosphorylation of Nuclear Factor of Activated T cell (NFAT) by contacting a cell expressing NFAT with a CDK4/6 inhibitor or a CDK6 inhibitor.

The TIL is a CD8+ T-cell, a CD4+ T-cell. A T effector cell, a T helper cell or a T regulatory cell.

Checkpoint inhibitors include for example a CD27, CD28, CD40, CD 122, CD137, OX40, GITR, ICOS, A2AR, B7-H3, B7-H4, BTLA, CTLA-4, IDO, KIR, LAG3, PD-1, PD-L1, TIM-2, or VISTA inhibitor. For example, the checkpoint inhibitor a CD27, CD28, CD40, CD 122, CD137, OX40, GITR, ICOS, A2AR, B7-H3, B7-H4, BTLA, CTLA-4, IDO, KIR, LAG3, PD-1, PD-L1, TIM-2, or VISTA antibody.

The CDK4/6 inhibitor is for example, palbociclib, abemaciclib, trilaciclib, or ribociclib.

The CDK4/6 inhibitor is administered prior to the checkpoint inhibitor. For example, CDK4/6 inhibitor is administered for 2 or 3 days prior to administration of the checkpoint inhibitor.

In some aspects, the subject has or is receiving chemotherapy for a tumor.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the invention will be apparent from and encompassed by the following detailed description and claims.

DETAILED DESCRIPTION OF THE INVENTION

Figure 1F:
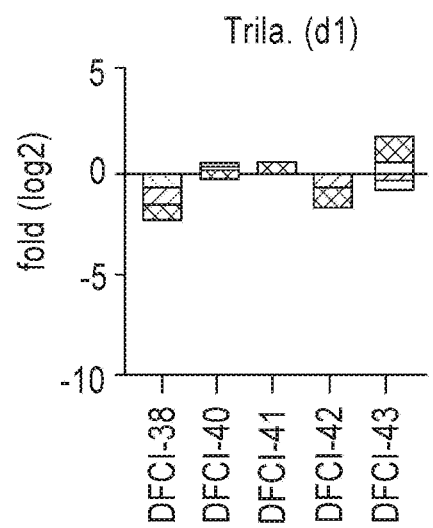
FIG. 1. Small molecule CDK4/6 inhibitors enhance IL-2 secretion from T cells. A. Plot of replicate Z scores from screening of small molecule compounds capable of enhancing IL-2 secretion from stimulated PD-1-Jurkat cells with compounds annotated as GSK2α/β or CDK4/6 inhibitors labeled. B. Quantification of IL-2 levels by EILSA from PD-1-Jurkat cells treated with PMA/ionomycin or 1 μM CDK4/6 inhibitors and stimulated as indicated for 18 h. Results shown as mean±SD (UT, n=2; other conditions, n=5) (*p<0.05). C. Quantification of IL-2 levels by ELISA from primary human CD4+ T cells treated with 100 nM palbociclib or trilaciclib and stimulated as indicated. Results shown as mean±SD (UT, n=2; other conditions, n=4) (*p<0.05). D. Immunoblot for CDK4 and CDK6 from PD-1-Jurkat cells transiently transfected with the indicated siRNA. E. Quantification of IL-2 levels from PD-1-Jurkat cells after transient transfection with siRNA against Cdk4 or Cdk6 and stimulated as indicated for 18 h. Results shown as mean±SD (n=4) (*p<0.05). Cytokine profiling analysis from human patients using patient-derived organotypic tumor spheroids (PDOTS) cultured in 3-dimensional culturing system at day 1 (F) and day 3 (G). Freshly obtained patient samples were digested into spheroids and treated with indicated drugs in the 3-D microfluidic system. Cytokine secretion was analyzed by Luminex and expressed as log 2-fold change relative to untreated control.
Figure 1F:
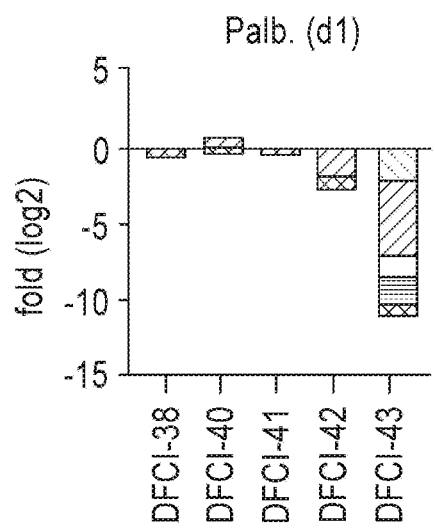

The present invention is based on the discovery that inhibitors of cyclin-dependent kinases 4 and 6 (CDK4/6) significantly enhances T cell activation and contributes to anti-tumor effects in vivo in subjects. This activation of T cells is due in part to de-repression of Nuclear Factor of Activated T cell (NFAT) family proteins and their target genes, critical regulators of T cell function. CDK4/6 inhibitor treatment in vivo reduced proliferation of effector and regulatory T-cell populations, increased infiltration and activation of effector cells, coupled with reduced Treg proliferation created an anti-tumor immune microenvironment that augments the response to immune checkpoint blockade.

Immune checkpoint blockade, exemplified by antibodies targeting the programmed death-1 (PD-1) receptor, can induce durable tumor regressions in some patients. To enhance the efficacy of existing immunotherapies, we screened for small molecules capable of increasing the activity of T cells suppressed immune checkpoint blockade. Specifically, short-term exposure to small molecule inhibitors CDK4/6) significantly enhances T cell activation, contributing to anti-tumor effects in vivo, due in part to de-repression of Nuclear Factor of Activated T cell (NFAT) family proteins and their target genes, critical regulators of T cell function. Although CDK4/6 inhibitors decrease T cell proliferation, they increased tumor infiltration and activation of effector T cells. Moreover, CDK4/6 inhibition augments the response to immune checkpoint blockade in a ex vivo organotypic tumor spheroid culture system and in multiple in vivo murine syngeneic models, thereby providing a rationale for combining CDK4/6 inhibitors and immunotherapies.

Pharmacological inhibition of CDK4/6 promotes T cell activation. Using unbiased small molecule screen, we identified CDK4/6 inhibitors as a class of compounds that could enhance the production of IL-2, a surrogate marker for T cell activation, even when suppressive signaling from immune checkpoints (e.g. PD-1) was enforced. Mechanistically, it was shown that CDK4/6 regulated the activity of NFAT family transcription factors, which are critically important for proper activation and function of T cells. Finally, ex vivo and in vivo studies revealed that small molecule-mediated inhibition of CDK4/6 resulted in increased anti-tumor activity, particularly in conjunction with immune checkpoint blockade, and this effect was largely dependent on T cells.

This finding was especially surprising because inhibiting proliferation should disrupt the clonal expansion of tumor antigen-specific T cells, thereby reducing the activity of the antitumor immune response. Instead, it is apparent that properly timed doses of CDK4/6i can promote T cell activation and augment the effects of immune checkpoint blockade. Indeed, it was discovered that short-term treatment with CDK4/6i led to heightened secretion of IFNγ from CD8+ T cells in the presence of Treg, which often correlates with enhanced anti-tumor cytotoxicity. Moreover, it was discovered in both murine models and human patient samples that treatment with CDK4/6i resulted in increased levels of Th1 cytokines/chemokines, including CXCL9, and CXCL10. As CXCL9/10 are known to be strongly induced by IFNγ, we speculate that the heightened levels of Th1 cytokines/chemokines is partly due to increased levels of IFNγ, resulting from enhanced T cell activity after CDK4/6 inhibition.

Interestingly, our study shows that certain types of T cells, especially T regulatory cells, are more susceptible to CDK4/6 inhibition, which may be due to differing expression levels of CDK4/6. A recent study performed transcriptional analysis of human tissue lymphocytes (including Tregs, Th1, and Th17) located either within tumors or in normal tissue (48). Interestingly, they reported that Tregs in general had higher expression of CDK6 than other T cell subtypes, including tissue-resident Th1 and Th17 cells, as well circulating naïve, central memory, and effector memory CD8$^+$ T cells, suggesting that higher levels of CDK6 and potentially greater dependence on CDK6 in Tregs could account for their increased sensitivity to CDK4/6 inhibitors, which in turn releases suppression of IFNγ production from CD8$^+$ T cells.

Further, we discovered that NFAT4 is a novel substrate of CDK6, but not CDK4, and that CDK4/6 inhibitors enhance NFAT activity in activated T cells. Specifically, it was discovered that CDK4/6i resulted in decreased phospho-NFAT, which lead to increased nuclear translocation and enhanced NFAT transcriptional activity.

Accordingly, short-term pharmacological inhibition of CDK4/6 will boost an anti-tumor response, even in the context of immune checkpoint expression. Whereas long-term inhibition of CDK4/6 could be immunosuppressive due to adverse effects on lymphocyte proliferation, short, carefully timed doses of CDK4/6 inhibitors with immune checkpoint inhibition (e.g., anti-PD-1/PD-L1 antibodies) may be an effective anticancer strategy.

Accordingly, the present invention defines a previously unrecognized immunomodulatory function of CDK4/6 and suggests that combining CDK4/6 inhibitors with immune checkpoint blockade may increase treatment efficacy in patients.

Cyclin-Dependent Kinases 4 and 6 (CDK4/6) Inhibitors

A Cyclin-Dependent Kinases 4 and 6 (CDK4/6) inhibitor is a compound that decreases expression or activity of cyclin-dependent kinases 4 and 6.

Cyclin-dependent kinases (CDKs) are a family of proline-directed serine/threonine kinases that are conserved across eukaryotes. They are also involved in regulating transcription, mRNA processing, and the differentiation of nerve cells. They are present in all known eukaryotes, and their regulatory function in the cell cycle has been evolutionarily conserved. CDKs are relatively small proteins, with molecular weights ranging from 34 to 40 kDa, and contain little more than the kinase domain. By definition, a CDK binds a regulatory protein called a cyclin. Without cyclin, CDK has little kinase activity; only the cyclin-CDK complex is an active kinase. CDKs phosphorylate their substrates on serines and threonines, so they are serine-threonine kinases.

The classical cell cycle CDKs (e.g. 1, 2, 4, and 6) regulate checkpoints to ensure proper progression through the cell cycle (19), and thus have long been attractive targets for pharmacological inhibition for treating cancers.

A biological activity of aCDK4/6 includes for example driving the cell cycle from G0 or G1 to S phase.

CDK4/6 drives the cell cycle from G0 or G1 to S phase by phosphorylation. A CDK4/6 inhibitor decreases expression or activity of CDK4/6. A decrease in CDK4/6 activity is defined by a reduction of a biological function of the CDK4/6. For example, a decrease or reduction in CDK4/6 expression or biological activity refers to at least a 1%, 2%, 5%, 10%, 15%, 20%, 25%, 30%, 35%, 40%, 45%, 50%, 60%, 70%, 80%, 90% or 100% decrease in CDK4/6 expression or activity compared to a control.

The CDK4/6 inhibitor is a small molecule. A "small molecule" as used herein, is meant to refer to a composition that has a molecular weight in the range of less than about 5 kD to 50 daltons, for example less than about 4 kD, less than about 3.5 kD, less than about 3 kD, less than about 2.5 kD, less than about 2 kD, less than about 1.5 kD, less than about 1 kD, less than 750 daltons, less than 500 daltons, less than about 450 daltons, less than about 400 daltons, less than about 350 daltons, less than about 300 daltons, less than about 250 daltons, less than about 200 daltons, less than about 150 daltons, or less than about 100 daltons. Small molecules can be, e.g., nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention.

For example, the CDK4/6 inhibitor is palbociclib (PD-0332991, PD991), trilaciclib (G1T28), abemaciclib, or ribociclib. Other CDK4/6 inhibitor are known in the art and include but not limited to those disclosed in WO 2012/061156; WO 2010/020675; WO 2011/101409; WO 2005/052147; WO 2006/074985; US 2007/0179118; 2014/0275066; 2011/0224227; U.S. Pat. Nos. 8,829,012; 8,822,683; 8,598,186; 8,691,830; 8,598,197, 9,102,682; and 9,260,442.

Immune Checkpoint Inhibitors

By immune checkpoint inhibitor it is meant a compound that inhibits a protein in the checkpoint signally pathway. Proteins in the checkpoint signally pathway include for example, CD27, CD28, CD40, CD 122, CD137, OX40, GITR, ICOS, A2AR, B7-H3, B7-H4, BTLA, CTLA-4, IDO, KIR, LAG3, PD-1, PD-L1, PD-L2, TIM-3, TIGIT, Lair1, CD244, HAVCR2, CD200, CD200R1, CD200R2, CD200R4, LILRB4, PILRA, ICOSL, 4-1BB or VISTA. Immune checkpoint inhibitors are known in the art. For example, the immune checkpoint inhibitor can be a small molecule. A "small molecule" as used herein, is meant to refer to a composition that has a molecular weight in the range of less than about 5 kD to 50 daltons, for example less than about 4 kD, less than about 3.5 kD, less than about 3 kD, less than about 2.5 kD, less than about 2 kD, less than about 1.5 kD, less than about 1 kD, less than 750 daltons, less than 500 daltons, less than about 450 daltons, less than about 400 daltons, less than about 350 daltons, less than 300 daltons, less than 250 daltons, less than about 200 daltons, less than about 150 daltons, less than about 100 daltons. Small molecules can be, e.g., nucleic acids, peptides, polypeptides, peptidomimetics, carbohydrates, lipids or other organic or inorganic molecules.

Alternatively, the immune checkpoint inhibitor is an antibody or fragment thereof. For example, the antibody or fragment thereof is specific to a protein in the checkpoint signaling pathway, such as CD27, CD28, CD40, CD 122, CD137, OX40, GITR, ICOS, A2AR, B7-H3, B7-H4, BTLA, CTLA-4, IDO, KIR, LAG3, PD-1, PD-L1, PD-L2, TIM-3, TIGIT, Lair1, CD244, HAVCR2, CD200, CD200R1, CD200R2, CD200R4, LILRB4, PILRA, ICOSL, 4-1BB or VISTA.

Exemplary, anti-immune checkpoint antibodies include for example ipiliumab (anti-CTLA-4), penbrolizumab (anti-PD-L1), nivolumab (anti-PD-L1), atezolizumab (anti-PD-L1), and duralumab (anti-PD-L1)

Therapeutic Methods

In various aspects, the invention provides methods of treating cancer in a subject, decreasing tumor burden, increasing T-cell activation, e.g., effector T-cell activation, increases T-cell infiltration into tumor, de-repression of Nuclear Factor of Activated T-cell (NFAT) protein or increasing IL-2 and/or IFN-γ production in a tumor infiltrating lymphocyte (TIL). The method includes administering to the subject or contacting a tumor with a compound that inhibits the expression or activity of CDK4/6.

Cells are directly contacted with the compound. Alternatively, the compound is administered systemically.

A tumor is treated in a subject by administering to a subject a CDK4/6 inhibitor and an immune checkpoint inhibitor.

Tumor burden is decreased in a subject by administering to a subject a CDK4/6 inhibitor and an immune checkpoint inhibitor. Tumor burden is decrease 1-fold 2-fold, 3-fold, 4-fold or 5-fold compared to the tumor burden prior to treatment, T-cell infiltration of a tumor is increased in a subject by administering to the subject a CDK4/6 inhibitor. Optionally, the subject is further administered an immune checkpoint inhibitor. T-cell infiltration is increased 1-fold 2-fold, 3-fold, 4-fold or 5-fold compared to T-cell infiltration of the tumor prior to treatment Anti-tumor immunity is augmented (i.e., increased) in a subject by administering to said subject a CDK4/6 inhibitor in an amount sufficient to increase T-cell activation. Optionally, the subject is further administered an immune checkpoint inhibitor. T-cell activation is measured by methods know in the art.

Phosphorylation of Nuclear Factor of Activated T cell (NFAT) is inhibited (e.g. decreased) by contacting a cell expressing NFAT with a CDK4/6 inhibitor or a CDK6 inhibitor.

In the various methods of the invention the CDK4/6 inhibitor is administered in an amount sufficient to increase IL-2 and/or IFN-γ production a tumor infiltrating lymphocyte (TIL). Alternatively, the CDK4/6 inhibitor is administered in an amount sufficient to increase CXCL-9 and/or CXCL-10 production.

The invention also features methods of increasing IL-2 and/or IFN-γ production in a tumor infiltrating lymphocyte (TIL) by contacting the TIL or administering to a subject having a tumor a CDK4/6 inhibitor. Optionally, the TIL is further contacted with an immune checkpoint inhibitor.

A TIL is for example a CD8+ T-cell, a CD4+ T-cell, a T effector cell, a T helper cell or a T regulatory cell.

Tumors amenable to treatment by the methods of thw invention include any cancers, such as, by way of non-limiting example, melanoma, non-small cell lung cancer, nasopharyngeal cancer, glioblastoma/mixed glioma, colon adenocarcinoma, hepatocellular carcinoma, urothelial cancer, multiple myeloma, ovarian cancer, gastric carcinoma, esophageal cancer, pancreatic cancer, renal cell carcinoma (RCC), breast cancer, lymphomas, such as Hodgkin's lymphoma, and leukemias. In some embodiments, the cancer is a bladder cancer, a bone cancer, a breast cancer, a carcinoid, a cervical cancer, a colon cancer, an endometrial cancer, a glioma, a head and neck cancer, a liver cancer, a lung cancer, a lymphoma, such as Hodgkin's lymphoma, a melanoma, an ovarian cancer, a pancreatic cancer, a prostate cancer, a renal cancer, a sarcoma, a skin cancer, a stomach cancer, a testis cancer, a thyroid cancer, a urogenital cancer, and/or a urothelial cancer.

In other embodiments, the cancer is selected from the group consisting of melanoma (MEL), renal cell carcinoma (RCC), squamous non-small cell lung cancer (NSCLC), non-squamous NSCLC, colorectal cancer (CRC), castration-resistant prostate cancer (CRPC), hepatocellular carcinoma (HCC), squamous cell carcinoma of the head and neck, carcinomas of the esophagus, ovary, gastrointestinal tract and breast, or a hematologic malignancy such as multiple myeloma, B-cell lymphoma, T-cell lymphoma, Hodgkin's lymphoma, primary mediastinal B-cell lymphoma, and chronic myelogenous leukemia.

In another aspect, the invention provides methods of increasing IL-2 and/or IFN-γ production in a tumor infiltrating lymphocyte (TIL) by contacting the TIL with or administering to a subject having a tumor a CDK4/6 inhibitor. Optionally the TIL is contacted with or the subject is administered an immune checkpoint inhibitor In a further aspect, the invention provides method of augmenting anti-tumor immunity in a subject comprising administering to the subject a CDK4/6 inhibitor in an amount sufficient to increase T-cell activation. Optionally the TIL is contacted with or the subject is administered an immune checkpoint inhibitor.

The subject is receiving a cancer therapy. The cancer therapy is a targeted therapy such as for example, immunotherapy. Alternatively, the cancer therapy is chemotherapy.

The subject will receive, has received or is receiving an immune checkpoint inhibitor therapy.

The immune checkpoint inhibitor is administered contemporaneously with CDK4/6 inhibitor, prior to administration of the CDK4/6 inhibitor or after administration of the CDK4/6 inhibitor. Preferably, the immune checkpoint inhibitor is administered after the CDK4/6 inhibitor. For example, the CDK4/6 inhibitor is administered 1, 2, 3, 4, or 5 days before administration of the checkpoint inhibitor. When administering CDK4/6 inhibitor care is taken not to induce immunosuppression due to adverse effects on lymphocyte proliferation. Thus, short, carefully timed doses of CDK4/6 inhibitors with checkpoint inhibitors are preferred.

Therapeutic Administration

The invention includes administering to a subject a composition comprising a CDK4/6 inhibitor. The subject has received or will receive treatment with a checkpoint inhibitor.

An effective amount of a CDK4/6 inhibitor is preferably from about 0.1 mg/kg to about 150 mg/kg. Effective doses vary, as recognized by those skilled in the art, depending on route of administration, excipient usage, and co-administration with other therapeutic treatments including use of other anti-proliferative agents or therapeutic agents for treating, preventing or alleviating a symptom of a cancer. A therapeutic regimen is carried out by identifying a mammal, e.g., a human patient suffering from a cancer using standard methods.

Doses may be administered once or more than once. In some embodiments, it is preferred that the CDK4/6 inhibitor is administered once a day, twice a day, or three times a day for a predetermined duration of time. In some aspects, the CDK4/6 inhibitor is administered on alternate days for a predetermined duration of time. The predetermined duration of time may be 1 day, 2 days, 3 days, 4 days, 5 days, 6 days, or 1 week.

Preferably, CDK4/6 inhibitor is administered once a day, twice a day, or three times a day for a predetermined duration of time prior to the administration of a checkpoint inhibitor therapeutic regimen.

Importantly, the CDK4/6 inhibitor is administered in an amount and duration so as not to induce immunosuppression, thereby avoiding adverse effects on lymphocyte proliferation.

The pharmaceutical compound is administered to such an individual using methods known in the art. Preferably, the compound is administered orally, rectally, nasally, topically or parenterally, e.g., subcutaneously, intraperitoneally, intramuscularly, and intravenously. The inhibitors are optionally formulated as a component of a cocktail of therapeutic drugs to treat cancers. Examples of formulations suitable for parenteral administration include aqueous solutions of the active agent in an isotonic saline solution, a 5% glucose solution, or another standard pharmaceutically acceptable excipient. Standard solubilizing agents such as polyvinylpyrrolidone (PVP) or cyclodextrins are also utilized as pharmaceutical excipients for delivery of the therapeutic compounds.

The therapeutic compounds described herein are formulated into compositions for other routes of administration utilizing conventional methods. For example, the therapeutic compounds are formulated in a capsule or a tablet for oral administration. Capsules may contain any standard pharmaceutically acceptable materials such as gelatin or cellulose. Tablets may be formulated in accordance with conventional procedures by compressing mixtures of a therapeutic compound with a solid carrier and a lubricant. Examples of solid carriers include starch and sugar bentonite. The compound is administered in the form of a hard shell tablet or a capsule containing a binder, e.g., lactose or mannitol, conventional filler, and a tableting agent. Other formulations include an ointment, suppository, paste, spray, patch, cream, gel, resorbable sponge, or foam. Such formulations are produced using methods well known in the art.

Therapeutic compounds are effective upon direct contact of the compound with the affected tissue. Accordingly, the compound is administered topically. Alternatively, the therapeutic compounds are administered systemically. For example, the compounds are administered by inhalation. The compounds are delivered in the form of an aerosol spray from pressured container or dispenser which contains a suitable propellant, e.g., a gas such as carbon dioxide, or a nebulizer.

Additionally, compounds are administered by implanting (either directly into an organ or subcutaneously) a solid or resorbable matrix which slowly releases the compound into adjacent and surrounding tissues of the subject.

In some embodiments, it is preferred that the therapeutic compounds described herein are administered in combination with another therapeutic agent, such as a chemotherapeutic agent, radiation therapy, or an anti-mitotic agent. In some aspects, the anti-mitotic agent is administered prior to administration of the present therapeutic compound, in order to induce additional chromosomal instability to increase the efficacy of the present invention to targeting cancer cells. Examples of anti-mitotic agents include taxanes (i.e., paclitaxel, docetaxel), and *vinca* alkaloids (i.e., vinblastine, vincristine, vindesine, vinorelbine).

Definitions

The practice of the present invention employs, unless otherwise indicated, conventional techniques of molecular biology, microbiology, cell biology and recombinant DNA, which are within the skill of the art. See, e.g., Sambrook, Fritsch and Maniatis, MOLECULAR CLONING: A LABORATORY MANUAL, $2^{nd}$ edition (1989); CURRENT PROTOCOLS IN MOLECULAR BIOLOGY (F. M. Ausubel et al. eds., (1987)); the series METHODS IN ENZYMOLOGY (Academic Press, Inc.): PCR 2: A PRACTICAL APPROACH (Mi. MacPherson, B. D. Hames and G. R. Taylor eds. (1995)) and ANIMAL CELL CULTURE (Rd. Freshney, ed. (1987)).

As used herein, certain terms have the following defined meanings. As used in the specification and claims, the singular form "a", "an" and "the" include plural references unless the context clearly dictates otherwise. For example, the term "a cell" includes a plurality of cells, including mixtures thereof.

"Treatment" is an intervention performed with the intention of preventing the development or altering the pathology or symptoms of a disorder. Accordingly, "treatment" refers to both therapeutic treatment and prophylactic or preventative measures. Those in need of treatment include those already with the disorder as well as those in which the disorder is to be prevented. In tumor (e.g., cancer) treatment, a therapeutic agent may directly decrease the pathology of tumor cells, or render the tumor cells more susceptible to treatment by other therapeutic agents, e.g., radiation and/or chemotherapy. As used herein, "ameliorated" or "treatment" refers to a symptom which approaches a normalized value (for example a value obtained in a healthy patient or individual), e.g., is less than 50% different from a normalized value, preferably is less than about 25% different from a normalized value, more preferably, is less than 10% different from a normalized value, and still more preferably, is not significantly different from a normalized value as determined using routine statistical tests.

Thus, treating may include suppressing, inhibiting, preventing, treating, or a combination thereof. Treating refers inter alia to increasing time to sustained progression, expediting remission, inducing remission, augmenting remission, speeding recovery, increasing efficacy of or decreasing resistance to alternative therapeutics, or a combination thereof "Suppressing" or "inhibiting", refers inter alia to delaying the onset of symptoms, preventing relapse of a disease, decreasing the number or frequency of relapse episodes, increasing latency between symptomatic episodes, reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof. The symptoms are primary, while in another embodiment, symptoms are secondary. "Primary" refers to a symptom that is a direct result of the proliferative disorder, while, secondary refers to a symptom that is derived from or consequent to a primary cause. Symptoms may be any manifestation of a disease or pathological condition.

The "treatment of cancer or tumor cells", refers to an amount of peptide or nucleic acid, described throughout the specification, capable of invoking one or more of the following effects: (1) inhibition of tumor growth, including, (i) slowing down and (ii) complete growth arrest; (2) reduction in the number of tumor cells; (3) maintaining tumor size; (4) reduction in tumor size; (5) inhibition, including (i) reduction, (ii) slowing down or (iii) complete prevention, of tumor cell infiltration into peripheral organs; (6) inhibition, including (i) reduction, (ii) slowing down or (iii) complete prevention, of metastasis; (7) enhancement of anti-tumor immune response, which may result in (i) maintaining tumor size, (ii) reducing tumor size, (iii) slowing the growth of a tumor, (iv) reducing, slowing or preventing invasion and/or (8) relief, to some extent, of the severity or number of one or more symptoms associated with the disorder.

As used herein, "an ameliorated symptom" or "treated symptom" refers to a symptom which approaches a normalized value, e.g., is less than 50% different from a normalized value, preferably is less than about 25% different from a normalized value, more preferably, is less than 10% different from a normalized value, and still more preferably, is not significantly different from a normalized value as determined using routine statistical tests.

The terms "patient" or "individual" are used interchangeably herein, and refers to a mammalian subject to be treated, with human patients being preferred. In some cases, the methods of the invention find use in experimental animals, in veterinary application, and in the development of animal models for disease, including, but not limited to, rodents including mice, rats, and hamsters, and primates.

By the term "modulate," it is meant that any of the mentioned activities, are, e.g., increased, enhanced, increased, augmented, agonized (acts as an agonist), promoted, decreased, reduced, suppressed blocked, or antagonized (acts as an antagonist). Modulation can increase activity more than 1-fold, 2-fold, 3-fold, 5-fold, 10-fold, 100-fold, etc., over baseline values. Modulation can also decrease its activity below baseline values.

Thus, the term "cytokine" refers to any of the numerous factors that exert a variety of effects on cells, for example, inducing growth or proliferation. Non-limiting examples of cytokines include, IL-2, stem cell factor (SCF), IL-3, IL-6, IL-7, IL-12, IL-15, G-CSF, GM-CSF, IL-1 α, IL-1 β, MIP-1 α, LIF, c-kit ligand, TPO, and flt3 ligand. Cytokines are commercially available from several vendors such as, for example, Genzyme Corp. (Framingham, Mass.), Genentech (South San Francisco, CA), Amgen (Thousand Oaks, CA) and Immunex (Seattle, WA). It is intended, although not always explicitly stated, that molecules having similar biological activity as wild type or purified cytokines (e.g., recombinantly produced cytokines) are intended to be used within the spirit and scope of the invention and therefore are substitutes for wild type or purified cytokines.

An "effective amount" is an amount sufficient to effect beneficial or desired results. An effective amount can be administered in one or more administrations, applications or dosages.

A "subject" is a vertebrate, preferably a mammal, more preferably a human. Mammals include, but are not limited to, murines, simians, humans, farm animals, sport animals, and pets.

An "antibody" is an immunoglobulin molecule capable of binding an antigen. As used herein, the term encompasses not only intact immunoglobulin molecules, but also anti-idiotypic antibodies, mutants, fragments, fusion proteins, humanized proteins and modifications of the immunoglobulin molecule that comprise an antigen recognition site of the required specificity.

An "antibody complex" is the combination of antibody and its binding partner or ligand.

The term "isolated" means separated from constituents, cellular and otherwise, in which the polynucleotide, peptide, polypeptide, protein, antibody, or fragments thereof, are normally associated with in nature. As is apparent to those of skill in the art, a non-naturally occurring polynucleotide, peptide, polypeptide, protein, antibody, or fragments thereof, does not require "isolation" to distinguish it from its naturally occurring counterpart. In addition, a "concentrated", "separated" or "diluted" polynucleotide, peptide, polypeptide, protein, antibody, or fragments thereof, is distinguishable from its naturally occurring counterpart in that the concentration or number of molecules per volume is greater than "concentrated" or less than "separated" than that of its naturally occurring counterpart. A polynucleotide, peptide, polypeptide, protein, antibody, or fragments thereof, which differs from the naturally occurring counterpart in its primary sequence or for example, by its glycosylation pattern, need not be present in its isolated form since it is distinguishable from its naturally occurring counterpart by its primary sequence, or alternatively, by another characteristic such as glycosylation pattern. Although not explicitly stated for each of the inventions disclosed herein, it is to be understood that all of the above embodiments for each of the compositions disclosed below and under the appropriate conditions, are provided by this invention. Thus, a non-naturally occurring polynucleotide is provided as a separate embodiment from the isolated naturally occurring polynucleotide. A protein produced in a bacterial cell is provided as a separate embodiment from the naturally occurring protein isolated from a eukaryotic cell in which it is produced in nature.

A "composition" is intended to mean a combination of active agent and another compound or composition, inert (for example, a detectable agent, carrier, solid support or label) or active, such as an adjuvant.

A "pharmaceutical composition" is intended to include the combination of an active agent with a carrier, inert or active, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin, REMINGTON'S PHARM. SCI, 15th Ed. (Mack Publ. Co., Easton (1975)).

As used herein, the term "inducing an immune response in a subject" is a term well understood in the art and intends that an increase of at least about 2-fold, more preferably at least about 5-fold, more preferably at least about 10-fold, more preferably at least about 100-fold, even more preferably at least about 500-fold, even more preferably at least about 1000-fold or more in an immune response to an antigen (or epitope) can be detected (measured), after introducing the antigen (or epitope) into the subject, relative to the immune response (if any) before introduction of the antigen (or epitope) into the subject. An immune response to an antigen (or epitope), includes, but is not limited to, production of an antigen-specific (or epitope-specific) antibody, and production of an immune cell expressing on its surface a molecule which specifically binds to an antigen (or epitope). Methods of determining whether an immune response to a given antigen (or epitope) has been induced are well known in the art. For example, antigen specific antibody can be detected using any of a variety of immunoassays known in the art, including, but not limited to, ELISA, wherein, for example, binding of an antibody in a sample to an immobilized antigen (or epitope) is detected with a detectably-labeled second antibody (e.g., enzyme-labeled mouse anti-human Ig antibody). Immune effector cells specific for the antigen can be detected by any of a variety of assays known to those skilled in the art, including, but not limited to, FACS, or, in the case of CTLs, $^{51}$CR-release assays, or $^3$H-thymidine uptake assays.

By "substantially free of endotoxin" is meant that there is less endotoxin per dose of cell fusions than is allowed by the FDA for a biologic, which is a total endotoxin of 5 EU/kg body weight per day.

By "substantially free for mycoplasma and microbial contamination" is meant negative readings for the generally accepted tests know to those skilled in the art. For example, mycoplasm contamination is determined by subculturing a cell sample in broth medium and distributed over agar plates on day 1, 3, 7, and 14 at 37° C. with appropriate positive and negative controls. The product sample appearance is compared microscopically, at 100×, to that of the positive and negative control. Additionally, inoculation of an indicator cell culture is incubated for 3 and 5 days and examined at 600× for the presence of mycoplasmas by epifluorescence microscopy using a DNA-binding fluorochrome. The product is considered satisfactory if the agar and/or the broth media procedure and the indicator cell culture procedure show no evidence of mycoplasma contamination.

The sterility test to establish that the product is free of microbial contamination is based on the U.S. Pharmacopedia Direct Transfer Method. This procedure requires that a pre-harvest medium effluent and a pre-concentrated sample be inoculated into a tube containing tryptic soy broth media and fluid thioglycollate media. These tubes are observed periodically for a cloudy appearance (turbidity) for a 14 day incubation. A cloudy appearance on any day in either medium indicate contamination, with a clear appearance (no growth) testing substantially free of contamination.

EXAMPLES

Example 1: General Methods

Small Molecule Screen.

PD-1-overexpressing Jurkat cells were plated at a concentration of 100,000 cells/well in a total volume of 80 μl. Compounds (100 nl each) from the Institute of Chemistry and Cell Biology (ICCB) EMD Kinase Inhibitor I collection (244 compounds total) (55), consisting of three libraries sold by EMD as InhibitorSelect 96-Well Protein Kinase Inhibitor I (cat #: 539744, 80 compounds), InhibitorSelect 96-Well Protein Kinase Inhibitor II (cat #: 539745, 80 compounds) and InhibitorSelect 96-Well Protein Kinase Inhibitor III (cat #: 539746, 84 compounds), were transferred by stainless steel pin array from library plates to each assay plate. Dynabeads conjugated to α-CD3, α-CD28, and α-PD-1 antibodies were added in 20 for a final assay volume of 100 with a final compound concentration of 3.3 μM and an 8:1 bead:cell ratio. Beads were conjugated to α-CD3/α-CD28/control IgG and added to wells containing DMSO-treated cells as a positive control, while beads conjugated to α-CD3/α-CD28/α-PD1 were added to wells containing DMSO-treated cells as a negative control. Supernatants from each well were analyzed for IL2 levels by AlphaLISA (Perkin Elmers) according to the manufacturer's protocol. Average and standard deviation values were calculated from the PD-1 controls (DMSO-treated cells stimulated with α-CD3/α-CD28/α-PD-1 beads); hits were defined as compounds scoring at least 3 standard deviations from the mean of the controls.

IL2 ELISA.

PD-1-overexpressing Jurkat cells as previously published (23) were stimulated with Dynabeads conjugated to α-CD3 (UCHT1), α-CD28 (28.2), and α-PD-1 (clone EH12 from Gordon Freeman) or control IgG at a 4:1 bead:cell ratio in the presence of 1 μM CDK4/6 inhibitor for 18 h. For primary human T cells, normal donor human blood was obtained through DFCI IRB Protocol 04-430. PBMC were isolated using a Ficoll-Paque density gradient, and purified populations of CD4+ T lymphocytes were obtained through a negative magnetic selection kit according to manufacturer's instructions (Miltenyi). Primary human CD4+ T cells were stimulated with Dynabeads conjugated to a CD3 (UCHT1), α-CD28 (28.2), and recombinant hPD-L1-IgG fusion protein (Gordon Freeman) or control IgG at a 4:1 bead:cell ratio in the presence of 1 μM CDK4/6 inhibitor for 18 h. IL-2 levels in the supernatant were analyzed by AlphaLISA (Perkin Elmers) according to the manufacturer's protocol.

KINOMEscan.

Palbociclib and abemaciclib were profiled by DiscoveRx using KINOMEscan (55). Briefly, the two compounds were tested at 100 nM and 1000 nM. Targeted kinases were visualized using the TREEspot™ compound profile visualization tool. Z'LYTE™ kinase assays were conducted for GSK3α and GSK3β at Life Technologies using Km ATP concentrations.

Expression and Purification of NFATc3 Regulatory Domain.

The regulatory domain of human NFATc3 (residues 1-400) was cloned into a pET151/D-TOPO plasmid and expressed as a fusion protein with an N-terminal His-GB1 solubility tag cleavable with TEV protease. *Escherichia coli* strain BL21 (DE3) carrying the above plasmid were grown at 37° C. in M9 media containing 6 g/l Na2HPO4, 3 g/l KH2PO4, 0.5 g/l NaCl, 1 mM MgSO4, 0.1 mM CaCl2 in H2O supplemented with 4 g/l 12C-glucose and 1 g/l of 15NH4Cl isotopes. Protein expression was induced at an OD of 0.7 by 1 mM isopropyl β-D-1-thiogalactopyranoside (IPTG) at 20° C. Cells were grown for additional 15 hours at 20° C. before harvesting. The harvested cells were resuspended in 40 ml of 50 mM Tris-HCl (pH 8.0), 350 mM NaCl, 10 mM imidazole and 5 mM β-mercaptoethanol (β-ME). The suspended cells were then disrupted by sonication, and the insoluble fraction was removed by centrifugation for 40 min at 16,000 rpm. The protein was initially purified by affinity chromatography using 5 ml of Ni-NTA resin (Qiagen). The supernatant from the cell lysate was incubated with the Ni-NTA resin for one hour. After washing the bound resin with 40 ml of 50 mM Tris-HCl (pH 8.0), 350 mM NaCl, 40 mM imidazole and 5 mM β-ME, the protein was eluted in an identical buffer containing 350 mM imidazole. The elution fraction was dialyzed against a buffer containing 30 mM Na2HPO4 (pH 6.7), NaCl (150 mM), DTT (5 mM) and the His-GB1 solubility tag was cleaved using TEV protease. The digested NFATc3 and His-GB1 were separated and further purified using size exclusion chromatography (GE Healthcare Life Sciences "Superdex 75 10/300 GL").

In Vitro Phosphorylation of NFATc3.

NMR experiments were performed on a Varian (Agilent DD2 700) spectrometer equipped with a cryogenically cooled probe, and the spectrum was recorded at 287 K. CDK4/cyclin D1 and CDK6/cyclin D3 kinases were purchased from Signalchem. The phosphorylation reaction was performed with a sample containing 0.1 mM 15N labeled NFATc3 with the addition of 10 μg CDK4 or 10 μg CDK6 in kinase reaction buffer [50 mM MES (pH 6.7), 140 mM NaCl, 10 Mm MgCl2, 0.1 Mm EDTA, 2 mM ATP and 5 mM DTT]. First, a control experiment of unphosphorylated NFATc3 in same kinase reaction buffer was recorded followed by addition of kinases and phosphorylation was monitored by using 2D 15N-HSQC experiments. In the inhibition assay, ~0.704 of CKD6 was pre-incubated with 704 inhibitor before addition to 15N labeled NFATc3 sample. Here, 2.5 ul of a 1 mM stock of the inhibitor was added to 350 ul of the NMR sample. In a control experiment, the same amount of DMSO (2.5 μL) was added. All spectra were processed using nmrPipe and analyzed with CcpNmr-Analysis (version 2.4.1).

Western Blots and Antibodies.

Cells were lysed in M-PER buffer (Thermo Scientific) containing protease/phosphatase inhibitor cocktail (Roche). Protein concentration was measured using a BCA assay (Pierce). Equivalent amounts of each sample were loaded on 4-12% Bis-Tris gels (Invitrogen), transferred to nitrocellulose membranes, and immunoblotted with antibodies against CDK4, CDK6, β-catenin, active β-catenin, phospho-S536-p65, total p65, and Actin (Cell Signaling); pS172-NFAT2 (R&D); and NFAT2 (Invitrogen). IRDye®800-labeled goat anti-rabbit IgG and IRDye®680-labeled goat anti-mouse IgG (LI-COR) secondary antibodies were purchased for LI-COR, and membranes were detected on an Odyssey detection system (LI-COR Biosciences).

Animal Studies.

All animal studies were reviewed and approved by the Institutional Animal Care and Use Committee (IACUC) at the Dana-Farber Cancer Institute. The genetically engineered mouse model (GEMM) harboring a conditional activating mutation of endogenous Kras ($Kras^{LSL-G12D/+}$) crossed with p53 conditional knockout $Trp53^{fl/fl}$ has been previously described (36). CRE recombinase was induced through intranasal inhalation of 5×106 adeno-Cre (University of Iowa adenoviral core).

For drug treatment studies in GEMM models, mice were evaluated by MRI imaging to quantify lung tumor burden before and after drug treatment. Mice were treated with either vehicle, or 100 mg/kg trilaciclib or 100 mg/kg palbociclib daily by oral gavage.

For allograft studies, lung tumor nodules were isolated from $Kras^{LSL-G12D}Trp53^{fl/fl}$ mice (C57BL/6 background), minced into small pieces and plated onto tissue culture plates and passaged for at least 5 times before implantation into mice.

For syngeneic models, MC38 and CT26 cells were injected into 6-8 week C57BL/6 or Balb/c female mice subcutaneously, respectively. Vehicle control, CDK4/6 inhibitors (trilaciclib or palbociclib) were treated alone or together with PD-1 antibody starting at the indicated time point, using an intermittent dosing schedule of 3 days on, 4 days off until experimental endpoint. PD-1 antibody was administered 3 times a week (Monday, Wednesday and Friday) at 200 µg/mouse through I.P. injection.

Patient Samples.

Samples from human subjects treated at Massachusetts General Hospital and the Dana-Farber Cancer Institute were assembled for PDOTS profiling and culture between June and October 2016. Studies were conducted according to the Declaration of Helsinki and Informed consent was obtained from all subjects. Tumor samples were collected and analyzed according to Dana-Farber/Harvard Cancer Center IRB-approved protocols.

Flow Antibodies.

Lung infiltrating immune cells were stained with different combinations of fluorochrome-coupled antibodies against mouse CD45 (clone 30-F11, Biolegend), CD3 (clone 17A2, Biolegend), CD4 (clone GK1.5, Biolegend), CD8 (clone 53-6.7, Biolegend), CD11b (clone M1/70, Biolegend), CD11c (clone N418, Biolegend), Foxp3 (clone FJK-16s, eBioscience), CD279 (PD-1, clone 29F.1A12, Biolegend), CD152 (CTLA-4, clone UC10-4B9, eBioscience), Tim-3 (clone RMT3-23, eBioscience), CD223 (Lag-3, clone C9B7W, Biolegend), IL-2 (clone JES6-5H4, Biolegend), IFNγ (clone XMG1.2, Biolegend), BrdU (clone Bu20a, Biolegend). BrdU (clone Bu20a, Biolegend). Jurkat, PD-1-Jurkat, and human PBMCs were stained with fluorochrome-coupled antibodies against human CD3 (clone HIT3a, Biolegend), CD4 (clone OKT4, Biolegend), and CD279 (PD-1, clone EH12.2H7, Biolegend).

MRI Quantification.

Animals were anesthetized with isoflurane to perform magnetic resonance imaging (MRI) of the lung field using BioSpec USR70/30 horizontal bore system (Bruker) to scan 24 consecutive sections. Tumor volumes within the whole lung were quantified using 3D slicer software to reconstruct MRI volumetric measurements as previously described (36). Acquisition of the MRI signal was adapted according to cardiac and respiratory cycles to minimize motion effects during imaging.

Spheroid Preparation and Microfluidic Culture.

Experiments were performed as described (28). Briefly, fresh tumor specimens from human patients were received in media (DMEM) on ice and minced in 10 cm dishes (on ice) in a sterile field. S2 fractions (40-100 µm) were used for ex vivo culture as previously described (28). An aliquot of the S2 fraction was pelleted and re-suspended in type I rat-tail collagen (Corning, Corning, NY) and the spheroid-collagen mixture was then injected into the center gel region of the 3D microfluidic culture device. After 30 minutes at 37° C., collagen hydrogels containing PDOTS/MDOTS were hydrated with media with indicated treatments. MDOTS were treated with IgG isotype control (10 µg/mL, clone 2A3) or rat-α-mouse anti-PD-1 (10 µg/ml, clone RMP1-14, BioXCell). Both MDOTS and PDOTS were treated with vehicle (DMSO), palbociclib (palb) (100 nM) or trilaciclib (100 nM).

Live/Dead Staining.

Dual labeling was performed by loading microfluidic device with Nexcelom ViaStain™ AO/PI Staining Solution (Nexcelom, CS2-0106). Following incubation with the dyes (20 minutes at room temperature in the dark), images were captured on a Nikon Eclipse 80i fluorescence microscope equipped with Z-stack (Prior) and CoolSNAP CCD camera (Roper Scientific). Image capture and analysis was performed using NISElements AR software package. Whole device images were achieved by stitching in multiple captures. Live and dead cell quantification was performed by measuring total cell area of each dye.

Cytokine Profiling Analysis of Murine BAL Fluid.

Mouse lung broncho alveolar lavage (BAL) was performed by intracheal injection of 2 ml of sterile PBS followed by collection by aspiration. Cytokines were measured using 19-plex mouse magnetic Luminex kit (R&D systems), Mouse Cytokine 23-plex Assay (Bio-Rad) or Human Cytokine 40-plex Assay (Bio-Rad) and measured on Bio-Plex 200 system (Bio-Rad). Concentrations [pg/ml] of each protein were derived from 5-parameter curve fitting models. Fold changes relative to the control were calculated and plotted as log 2FC. Lower and upper limits of quantitation (LLOQ/ULOQ) were derived from standard curves for cytokines above or below detection. Mouse IL-6 and IL-10 concentrations were further confirmed by ELISA (Biolegend).

Tumor-Infiltrating Immune Cells Isolation and FACS Analysis.

Mice were sacrificed, and lungs were perfused using sterile PBS through heart perfusion from the left ventricle after BAL fluid collection. The whole lung was minced into small pieces and digested in collagenase D (Sigma) and Dnase I (Sigma) in Hank's Balanced Salt Solution (HBSS) at 37° C. for 30 min. After incubation, the digested tissue was filtered through a 70 µm cell strainer (Fisher) to obtain single-cell suspensions. Separated cells were treated with 1×RBC lysis buffer (Biolegend) to lyse red blood cells. Live cells were determined by LIVE/DEAD® fixable aqua dead cell stain kit (Molecular Probes). The cell pellets were re-suspended in PBS with 2% FBS for Fluorescence-activated cell sorting (FACS) analysis. Cells were stained with fpr cell surface markers as indicated followed by fixation/permeabilization using foxp3 fixation/permeabilization kit (eBioscience). Cells were imaged on BD LSRFortessa (BD Biosciences) and analyzed using FlowJo software (Tree Star).

Single-Cell RNA-Sequencing.

Library preparation and pre-processing: Single-cell suspensions from KrasG$^{12D/+}$Trp53$^{fl/fl}$ GEMM mice treated with trilaciclib were isolated as described for tumor-infiltrating immune cells, with modifications. After isolation, live cells were stained and sorted for the CD45+CD3+ DAPI-population and plated at one cell/well of a skirted twin.tec 96-well plate (Eppendorf) containslxTCL buffer (Qiagen cat #1031576) spiked with ERCC (Ambion, 1:2,000,000 dilution ratio). A total of four 96-well plates were generated, two plates with and two plates without ERCC spike-ins. After sorting, full-length RNA-seq from isolated single cells was performed according to SMART-seq2 protocol with modifications. Briefly, total RNA was purified using RNA-SPRI beads. Poly(A)+ mRNA was converted to cDNA for amplification. The converted cDNA transcript was subject to barcoding specific to each sample using transposon-based fragmentation that used dual-indexing. For single-cell sequencing, each cell was given its own combination of barcodes. Barcoded cDNA fragments were then pooled prior to sequencing. Sequencing was carried out as paired-end (PE) 2×36 bp with an additional 8 cycles for each index on NexSeq 500 desktop sequencer (Illumina). To obtain quantitative mapping information, PE reads were mapped to the mouse genome (mm9), concatenated with ERCC sequences for spiked-in samples, by STAR (56). Estimated transcript counts and transcripts per million (TPM) for the mouse Gencode vM1 annotation, concatenated with ERCC sequence information for spiked-in samples, were obtained using the pseudo-aligner Kallisto (57). Aggregated and library scaled TPM values for genes were obtained according to the methods described (58) and were used in further downstream differential distribution, Gene Ontology and cell cycle analysis. Only cells that had a minimum of 100,000 PE reads, and with at least 20% alignment to the transcriptome, were retained for further analysis. To further exclude cells that displayed low-quality we collected quality metrics for library size, library complexity, duplicate reads, mitochondrial and ribosomal read fraction and performed principal component analysis (PCA) combined with density based clustering (dbscan, http://citeseerx.ist.psu.edu/viewdoc/summary?doi=10.1.1.71.1980) to identify and remove outlier cells relative to the largest and homogeneous group of single-cells (27 cells removed). Genes were considered not expressed if TPM<1 and were subsequently removed if not detected in at least 10% of remaining cells. The single-cell RNA-seq results have been deposited in NCBI's Gene Expression Omnibus and are accessible through GEO Series accession number GSE-89477 (https://www.ncbi.nlm.nih.gov/geo/query/acc.cgi?acc=GSE89477).

Single-Cell RNA-Seq Analysis

Normalization:

We used a multi-step approach using the R package SCONE to identify the optimal normalization strategy and account for possible batch effects, observed and hidden technical covariates (59). First, we identified the most stable 200 genes between the two plates that contained spike-ins. Next, these genes were used in the SCONE framework as negative control genes for unwanted variation for all plates. We continued with highest scored normalization strategy according to SCONE metrics, which included adjusting for batch and biological effects, removal of observed technical variation based on previously identified quality metrics, scaling for library size with DESeq, and imputing drop-out events using a combined clustering and probabilistic scoring algorithm.

Cell-Cycle Classification:

To assign cells to a cell-cycle stage we applied the cyclone classification tool as previously described (60).

Feature Selection and Cell Clustering:

To identify the most informative genes for clustering single cells we continued only with the Gencode defined gene types, protein_coding and lincRNA, which contain most genes and displayed the highest coefficient of variation. Subsequently, we combined two approaches. First, we identified genes that displayed more than expected variance modeled by the relationship between variance and log expression with LOESS. Next, these genes were used to perform PCA and the 100 most correlated and anti-correlated genes for the first 5 principal components were retained for reducing dimensionality and separating cells in gene expression space with t-SNE. Distinct groups were identified applying density based clustering (dbscan) on the t-SNE generated coordinates, resulting in three (3) groups of cells.

Differential Distribution & Gene Ontology Analysis:

Genes that display differential distribution between previously identified groups or between treatments were discovered by performing pairwise comparisons with the scDD (http://biorxiv.org/content/early/2015/12/29/035501) package in R. Enriched biological processes were identified using the online GOrilla tool (http://bmcbioinformatics.biomedcentral.com/articles/10.1186/1471-2105-10-48).

BrdU Incorporation.

C57BL/6 mice were subjected to tail vein injection with the KrasG$^{12D/+}$Trp53$^{fl/fl}$ (KP) tumor cell line (1×10$^6$ cells/mouse) to induce orthotopic tumor growth in the lung. Tumor bearing mice or C57BL/6 background naïve mice were treated with vehicle (10 ug/g), palbociclib (100 mg/kg) or trilaciclib (100 mg/kg) by daily oral gavage for two consecutive days. At day 3, mice received an intraperitoneal injection of BrdU (BD Bioscience) at 2 mg/mouse in sterile PBS. Mice were sacrificed 24 hrs after BrdU injection, and splenocytes were isolated and stained for surface markers. Cells were fixed and permeabilized with foxp3 fixation/permeabilization buffer (eBioscience), followed by DNase I digestion (0.3 mg/ml, Roche) at 37° C. for 1 hr. Cells were stained with fluorochome-conjugated anti-BrdU antibody (Biolegend) and analyzed on LSRFortessa (BD Bioscience).

Cell Co-Culture and Cytokine Production.

Naïve or KP tumor bearing C57BL/6 mice were sacrificed and total splenocytes were harvested. Spleens were digested with collagenase D (Roche) and Dnase I (Roche) at 37° C. for 30 min, followed by 1×ACS lysis buffer (Biolegend) incubation to lyse red blood cells. The collected total splenocytes were stained with the fluorochome-conjugated cell surface markers CD3, CD4, CD8 and CD25 to isolate different T cell subpopulations, including conventional T cell Tconv (CD3+CD4+CD25), Treg (CD3+CD4+CD25+), and CD8+(CD3+CD8+) using BD FACSAria II SORP cell sorter (BD Bioscience). DAPI (4',6-diamidino-2-phenylindole) staining was used to exclude dead cells. Sorted cells were cultured in 96-well plates pre-coated with CD3 antibody (eBioscience) and treated with trilaciclib in the presence of CD28 (eBioscience). Cells were collected 3 days after culturing and cytokine production of IFNγ and IL-2 was determined by intracellular staining and analyzed on BD LSRFortessa (BD Bioscience).

Transient Transfection.

siRNA targeting human CDK4 or CDK6 (GE Dharmacon) or constructs for NFAT-Firefly Luciferase or *Renilla Luciferase*-SV40 (Addgene) were electroporated into cells using the Neon™ transfection system (Invitrogen) according to the manufacturer's recommended protocol.

Quantitative RT-PCR.

Total RNA was extracted from cells using Trizol (Invitrogen), and cDNA was generated using the SuperScript II Reverse Transcriptase Kit (Invitrogen). Quantitative PCR was performed using Power SYBR Green PCR Master Mix (Applied Biosystems), and transcript levels were normalized to Actin. Samples were run in triplicate. Primer sequences are listed below:

Oligonucleotides Used for Quantitative RT-PCR

|  | Forward Primer (5'-3') | Reverse Primer (5'-3') |
|---|---|---|
| Il-3 | CAACCTCAATGGGGAAGACCA (SEQ ID NO: 1) | TGGATTGGATGTCGCGTGG (SEQ ID NO: 2) |
| GM-CSF | TGCTGAGATGAATGAAACAGTAGA (SEQ ID NO: 3) | CTGGGTTGCACAGGAAGTT (SEQ ID NO: 4) |
| Actin | CGCACCACTGGCATTGTCAT (SEQ ID NO: 5) | TTCTCCTTGATGTCACGCAC (SEQ ID NO: 6) |

Luciferase Assay.

Luminescence was measured using the Dual-Glo Luciferase Assay System (Promega) from cells transiently transfected with NFAT-Firefly Luciferase and *Renilla Luciferase*-SV40 on a Clariostar Microplate Reader (BMG Labtech). Samples were run in triplicate.

Statistical Analysis.

Figure 7B:
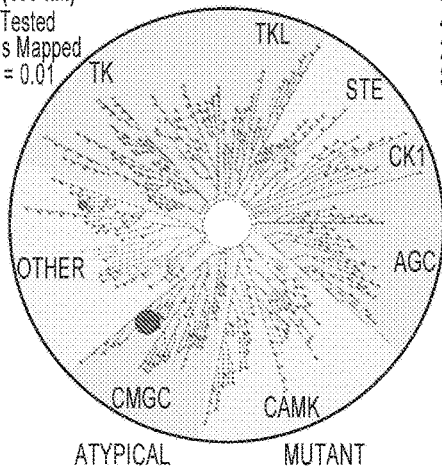
FIG. 7. Characterization of cells and CDK4/6 inhibitors. A. FACS plot for PD-1 from wild type and PD-1-overexpressing Jurkat cells, or CD3+CD4+ cells from PBMCs from two human donors. B. Kinome binding specificity of palbociclib and abemaciclib at 100 nM and 1000 nM measured by competition binding assays. CDK4 is indicated in blue. C. IC50 values of GSK3α/β by CDK4/6 inhibitors. D. Immunoblot for active (non-phosphorylated) or total β-catenin from lysates from PD-1-Jurkat cells treated as indicated for 6 h. E. Representative bright-field microscopy images of patient-derived organotypic tumor spheroid (PDOTS) cultured in a three-dimensional culturing system after treatment with different drugs as indicated. Photos were taken one day after the treatment. F. Percentages of subpopulations within total tumor infiltrating leukocytes (percentage in CD45+ cells). G. Percentage of subpopulations among all live cells, including tumor cells and other stromal cells (% in live cells).
Figure 7B:
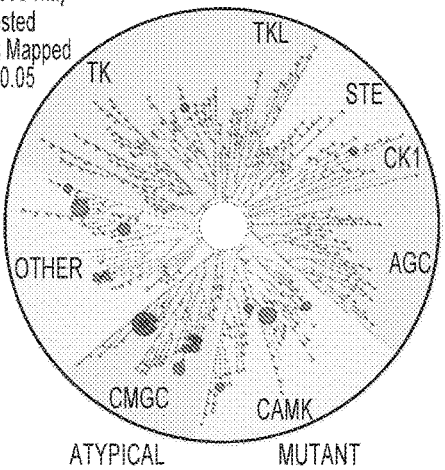
Figure 7B:
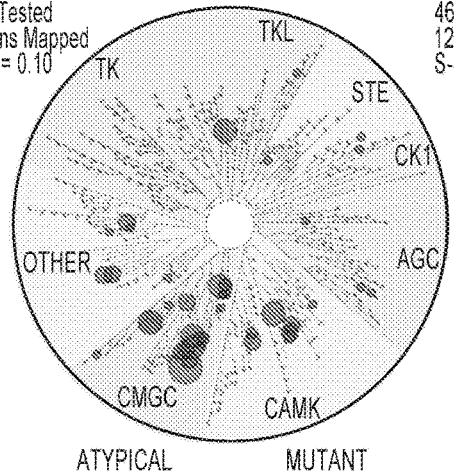
Figure 7B:
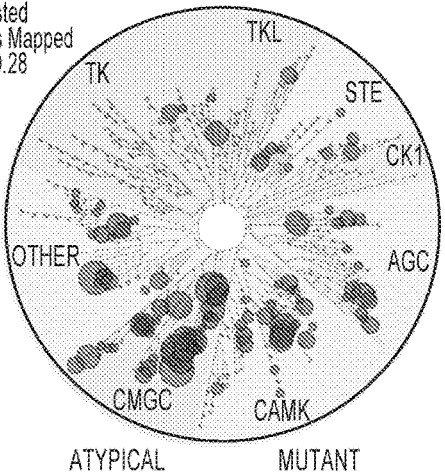

Data are presented as mean with SEM unless otherwise specified. Statistical comparisons were performed using unpaired student's t tests for two tailed p value unless otherwise specified. *$p<0.05$, $p<0.01$, *$p<0.001$ Example 2: Small Molecule Screen Identifies CDK4/6 Inhibitors as Compounds that Enhance T Cell Activity To identify small molecules capable of enhancing T cell activation in the setting of PD-1 engagement, we screened for compounds that activate PD-1-overexpressing Jurkat T cells (23), by measuring IL-2 secretion following α-CD3/CD28/IgG ("TCR/IgG") or α-CD3/CD28/PD-1 ("TCR/PD-1") stimulation (FIG. 1A, FIG. 7A). In addition to known negative regulators of IL-2 production (e.g. glycogen synthase kinase-3α/β (GSK3α/β) (24,25)), this screen identified cyclin-dependent kinases 4 and 6 inhibitors (CDK4/6i) as top hits (Table 1).

TABLE 1

Chemical compound screen

| Rank | Vendor ID | Chemical_Name | Zscore_1 | Zscore_2 | Zscore_AVG |
|---|---|---|---|---|---|
| 1 | 361551 | GSK-3 Inhibitor X | 28.58131895 | 35.88506376 | 32.23319136 |
| 2 | 361550 | GSK-3 Inhibitor IX | 25.07310783 | 34.87811704 | 29.97561243 |
| 3 | 402081 | Indirubin Derivative E804 | 20.77871321 | 24.42841897 | 22.60356609 |
| 4 | 559396 | SB 220025 | 14.68871072 | 27.59428311 | 21.14149692 |
| 5 | 402086 | Indirubin-3'-monoxime, 5-Iodo- | 10.18410723 | 17.15889851 | 13.67150287 |
| 6 | 420320 | KT5720 | 10.81165121 | 13.16795621 | 11.98980371 |
| 7 | 219476 | Cdk4 Inhibitor | 7.007165851 | 16.06784954 | 11.5375077 |
| 8 | 124029 | Akt Inhibitor XII, Isozyme- Selective, Akti-2 | 5.536359655 | 15.29263053 | 10.41449509 |
| 9 | 572650 | SU9516 | 8.231471836 | 12.12436026 | 10.17791605 |
| 10 | 420126 | JAK3 Inhibitor VI | 8.225984059 | 11.46660578 | 9.846294921 |
| 11 | 234501 | Compound 401 | 2.82873617 | 15.49439266 | 9.161564418 |
| 12 | 189405 | Aurora Kinase Inhibitor III | 7.107982711 | 6.482219515 | 6.795101113 |
| 13 | 260962 | DNA-PK Inhibitor III | 5.180394179 | 6.230482834 | 5.705438507 |
| 14 | 440206 | LY 294002, 4-NH2 | 3.329909189 | 7.539513571 | 5.43471138 |
| 15 | 361553 | GSK-3b Inhibitor XI | 5.720118968 | 4.871104761 | 5.295611865 |
| 16 | 181305 | Arcyriaflavin A, Synthetic | 3.889056716 | 5.674172464 | 4.78161459 |
| 17 | 375670 | Herbimycin A, *Streptomyces* sp. | 5.643015427 | 3.662768697 | 4.652892062 |
| 18 | 124020 | Akt Inhibitor X | 2.250459611 | 6.381524843 | 4.315992227 |
| 19 | 448101 | Met Kinase Inhibitor | 3.40701273 | 4.720062753 | 4.063537742 |
| 20 | 124012 | Akt Inhibitor V, Triciribine | 4.04594271 | 3.405939069 | 3.72594089 |
| 21 | 197221 | Bcr-abl Inhibitor | 1.402320657 | 5.27388345 | 3.338102053 |
| 22 | 567805 | Src Kinase Inhibitor I | 4.691053842 | 1.807555017 | 3.249304429 |
| 23 | 401488 | IKK-3 Inhibitor IX | 3.753978666 | 2.454432632 | 3.104205649 |
| 24 | 524611 | PIKfyve Inhibitor | 1.632132695 | 4.429038317 | 3.030585506 |
| 25 | 371957 | Isogranulatinude | 1.389866339 | 4.572493795 | 2.981180067 |
| 26 | 118500 | ATM Kinase Inhibitor | 1.378880809 | 4.382140783 | 2.880510796 |
| 27 | 528113 | PI 3-Kβ Inhibitor VI, TGX- 221 | 2.503815933 | 2.527882748 | 2.515849341 |
| 28 | 521232 | PDGF Receptor Tyrosine Kinase Inhibitor III | 1.681207003 | 3.032397162 | 2.356802082 |
| 29 | 220486 | Chk2 Inhibitor II | 2.673190261 | 1.941636498 | 2.307413379 |
| 30 | 343022 | Flt-3 Inhibitor III | 1.171010033 | 3.36068468 | 2.265847357 |
| 31 | 324673 | EGFR/ErbB-2 Inhibitor | 0.091560455 | 4.015200049 | 2.053380252 |
| 32 | 402085 | Indirubin-3'-monoxime | 2.084867783 | 1.884212868 | 1.984540325 |
| 33 | 343021 | Flt-3 Inhibitor II | 1.535766803 | 2.085195573 | 1.810481188 |
| 34 | 343020 | Flt-3 Inhibitor | 1.516156053 | 2.085195573 | 1.800675813 |
| 35 | 324674 | EGFR Inhibitor | 2.026035535 | 1.568382901 | 1.797209218 |
| 36 | 328009 | ERK Inhibitor III | 0.97825118 | 2.555127304 | 1.766689242 |
| 37 | 218714 | Keratinocyte Differentiation Inducer | 1.986814036 | 1.424823826 | 1.705818931 |
| 38 | 420129 | JNK Inhibitor V | −0.378824725 | 3.625680531 | 1.623427903 |
| 39 | 528106 | PI 3-Kg Inhibitor | 0.895725752 | 2.230374904 | 1.563050328 |
| 40 | 572635 | SU6656 | 1.732620061 | 1.332980189 | 1.532800125 |
| 41 | 475880 | ML-7, Hydrochloride | 2.905839712 | 0.088107838 | 1.496973775 |
| 42 | 361556 | GSK-3 Inhibitor IX, Control, MeBIO | 1.104330319 | 1.769365607 | 1.436847963 |
| 43 | 124018 | Akt Inhibitor VIII, Isozyme- Selective, Akti-1/2 | 1.673042048 | 1.051570229 | 1.362306138 |

TABLE 1-continued

Chemical compound screen

| Rank | Vendor ID | Chemical_Name | Zscore_1 | Zscore_2 | Zscore_AVG |
|---|---|---|---|---|---|
| 44 | 203696 | BPIQ-I | 0.653283085 | 1.970348313 | 1.311815699 |
| 45 | 218710 | Casein Kinase II Inhibitor III, TBCA | 1.01680295 | 1.548180583 | 1.282491767 |
| 46 | 495621 | Olomoucine II | 0.34446749 | 2.103028505 | 1.223747997 |
| 47 | 189404 | Aurora Kinase Inhibitor II | −0.602371416 | 2.957905992 | 1.177767288 |
| 48 | 191500 | 1-Azakenpaullone | 0.417954094 | 1.912924683 | 1.165439388 |
| 49 | 559399 | SB 203580, Sulfone | 2.850036485 | −0.644800328 | 1.102618079 |
| 50 | 528108 | PI 3-KbInhibitor II | −0.12391463 | 2.314938882 | 1.095512126 |
| 51 | 371806 | GTP-14564 | −0.563819646 | 2.60547464 | 1.020827497 |
| 52 | 528111 | PI 3-Kα Inhibitor IV | 1.287040223 | 0.722252214 | 1.004646218 |
| 53 | 189405 | Aurora Kinase Inhibitor III | 2.736743109 | −0.813928283 | 0.961407413 |
| 54 | 506158 | p38 MAP Kinase Inhibitor VII, SD-169 | 0.755771955 | 1.067446287 | 0.911609121 |
| 55 | 219448 | Cdk2/5 Inhibitor | 0.614061587 | 1.108993859 | 0.861527723 |
| 56 | 361549 | GSK-3b Inhibitor VIII | 1.01680295 | 0.591581198 | 0.804192074 |
| 57 | 220485 | Chk2 Inhibitor | −0.872233811 | 2.454432632 | 0.791099411 |
| 58 | 572660 | SU11652 | 8.033208428 | −6.691124712 | 0.671041858 |
| 59 | 559285 | RSK Inhibitor, SL0101 | 1.688779383 | −0.348826407 | 0.669976488 |
| 60 | 513035 | PD 158780 | 0.378742862 | 0.881572555 | 0.630157708 |
| 61 | 218697 | Casein Kinase II Inhibitor I | 0.633672336 | 0.534757557 | 0.584214946 |
| 62 | 529574 | PP3 | 0.241641373 | 0.908125945 | 0.574883659 |
| 63 | 420123 | JNK Inhibitor, Negative Control | 0.102672122 | 1.04647922 | 0.574575671 |
| 64 | 420121 | JAK3 Inhibitor IV | 0.202235852 | 0.908011153 | 0.555123503 |
| 65 | 420119 | JNK Inhibitor II | 0.442552249 | 0.581377345 | 0.511964797 |
| 66 | 121790 | AGL 2043 | −0.248811381 | 1.252552935 | 0.501870777 |
| 67 | 116890 | Adenosine Kinase Inhibitor | 0.398343345 | 0.592181187 | 0.495262266 |
| 68 | 559404 | SB 239063 | −0.083974662 | 1.040892896 | 0.478459117 |
| 69 | 422709 | KN-92 | 0.53561859 | 0.391198481 | 0.463408535 |
| 70 | 406170 | IP3K Inhibitor | 1.006276572 | −0.096902376 | 0.454687098 |
| 71 | 121767 | AG 1024 | 0.339511097 | 0.506045742 | 0.422778419 |
| 72 | 344036 | cFMS Receptor Tyrosine Kinase Inhibitor | −0.209589883 | 1.022858414 | 0.406634265 |
| 73 | 324840 | EGFR/ErbB-2/ErbB-4 Inhibitor | 0.457175593 | 0.333774851 | 0.395475222 |
| 74 | 217696 | Cdk1 Inhibitor, CGP74514A | 1.59507951 | −1.019533555 | 0.287772978 |
| 75 | 420136 | JNK Inhibitor IX | 0.584168969 | −0.052852486 | 0.265658242 |
| 76 | 203303 | Bisindolylmaleimide V | −0.621415618 | 1.108993859 | 0.243789121 |
| 77 | 513040 | PD 174265 | −0.118250034 | 0.589485263 | 0.235617614 |
| 78 | 440203 | LY 303511 | 1.209561804 | −0.868491547 | 0.170535129 |
| 79 | 220285 | Chelerythrine Chloride | 0.182625103 | 0.075368515 | 0.128996809 |
| 80 | 317200 | DMBI | −0.21685371 | 0.44053919 | 0.11184274 |
| 81 | 506106 | p21-Activated Kinase Inhibitor III, IPA-3 | −0.461003755 | 0.642592043 | 0.090794144 |
| 82 | 260961 | DNA-PK Inhibitor II | 0.064960607 | 0.10408033 | 0.084520468 |
| 83 | 528100 | PI-103 | −0.718026728 | 0.843317879 | 0.062645575 |
| 84 | 218696 | Casein Kinase I Inhibitor, D4476 | −1.219199746 | 1.296443903 | 0.038622078 |
| 85 | 521231 | PDGF Receptor Tyrosine Kinase Inhibitor II | −0.70093136 | 0.775358994 | 0.037213817 |
| 86 | 506121 | p38 MAP Kinase Inhibitor III | −0.70093136 | 0.642592043 | −0.029169658 |
| 87 | 676485 | VEGF Receptor 2 Kinase Inhibitor II | 0.121677571 | −0.180563053 | −0.029442741 |
| 88 | 513030 | PD 169316 | −0.169663092 | 0.084970849 | −0.042346122 |
| 89 | 480065 | Necrostatin-1 | −1.566165682 | 1.447485911 | −0.059339886 |
| 90 | 565715 | Scytonemin, Lyngbya sp. | 0.121677571 | −0.339883395 | −0.109102912 |
| 91 | 539652 | PKCbII/EGFR Inhibitor | −0.838032848 | 0.616038653 | −0.110997098 |
| 92 | 528282 | Polo-like Kinase Inhibitor I | −0.888644916 | 0.623659333 | −0.132492792 |
| 93 | 676489 | VEGF Receptor 2 Kinase Inhibitor IV | −1.794991923 | 1.511581096 | −0.141705413 |
| 94 | 658551 | AG 1296 | 0.527522281 | −0.856210271 | −0.164343995 |
| 95 | 407248 | IGF-1R Inhibitor II | 0.51600784 | −0.986968645 | −0.235480402 |
| 96 | 371964 | HA 1004, Dihydrochloride | 0.084571356 | −0.671138679 | −0.293283661 |
| 97 | 238900 | 4-Cyano-3-methylisoquinoline | −0.756578499 | 0.138455174 | −0.309061662 |
| 98 | 506153 | p38 MAP Kinase Inhibitor IV | −0.649518302 | 0.005310678 | −0.322103812 |
| 99 | 266788 | Diacylglycerol Kinase Inhibitor II | −0.987889123 | 0.339844518 | −0.324022302 |
| 100 | 238811 | Cdk9 Inhibitor II | −0.795130269 | 0.138455174 | −0.328337548 |
| 101 | 574713 | Syk Inhibitor III | −0.889445907 | 0.19118441 | −0.349130748 |
| 102 | 219477 | Cdk4 Inhibitor II, 625987 | 0.574840088 | −1.274086796 | −0.349623354 |
| 103 | 526523 | PIM1/2 Kinase Inhibitor V | −0.91696826 | 0.200839446 | −0.358064407 |
| 104 | 328008 | ERK Inhibitor II, Negative Control | −1.778449825 | 1.051570229 | −0.363439798 |
| 105 | 440202 | LY 294002 | −1.45051037 | 0.69227587 | −0.37911725 |
| 106 | 528114 | PI 3-Kγ Inhibitor VII | −0.083974662 | −0.685077467 | −0.384526065 |
| 107 | 559389 | SB 203580 | −0.820895162 | −0.021242712 | −0.421068937 |
| 108 | 219445 | Cdk2 Inhibitor II | −0.209589883 | −0.642426863 | −0.426008373 |
| 109 | 529581 | PP1 Analog II, 1NM-PP1 | −0.975134337 | 0.084970849 | −0.445081744 |
| 110 | 681641 | Wee1 Inhibitor II | 0.754109033 | −1.786414023 | −0.516152495 |
| 111 | 401787 | IKK-2 Inhibitor VIII | −0.679474957 | −0.365018186 | −0.522246572 |
| 112 | 569615 | Stem-Cell Factor/c-Kit Inhibitor, ISCK03 | −0.975134337 | −0.074349493 | −0.524741915 |
| 113 | 616453 | TGF-b RI Inhibitor III | −0.409590697 | −0.658524077 | −0.534057387 |
| 114 | 422706 | KN-62 | −0.248811381 | −0.843409569 | −0.546110475 |
| 115 | 506157 | p38 MAP Kinase Inhibitor VI, JX401 | −0.375315325 | −0.924057979 | −0.649686652 |
| 116 | 208922 | CaMKII Inhibitor, CK59 | −0.83368204 | −0.516060194 | −0.674871117 |
| 117 | 217695 | Cdk1 Inhibitor | −0.778301612 | −0.613715048 | −0.69600833 |
| 118 | 528112 | PI 3-K&gamme;/CKII Inhibitor | −0.820895162 | −0.578863907 | −0.699879534 |
| 119 | 574712 | Syk Inhibitor II | −0.78661979 | −0.685077467 | −0.735848629 |

TABLE 1-continued

Chemical compound screen

| Rank | Vendor ID | Chemical_Name | Zscore_1 | Zscore_2 | Zscore_AVG |
|---|---|---|---|---|---|
| 120 | 676481 | VEGF Receptor Tyrosine Kinase Inhibitor II | −1.403576488 | −0.100902883 | −0.752239686 |
| 121 | 171260 | AMPK Inhibitor, Compound C | −2.876925884 | 1.296443903 | −0.79024099 |
| 122 | 234503 | Compound 52 | −1.4119586 | −0.264323514 | −0.838141057 |
| 123 | 565625 | SC-68376 | −1.403576488 | −0.286776614 | −0.845176551 |
| 124 | 658390 | AG 9 | 0.782432377 | −2.547489819 | −0.882528721 |
| 125 | 527455 | PKR Inhibitor, Negative Control | −1.426788452 | −0.433390384 | −0.930089418 |
| 126 | 400090 | IC261 | −0.78661979 | −1.136485101 | −0.961552446 |
| 127 | 420104 | JAK3 Inhibitor II | −0.778301612 | −1.360222242 | −1.069261927 |
| 128 | 526522 | PIM1 Kinase Inhibitor IV | −1.455111795 | −0.729364305 | −1.09223805 |
| 129 | 676487 | VEGF Receptor 2 Kinase Inhibitor III | −0.208884662 | −2.040105955 | −1.124495308 |
| 130 | 526520 | PIM1 Kinase Inhibitor II | −1.398465108 | −0.856210271 | −1.127337689 |
| 131 | 528283 | Polo-like Kinase Inhibitor II, BTO-1 | −1.794991923 | −0.517954362 | −1.156473142 |
| 132 | 526524 | PIM1/2 Kinase Inhibitor VI | −0.769482104 | −1.561339344 | −1.165410724 |
| 133 | 658552 | AG 1478 | −1.129373511 | −1.216145272 | −1.172759392 |
| 134 | 681637 | Wee1/Chk1 Inhibitor | −0.12391463 | −2.251515898 | −1.187715264 |
| 135 | 361554 | GSK-3b Inhibitor XII, TWS119 | −1.05858498 | −1.321312147 | −1.189948564 |
| 136 | 521233 | PDGF Receptor Tyrosine Kinase Inhibitor IV | −0.889445907 | −1.508232564 | −1.198839235 |
| 137 | 454861 | MNK1 Inhibitor | −2.021578675 | −0.391108396 | −1.206343535 |
| 138 | 559402 | SB 218078 | −0.87230822 | −1.561339344 | −1.216823782 |
| 139 | 658401 | AG 490 | −2.644692241 | 0.200839446 | −1.221926398 |
| 140 | 407601 | IRAK-1/4 Inhibitor | −0.503751122 | −1.963170359 | −1.233460741 |
| 141 | 422000 | Kenpaullone | −0.769482104 | −1.747213076 | −1.25834759 |
| 142 | 676480 | VEGF Receptor 2 Kinase Inhibitor I | −0.803757476 | −1.720659686 | −1.262208581 |
| 143 | 506163 | p38 MAP Kinase Inhibitor VIII | −1.143555012 | −1.448158113 | −1.295856563 |
| 144 | 616451 | TGF-b RI Kinase Inhibitor | −0.718069046 | −1.933086807 | −1.325577927 |
| 145 | 506126 | p38 MAP Kinase Inhibitor | −0.718069046 | −1.986193588 | −1.352131317 |
| 146 | 570250 | STO-609 | −1.710021891 | −1.025338226 | −1.367680059 |
| 147 | 540500 | Purvalanol A | −3.126189089 | 0.369967401 | −1.378110844 |
| 148 | 555553 | Rho Kinase Inhibitor III, Rockout | −0.180561318 | −2.589771808 | −1.385166563 |
| 149 | 555555 | Rho Kinase Inhibitor V | −0.61524293 | −2.172067319 | −1.393655124 |
| 150 | 361541 | GSK-3b Inhibitor II | −2.375752865 | −0.415365522 | −1.395559194 |
| 151 | 567305 | SKF-86002 | −0.495279127 | −2.331387661 | −1.413333394 |
| 152 | 118501 | ATM/ATR Kinase Inhibitor | −1.798060574 | −1.07310409 | −1.435582332 |
| 153 | 681640 | Wee1 Inhibitor | −0.662058165 | −2.20923391 | −1.435646037 |
| 154 | 559387 | SB 202474, Neg Con for p38 MAPK Inhibition Studies | −2.474752178 | −0.602518339 | −1.538635258 |
| 155 | 551590 | Quercetagetin | −1.426788452 | −1.659568057 | −1.543178254 |
| 156 | 676483 | VEGFR Tyrosine Kinase Inhibitor IV | −0.87230822 | −2.30483427 | −1.588571245 |
| 157 | 422708 | KN-93 | −0.289626894 | −2.889008855 | −1.589317875 |
| 158 | 234505 | Compound 56 | −1.072462851 | −2.221576695 | −1.647019773 |
| 159 | 655203 | TX-1918 | −0.973614948 | −2.336079876 | −1.654847412 |
| 160 | 658550 | AG 1295 | −0.237208006 | −3.097155673 | −1.667181839 |
| 161 | 513000 | PD98059 | −1.780605582 | −1.614446125 | −1.697525853 |
| 162 | 371958 | H-8, Dihydrochloride | −1.013630603 | −2.508694847 | −1.761162725 |
| 163 | 361540 | GSK-3b Inhibitor I | −1.327402592 | −2.221576695 | −1.774489643 |
| 164 | 444938 | MEK Inhibitor II | −2.219842082 | −1.363594136 | −1.791718109 |
| 165 | 555551 | Rho Kinase Inhibitor II | −1.74633021 | −1.879980027 | −1.813155118 |
| 166 | 371963 | H-89, Dihydrochloride | −3.267805808 | −0.433390384 | −1.850598096 |
| 167 | 219457 | Cdk Inhibitor, p35 | −1.994168067 | −1.733475838 | −1.863821953 |
| 168 | 557360 | Roscovitine | −1.540081827 | −2.20923391 | −1.874657869 |
| 169 | 475863 | MK2a Inhibitor | −1.454989547 | −2.30483427 | −1.879911908 |
| 170 | 219479 | Cdc2-Like Kinase Inhibitor, TG003 | −1.36662409 | −2.422559401 | −1.894591746 |
| 171 | 126870 | Alsterpaullone | −0.778301612 | −3.341337485 | −2.059819549 |
| 172 | 189406 | Aurora Kinase/Cdk Inhibitor | −1.131295099 | −3.054219334 | −2.092757216 |
| 173 | 557362 | Roscovitine, (S)-Isomer | −2.927925681 | −1.279030158 | −2.10347792 |
| 174 | 420135 | JNK Inhibitor VIII | −1.283612686 | −2.968669026 | −2.126140856 |
| 175 | 203297 | Bisindolylmaleimide IV | −2.072611064 | −2.336423956 | −2.20451751 |
| 176 | 559388 | SB 202190 | −1.511758483 | −3.097155673 | −2.304457078 |
| 177 | 128125 | Aloisine A, RP107 | −3.300995361 | −1.321617571 | −2.311306466 |
| 178 | 203600 | Bohemine | −1.700006828 | −3.082931149 | −2.391468988 |
| 179 | 128135 | Aloisine, RP106 | −0.872233811 | −4.241763061 | −2.556998436 |
| 180 | 371970 | HA 1077, Dihydrochloride Fasudil | −1.883431698 | −3.234202928 | −2.558817313 |
| 181 | 553210 | Rapamycin | −1.883431698 | −3.366969879 | −2.625200788 |
| 182 | 658440 | AG 112 | −1.540081827 | −3.815949481 | −2.678015654 |
| 183 | 553509 | Ras/Rac Transformation Blocker, SCH 51344 | −2.363286908 | −3.127989367 | −2.745638137 |
| 184 | 401481 | IKK-2 Inhibitor IV | −1.557815663 | −4.190124975 | −2.873970319 |
| 185 | 260964 | DNA-PK Inhibitor V | −2.219842082 | −4.111923401 | −3.165882742 |
| 186 | 217699 | Cdk1 Inhibitor IV, RO-3306 | −4.187686085 | −2.22786962 | −3.207777852 |
| 187 | 361555 | GSK-3 Inhibitor XIII | −2.534663768 | −3.924591073 | −3.229627421 |
| 188 | 616404 | Tpl2 Kinase Inhibitor II | −2.39756228 | −4.190124975 | −3.293843628 |
| 189 | 328007 | ERK Inhibitor II, FR180204 | −2.072611064 | −4.805640057 | −3.43912556 |
| 190 | 217720 | Cdk1/5 Inhibitor | −2.414304636 | −4.694889085 | −3.554596861 |
| 191 | 238803 | Cdk2 Inhibitor III | −2.414304636 | −4.745236421 | −3.579770529 |
| 192 | 164640 | Aminopurvalanol A | −3.686513067 | −3.637595029 | −3.662054048 |
| 193 | 688000 | ROCK Inhibitor, Y-27632 | −3.26886677 | −4.37496283 | −3.8219148 |
| 194 | 555550 | Rho Kinase Inhibitor | −3.271584269 | −4.508765658 | −3.890174963 |
| 195 | 567731 | Sphingosine Kinase Inhibitor | −3.805949343 | −4.15420539 | −3.980077367 |

TABLE 1-continued

Chemical compound screen

| Rank | Vendor ID | Chemical_Name | Zscore_1 | Zscore_2 | Zscore_AVG |
|---|---|---|---|---|---|
| 196 | 574711 | Syk Inhibitor | −3.580062618 | −4.614979219 | −4.097520918 |
| 197 | 196870 | BAY 11-7082 | −3.876799998 | −4.461098275 | −4.168949136 |
| 198 | 539654 | PKCb Inhibitor | −3.511511874 | −5.039833462 | −4.275672668 |
| 199 | 681500 | WHI-P180, Hydrochloride | −4.627326318 | −4.111923401 | −4.36962486 |
| 200 | 203294 | Bisindolylmaleimide III, Hydrochloride | −3.661081756 | −5.092758208 | −4.376919982 |
| 201 | 554717 | Reversine | −3.511511874 | −5.331920755 | −4.421716314 |
| 202 | 616373 | Tpl2 Kinase Inhibitor | −2.899602337 | −5.972330904 | −4.435966621 |
| 203 | 401486 | IKK Inhibitor VII | −6.153826388 | −3.033426996 | −4.593626692 |
| 204 | 521234 | PDGF RTK Inhibitor | −3.239482464 | −6.099176871 | −4.669329667 |
| 205 | 444937 | MEK Inhibitor I | −4.599002974 | −4.872999198 | −4.736001086 |
| 206 | 420099 | JAK Inhibitor I | −4.033685992 | −6.011536292 | −5.022611142 |
| 207 | 401489 | IKK Inhibitor X | −4.958721498 | −5.349404454 | −5.154062976 |
| 208 | 401490 | IKK-2 Inhibitor XI | −4.484733225 | −6.011536292 | −5.248134759 |
| 209 | 365250 | G? 6976 | −6.423688782 | −4.191415725 | −5.307552253 |
| 210 | 555554 | Rho Kinase Inhibitor IV | −5.703613388 | −5.042127153 | −5.372870271 |
| 211 | 365252 | G&omul; 7874, Hydrochloride | −4.465122476 | −6.384789888 | −5.424956182 |
| 212 | 238804 | Cdk2 Inhibitor IV, NU6140 | −4.843066186 | −6.15496183 | −5.499014008 |
| 213 | 420298 | K-252a, *Nocardiopsis* sp. | −4.419809235 | −6.579930095 | −5.499869665 |
| 214 | 407900 | 5-Iodotubercidin | −4.798505214 | −6.212518998 | −5.505512106 |
| 215 | 444939 | MEK 1/2 Inhibitor | −4.768943038 | −6.395150791 | −5.582046915 |
| 216 | 218713 | Keratinocyte Differentiation Inducer | −4.818115963 | −6.384789888 | −5.601452926 |
| 217 | 475864 | MK-2 Inhibitor III | −4.418996709 | −7.061213879 | −5.740105294 |
| 218 | 324515 | eEF-2 Kinase Inhibitor, NH125 | −4.759283715 | −7.332279788 | −6.045781751 |
| 219 | 124011 | Akt Inhibitor IV | −5.269163196 | −6.84417893 | −6.056671063 |
| 220 | 557520 | Ro-31-8220 | −5.986846828 | −6.268304825 | −6.127575827 |
| 221 | 126871 | Alsterpaullone, 2-Cyanoethyl | −5.269163196 | −7.447127048 | −6.358145122 |
| 222 | 401483 | IKK-2 Inhibitor VI | −5.575549828 | −7.212255887 | −6.393902858 |
| 223 | 539648 | Staurosporine, N-benzoyl- | −5.986846828 | −7.071662611 | −6.529254719 |
| 224 | 401482 | IKK-2 Inhibitor V | −5.484881438 | −7.79166883 | −6.638275134 |
| 225 | 481406 | NF-KB Activation Inhibitor | −6.213433579 | −7.832738407 | −7.023085993 |
| 226 | 219478 | Cdk4 Inhibitor III | −6.073203917 | −8.107498796 | −7.090351356 |
| 227 | 341251 | Fascaplysin, synthetic | −6.288922159 | −8.222346056 | −7.255634108 |
| 228 | 527450 | PKR Inhibitor | −7.657924121 | −8.08643034 | −7.87217723 |
| 229 | 539644 | UCN-01 | −7.459660713 | −8.297840283 | −7.878750498 |
| 230 | 444965 | MEK1/2 Inhibitor II | −8.274173773 | −7.766076583 | −8.020125178 |
| 231 | 569397 | Staurosporine, *Streptomyces* sp. | −6.893193834 | −9.439453978 | −8.166323906 |
| 232 | 203881 | CR8, (R)-Isomer | −9.662037515 | −6.960519207 | −8.311278361 |
| 233 | 569397 | Staurosporine, *Streptomyces* sp. | −7.431337369 | −9.650863922 | −8.541100645 |
| 234 | 428205 | Lck Inhibitor | −8.466932626 | −8.924065312 | −8.695498969 |
| 235 | 203290 | Bisindolylmaleimide I | −9.430726892 | −8.31989728 | −8.875312086 |
| 236 | 528116 | PI 3-Kα Inhibitor VIII | −7.657924121 | −10.32737574 | −8.992649931 |
| 237 | 365251 | G? 6983 | −9.777692827 | −9.07510732 | −9.426400074 |
| 238 | 217707 | Cdc7/Cdk9 Inhibitor | −9.816244598 | −10.33379072 | −10.07501766 |
| 239 | 521275 | PDK1/Akt/Flt Dual Pathway Inhibitor | −10.04755522 | −10.5855274 | −10.31654131 |
| 240 | 203882 | CR8, (S)-Isomer | −10.2017623 | −10.5855274 | −10.39364485 |
| 241 | 238806 | Cdk2/9 Inhibitor | −10.43307293 | −10.5855274 | −10.50930016 |
| 242 | 217714 | Cdk1/2 Inhibitor III | −10.54872824 | −11.64282146 | −11.09577485 |
| 243 | 219491 | Cdk/Crk Inhibitor | −10.43307293 | −11.89455814 | −11.16381553 |
| 244 | 570100 | Ste11 MAPKKK Activation Inhibitor | | | |

Figure 7C:
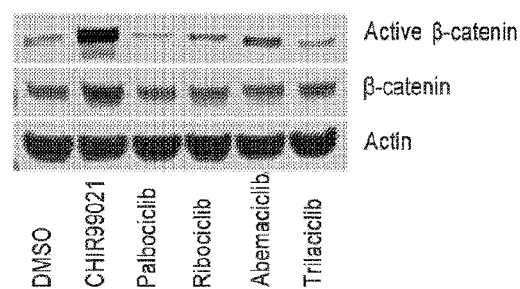

As immunostimulatory properties have not been previously ascribed to CDK4/6i, we tested several optimized inhibitors, including the three FDAapproved compounds palbociclib (palb), ribociclib, and abemaciclib, as well as trilaciclib (trila; G1T28), a recently reported selective CDK4/6 inhibitor (26, 27), and found that three of the four tested compounds potently enhanced IL-2 secretion, even when suppressed by PD-1 signaling (FIG. 1B). Although abemaciclib had the greatest stimulatory activity, kinome profiling revealed that it potently inhibits many other kinases, including GSK3α/β (FIGS. 7B-D and published data (26)). As palbociclib and trilaciclib are significantly more selective for CDK4/6, we sought to minimize potential confounding effects due to off-target activity and focused our studies on these two compounds.

To further investigate this phenomenon, we stimulated primary human CD4+ T cells with α-CD3/CD28 and either recombinant PD-L1 or control IgG, and found that both palbociclib and trilaciclib treatment enhanced IL-2 secretion (FIG. 1C). This recapitulated the effect we observed in Jurkat cells, confirming that CDK4/6i have potent immunostimulatory activity. Importantly, transfection of CDK4 or CDK6 specific siRNAs (FIG. 1D) revealed that knockdown of CDK6, but not CDK4, enhanced IL-2 secretion (FIG. 1E), supporting on-target specificity of small molecule CDK4/6 inhibitors and a predominant role for CDK6 inhibition.

Figure 1G:
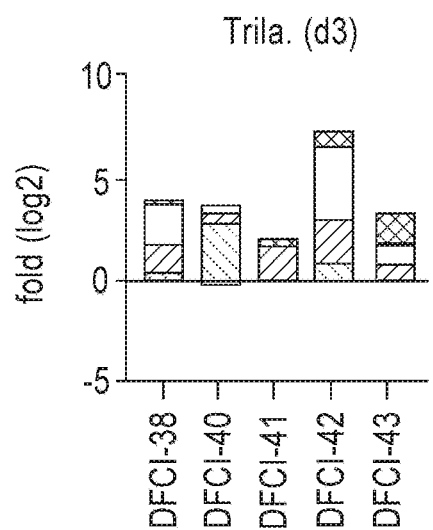
Figure 1G:
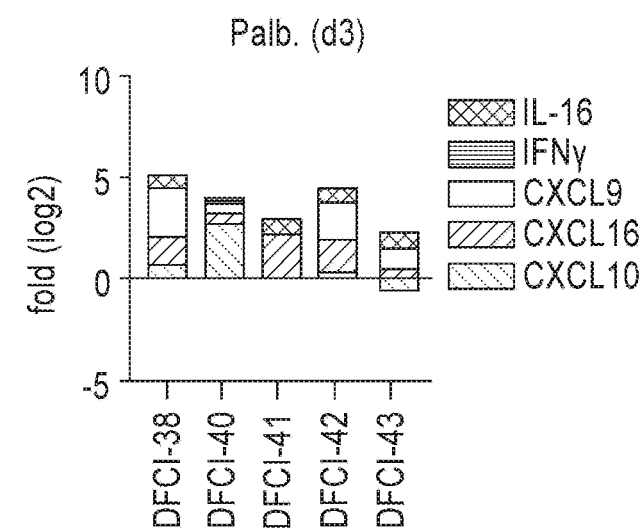
Figure 7E:
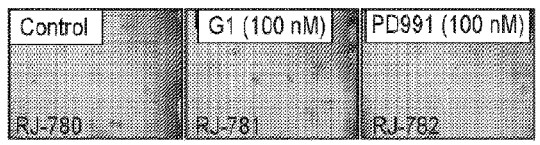
Figure 7F:
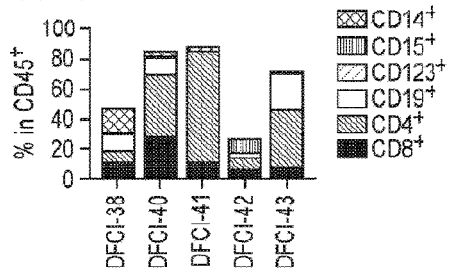
Figure 7G:
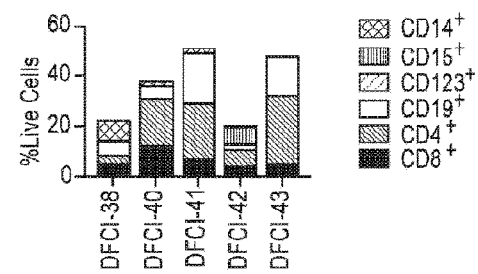

To verify this discovery in a more physiologic setting, patient-derived organotypic tumor spheroids (PDOTS) were treated with CDK4/6i (FIG. 7E) in a novel ex vivo 3D microfluidic culture system (28). PDOTS contain autologous tumor-infiltrating immune cells (FIG. 7F, 7G), and bead-based cytokine profiling of conditioned media from spheroids loaded into 3D microfluidic devices revealed increased levels of Th1 cytokines (e.g. CXCL9, CXCL10, IFNγ, IL-16 and CXCL16) (29,30) following treatment with palbociclib or trilaciclib (FIG. 1F, 1G). Although the concentration of IL-2 was below the detection range in this system, these findings suggest that CDK4/6i may activate CTL/Th1 responses to elicit anti-tumor immunity.

Example 3: CDK6 Regulates NFAT Activity

Figure 2A:
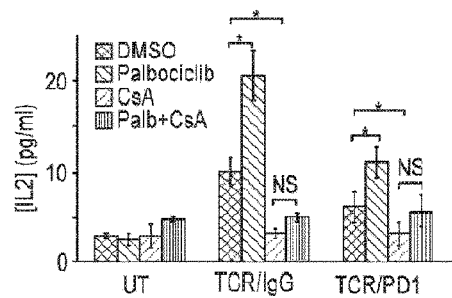
FIG. 2. CDK4/6 inhibition de-represses NFAT activity. A. Quantification of IL-2 levels from PD-1-Jurkat cells treated with 1 µM palbociclib and/or 1 µM cyclosporine A (CsA) and stimulated as indicated for 18 h. Results shown as mean±SD (UT, n=2; other conditions, n=4) (*p<0.05). B. Immunoblot for levels of phospho-S172 and total NFAT2 after treatment of PD-1-Jurkat cells with 1 µM palbociclib and stimulated as indicated for 18 h. C. Immunoblot for NFAT4 from nuclear and cytoplasmic fractions of PD-1-Jurkat cells treated with 1 µM palbociclib and stimulated as indicated for 18 h. D. Normalized luminescence of PD-1-Jurkat cells transiently transfected with NFAT-FLuc and RLuc-SV40 reporters after treatment with 1 µM palbociclib and stimulated as indicated for 18 h. Results shown as mean±SD (n=3) (*p<0.05). E. Relative levels of Il-2, Il-3, and GM-CSF mRNA as measured by qPCR from PD-1-Jurkat cells treated with 1 µM palbociclib and stimulated as indicated for 8 h. Results shown as mean±SD (n=3). *p<0.05 by two-way ANOVA with Bonferonni correction for multiple comparisons.
Figure 8A:
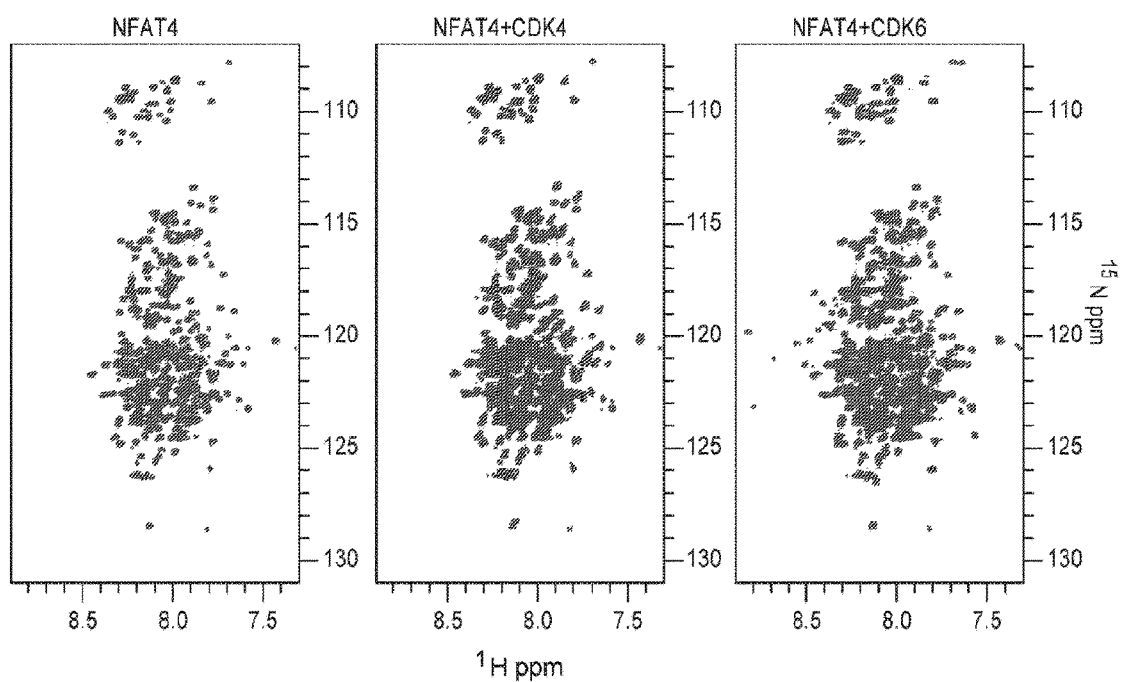
FIG. 8. CDK6 phosphorylates serine residues of the regulatory domain of NFAT4 (NFATc3). A. $^1$H-$^{15}$N-HSQC spectrum of NFATc3 (1-400) alone (red, left panel), overlaid with the spectrum after the addition of recombinant CDK4/cyclin D1 (teal, middle panel), or overlaid with the spectrum after the addition of recombinant CDK6/cyclin D3 (blue, right panel). B. $^1$H-$^{15}$N-HSQC spectrum of NFATc3 (red) overlaid with the spectrum of the same protein sample in the presence of 0.7% DMSO (navy, left panel), overlaid with the spectrum after CDK6-dependent phosphorylation in the presence of 0.7% DMSO (blue, middle panel), or overlaid with the spectrum in the presence of CDK6 pre-incubated with palbociclib (cyan, right panel). C. Intrinsic disorder prediction of NFATc3 (1-400) using the PONDR-Fit3, showing that most of the N-terminal regulatory domain of NFATc3 is unstructured, with a few structured elements.
Figure 8B:
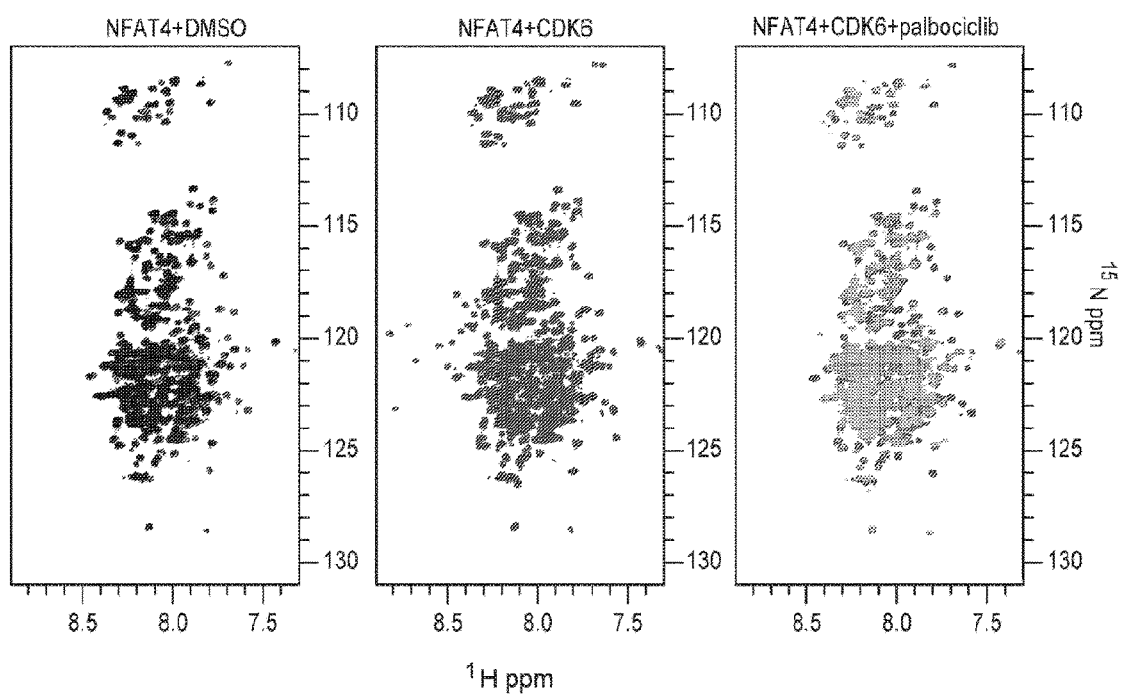
Figure 8C:
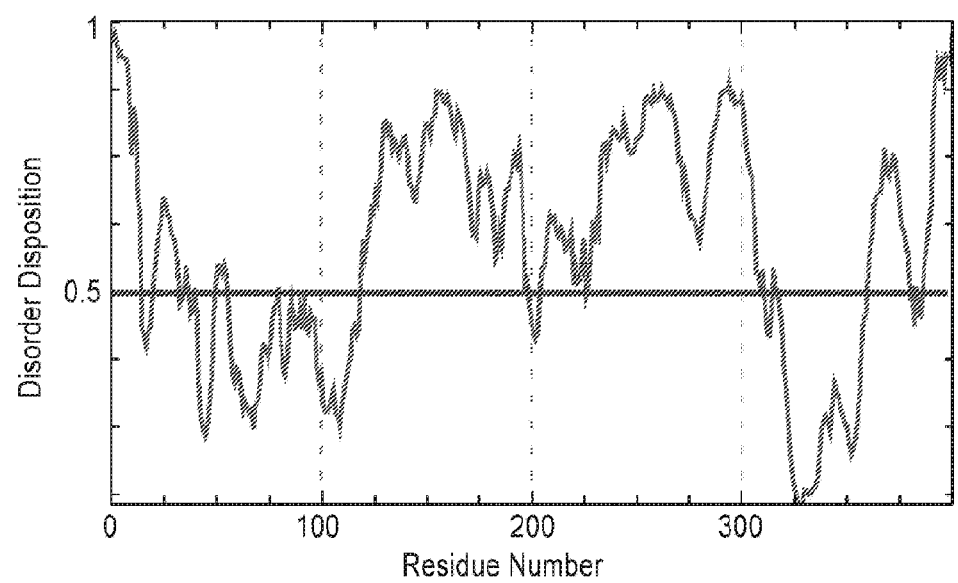

NFAT family proteins are crucial for T cell activation and transcriptional regulation of IL-2 (22). To investigate the link between CDK4/6 and NFAT in regulating IL-2 production, we measured IL-2 secretion from PD-1-overexpressing Jurkat cells stimulated in the presence of palbociclib and cyclosporine A (CsA), a calcineurin inhibitor that prevents activation of the NFAT pathway (FIG. 2A). Addition of CsA ablated production of IL-2, even in the presence of palbociclib, suggesting that CDK4/6 inhibitors increase IL-2 secretion through heightened NFAT signaling and not via an alternative pathway. Interestingly, a recent biochemical screen suggested that NFAT4 (NFATc3) is a substrate of CDK4/6 (31). To assess phosphorylation of NFAT4 by CDK4/6, we performed 2D $^{15}$N heteronuclear single quantum correlation (2DHSQC) experiments to analyze changes in chemical shifts of the regulatory domain of NFAT4 after incubation with either recombinant CDK4/Cyclin D1 or CDK6/Cyclin D3. The $^{15}$N HSQC spectrum of NFATc3 (1-400) has narrow dispersion (~1 ppm) in the $^1$H dimension centered on the random coil chemical shift of 8.0 ppm, consistent with an unstructured protein (FIG. 8A). The few resonances around the $^1$H frequency of 7.5 ppm indicate that a minor part of this protein harbors structured elements, which is in accordance with the disorder prediction from primary sequence information (FIG. 8C). When NFAT4 was incubated with CDK6, we observed the appearance of resonances corresponding to phospho-serine residues, upfield of 8.5 ppm in the 1H dimension and a number of distinct chemical shift perturbations for the residues neighboring the phosphorylation sites (FIG. 8A) (32,33). However, this did not occur when NFAT4 was incubated with CDK4 (FIG. 8A), consistent with our previous knockdown data (FIG. 1D, 1E), although we observed some non-specific peak broadening due to the presence of glycerol in the enzyme mixture. Importantly, CDK6-induced phosphorylation of NFAT4 was inhibited when the kinase was pre-incubated with palbociclib (FIG. 8B), where we observed neither phospho-serine resonances nor distinct chemical shift perturbations associated with phosphorylation. Although we observed the broadening of a few resonances after the addition of palbociclib, we confirmed that this was a non-specific effect due to the addition of DMSO (FIG. 8B).

Figure 2B:
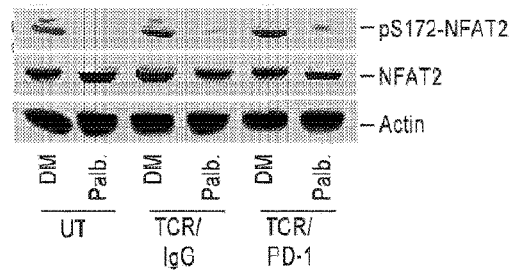

As our NMR results indicated that CDK6 is an upstream NFAT kinase, we hypothesized that CDK4/6i would result in decreased phospho-NFAT, which could lead to increased nuclear translocation and enhanced NFAT transcriptional activity (22, 26). As we were unable to assign the residues of NFAT4 that were phosphorylated by CDK6, we instead examined levels of phospho-Ser172-NFAT2, a site reported to regulate the nuclear localization of NFAT2 (34). Although we do not have evidence that CDK4/6 directly phosphorylates NFAT2, we found that treatment of PD-1-Jurkat cells with palbociclib reduced levels of phospho Ser172 NFAT2 (FIG. 2B), suggesting that multiple members of the NFAT family may be regulated by CDK4/6.

Figure 2C:
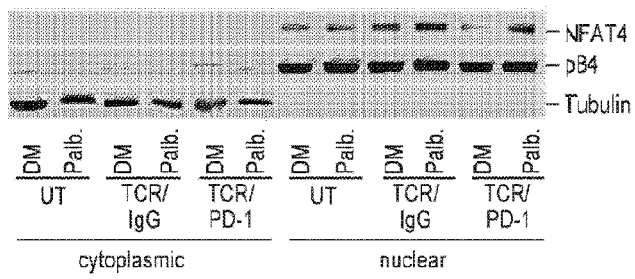
Figure 2D:
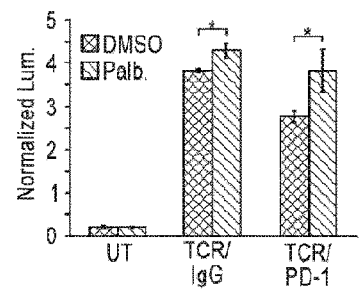
Figure 2E:
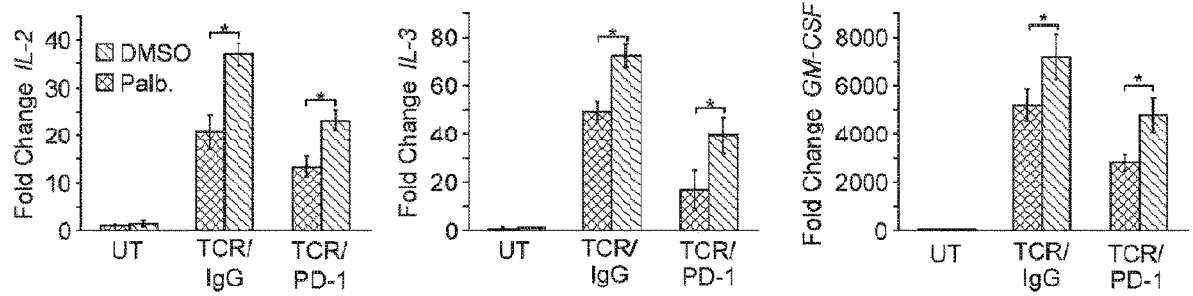

As phosphorylation of the regulatory domains of NFATs is a key regulator of their nuclear localization, we isolated nuclear and cytoplasmic fractions from unstimulated or stimulated PD-1-Jurkat cells treated with palbociclib or vehicle control, and found that CDK4/6 inhibition increased nuclear levels of NFAT4 (FIG. 2C). Consistent with increased levels of NFATs in the nucleus, we also found that exposure to palbociclib increased NFAT transcriptional activity (FIG. 2D) and mRNA expression of IL2, IL3, and GM-CSF (FIG. 2E), three previously reported NFAT targets (35). Taken together, these results reveal a novel role for CDK6 as an upstream regulator of NFAT activity, and demonstrate that pharmacological CDK4/6 inhibition can enhance T cell activation in vitro.

CDK4/6 Inhibition Enhances T Cell Infiltration into Lung Tumors

Figure 3A:
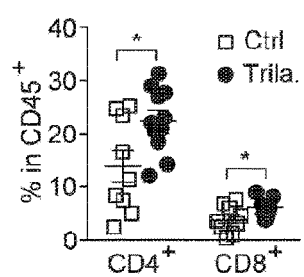
FIG. 3. Analysis of immune infiltrates of lung tumor after CDK4/6 inhibition. Genetically engineered mouse model (GEMM) harboring the $Kras^{LSL-G12D}Trp53^{fl/fl}$ mutation was induced by Ad-CRE recombinase for lung tumors. After verification of tumor formation by MRI scan, mice were then treated with either trilaciclib (trila) or palbociclib (palb) every day for 7 days, after which lung tissues were collected for FACS analysis. Results shown are pooled from three independent experiments. Lung infiltrating T cells percentage among total CD45+ leukocytes (A) or absolute cell number (B) after treatment with trilaciclib (n=8) or palbociclib (ctrl, n=4, Palb., n=5). (*p<0.05, ***p<0.001). C. BrdU incorporation by T cells shows proliferation affected by CDK4/6 inhibitors trilaciclib or palbociclib. Mice without (naïve, upper panel) or with (TMB, lower panel) $Kras^{LSL-G12D}Trp53^{fl/fl}$(KP) allograft tumor were treated with trilaciclib or palbociclib, followed by systemic BrdU injection (I.P.). BrdU incorporation within different T cell subpopulations Treg (CD4+Foxp3+) and Tconv (CD4+Foxp3−) was determined by flow cytometry (n=6) (*p<0.05, **p<0.01). D. Expression levels of PD-1 and CTLA-4 in CD4+ or CD8+ T cells infiltrated at tumor site after treatment (ctrl, n=4, Palb., n=5) (*p<0.05). E. Changes in levels of CD11b+ and CD11c+ myeloid subpopulations after trilaciclib (n=8) or palbociclib (ctrl, n=4, Palb. n=5) treatment (*p<0.05, **p<0.01).

To determine the impact of CDK4/6 inhibition on tumor infiltrating immune cells in vivo, we treated Kras$^{LSL-}$$_{G12D}$Trp53$^{fl/fl}$ (KP) mice, representing an immunocompetent genetically engineered mouse model (GEMM) of human non-small cell lung cancer (NSCLC) (36), with either palbociclib or trilaciclib. Both agents increased infiltration of CD4$^+$ T cells and CD8$^+$ cells, to a lesser degree, into lung tumors among total lung infiltrating leukocytes (TILs) (FIG. 3A). This increase of CD4+ cells was confirmed in two additional GEMMs, including the KrasLSL-G12D (K) and the Kras$^{LSL-G12D}$Lkb1$^{fl/fl}$ (KL) model[18], in which CDK4/6i also increased infiltration of TILs into lung tumors (FIG. 9A).

Figure 3B:
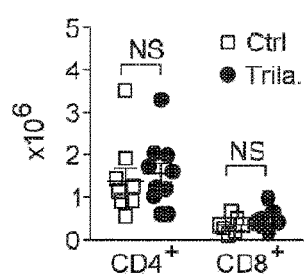
Figure 3C:
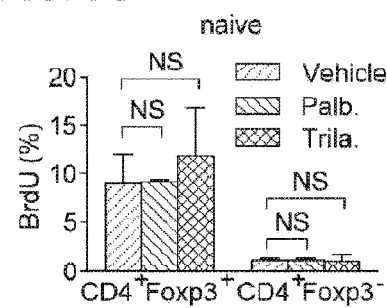
Figure 3C:
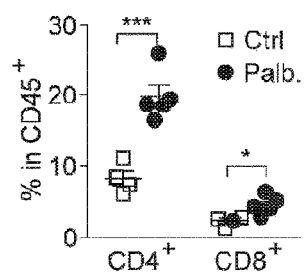
Figure 3C:
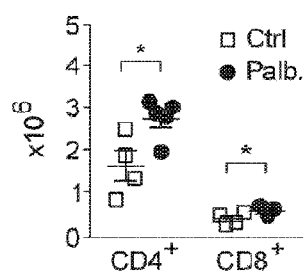
Figure 3C:
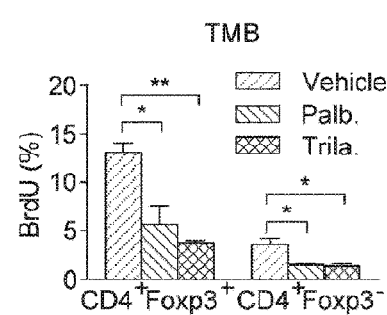
Figure 9D:
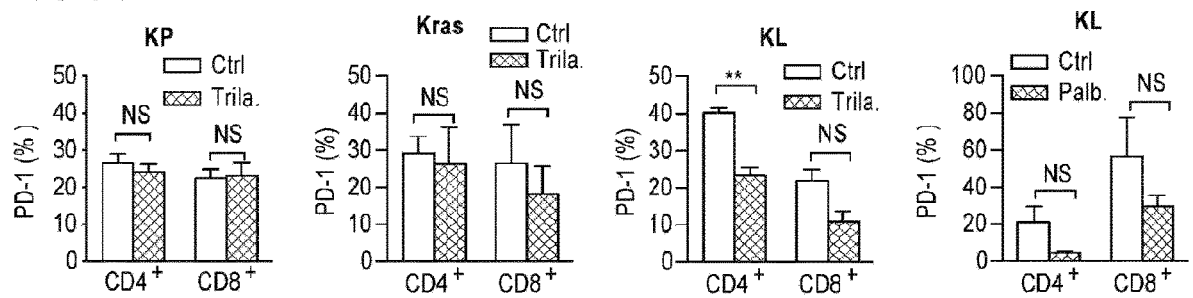
FIG. 9. Analysis of lung tumor immune infiltrates after CDK4/6 inhibition from $Kras^{G12D}$ (Kras), $Kras^{G12D}$Lkb1 (KL) or $Kras^{G12D}$Trp53$^{fl/fl}$ (KP) mice. Genetically engineered mouse models (GEMMs) harboring Kras, KP or KL mutations were induced to form tumors by Ad-CRE recombinase administration, as verified by MRI scan. Then the mice were treated with either palbociclib or trilaciclib (100 mg/kg, PO) every day for 7 days. A. Percentage of lung-infiltrating T cells within CD45+ total leukocytes after treatment. Left panel, Kras mice treated with trilaciclib. Middle panel, KL mice treated with trilaciclib. Right panel, KL mice treated with palbociclib. (n=3) B. Percentages of Tregs within CD4+ T cells after trilaciclib or palbociclib treatment. (n=3) C. Changes of Treg percentage within CD4+ TILs from KP GEMM mice after palbociclib (upper panel) or trilaciclib (lower panel) treatment. (n=5) D. Expression of PD-1 on CD4+ or CD8+ TILs within tumors after trilaciclib or palbociclib treatment. (n=3) E. Expression of CTLA-4 on CD4+ or CD8+ TILs after trilaciclib or palbociclib treatment. (n=3) F. representative flow panels showing PD-1 (left panels) and Ctla-4 (right panels) expression levels from CD4+ T cells after palbociclib treatment.
Figure 10A:
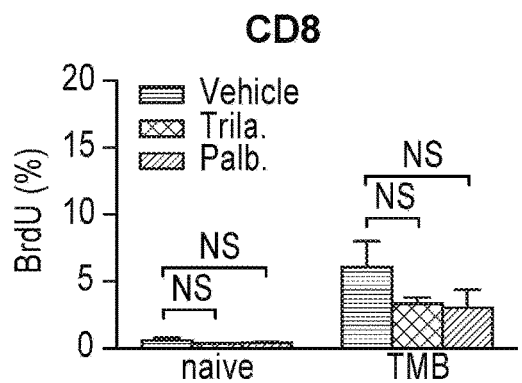
FIG. 10. T cell proliferation and cytokine/chemokine profiling of $Kras^{G12D}$Trp53$^{fl/fl}$ GEMM mice. A. BrdU incorporation by CD8+ T cells shows proliferation affected by CDK4/6 inhibitors trilaciclib or palbociclib. Mice without (naive) or with (TMB) $Kras^{LSL-G12D}$Trp53$^{fl/fl}$ (KP) allograft tumor were treated with trilaciclib or palbociclib, followed by BrdU injection systemically (I.P.). BrdU incorporation was determined by flow cytometry. (n=6) B. Splenocytes from mice with (TMB) or without (naive) $Kras^{G12D}$Trp53$^{fl/fl}$ tumor were dissociated and labeled with CFSE. Cells were cultured and treated with trilaciclib at the indicated concentrations in the presence of α-CD3/CD28 antibody stimulation. After 2 days of stimulation, proliferating cells were quantified as CFSE low cells compared to unstimulated controls for CD4+ (upper panel) and CD8+ (lower panel) T cells. C. BAL fluid was collected 7 days after the treatment of trilaciclib and analyzed for cytokine profiling using Luminex. Expression levels of the analyzed cytokines were expressed as log-2 fold change (L2FC) relative to vehicle control group and shown as a heat map. Each column represents one mouse. D. Absolute expression levels of IL-6, IL-10, IL-23 and Cxcl9 from control or trilaciclib-treated mice as shown in panel (C).

Although CDK6 plays a critical role in T cell proliferation (26,37), transient inhibition of CDK4/6 did not decrease total number of TILs in these lung tumors, while absolute numbers of CD4+ and CD8+ cells only mildly changed (FIG. 3B). This finding suggests that CDK4/6 inhibition can either induce intratumoral T cell expansion, which is unlikely given the requirement for CDK4/6 for cell proliferation (19), or can lead to increased homing of effector T cells to the tumor. To explore the impact of CDK4/6i on TIL proliferation, we evaluated BrdU incorporation in vivo. CDK4/6i did not alter BrdU incorporation in CD4$^+$ or CD8$^+$ cells from naive mice without tumors (FIG. 3C, upper panel, FIG. 10A), but did diminish BrdU incorporation in both CD4$^+$Foxp3$^-$ conventional T cells (Tconv) and CD4+ Foxp3+ regulatory T cells (Treg), but not CD8+ cells, isolated from mice bearing Kras$^{LSLG12D}$Trp53$^{fl/fl}$ allografts (FIG. 3C, lower panel, FIG. 10A). Similarly, CDK4/6i more potently reduced proliferation of T cells from tumor-bearing mice than naïve mice after stimulation ex vivo (FIG. 10A, 10B), possibly because proliferation of naïve T cells relies on CDK1 and other transcriptional factors such as T-bet (19,38), while tumor infiltrating CD4$^+$ lymphocytes are more susceptible to CDK4/6i. However, the percentage of Tregs did not show significant changes among CD4$^+$ TILs after CDK4/6i treatment (FIG. 9B, 9C).

Figure 9E:
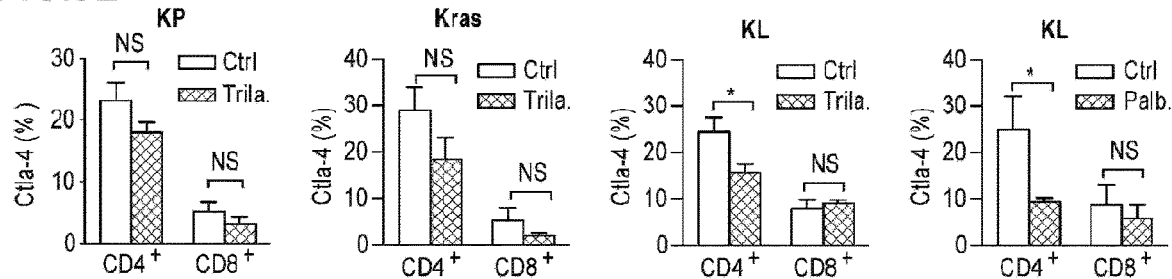
Figure 9F:
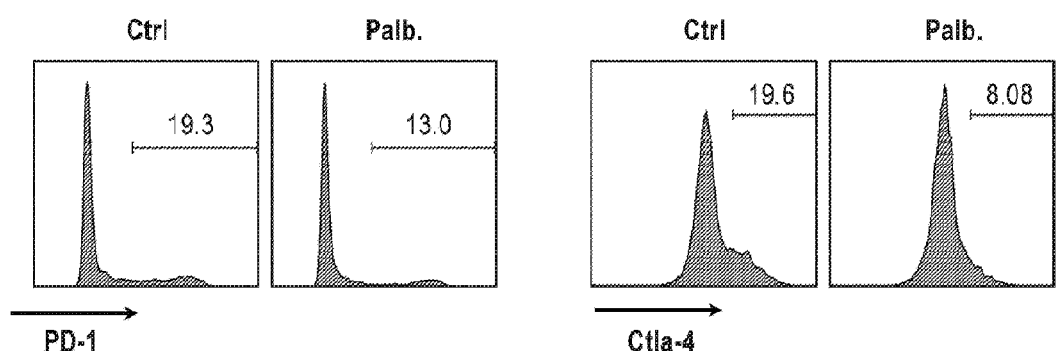
Figure 10C:
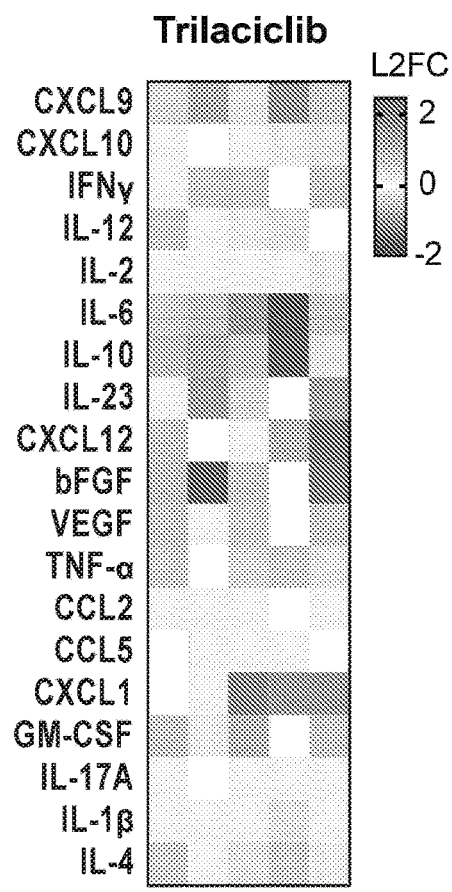
Figure 10B:
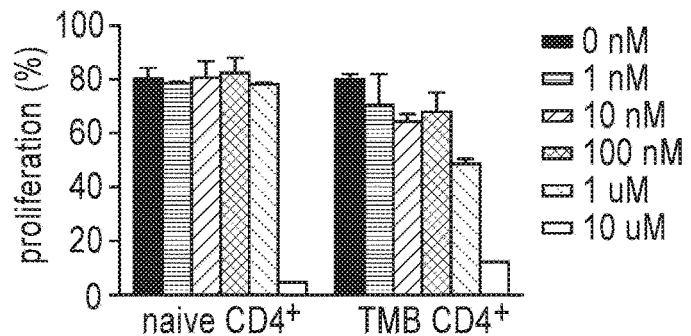
Figure 10B:
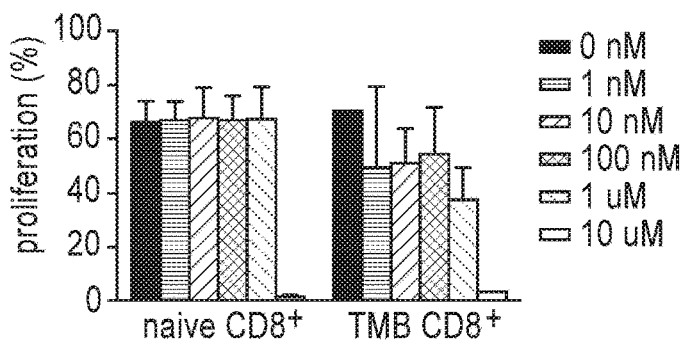
Figure 10D:
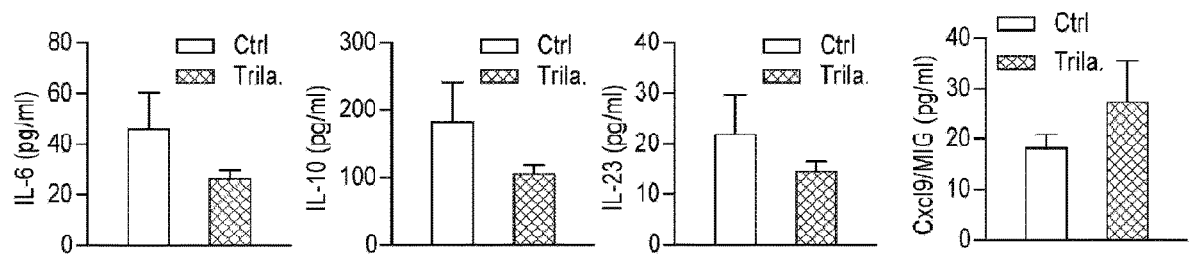

We next evaluated the impact of CDK4/6i on the immune microenvironment beyond T cell proliferation and IL-2 secretion by investigating chemokines, expression of exhaustion markers, and the proliferation of other stromal cells. Levels of the Th1 chemokines CXCL9 and CXCL10, which govern the trafficking of effector T cells to tumor sites (30,39), were increased in the lung after CDK4/6 inhibition (FIG. 10C, 10D). Levels of coinhibitory molecules, including PD-1 and CTLA-4, were reduced in both CD4$^+$ and CD8$^+$ T cells after palbociclib or trilaciclib treatment, albeit to different extents (FIG. 3D, FIG. 9D-E). CDK4/6i also reduced the abundance of CD11c$^+$ myeloid cells (FIG. 3E), which may be due to decreased proliferation of bone marrow hematopoietic progenitors (26). We also observed reduced levels of IL-6, IL-10, and IL-23 after CDK4/6i (FIG. 10D), three cytokines produced by myeloid cells that suppress the Th1 response in cancer (40, 41). Taken together, these data indicate that despite effects on T cell PROLIFERATION, CDK4/6 inhibition results in an increased percentage of effector cells within the tumor microenvironment, correlated to chemokine secretion, with apparent downregulation of coinhibitory molecules in some of the models tested. Moreover, the anti-proliferative effect of CDK4/6i does not result in an increase of Tregs among TILs, but does result in a reduced number of the myeloid subpopulation.

Figure 4A:
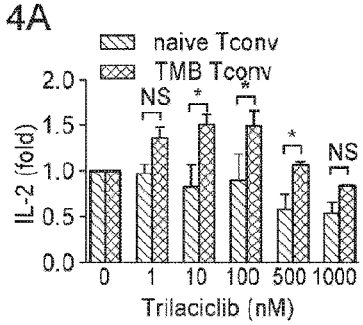
FIG. 4. Tumor antigen-experienced T cells exhibit greater sensitivity to CDK4/6 inhibition. A. IL-2 production from Tconv cells after trilaciclib treatment. CD4+CD25− Tconv cells were isolated from either naïve or tumor bearing (TMB) mice and treated with trilaciclib at indicated concentrations, in the presence of CD3 and CD28 stimulation. IL-2 production was determined 3 days after the treatment and normalized with untreated control. (n=3) (*p<0.05) B. Increased IFNγ production in CD8+ T cells by trilaciclib treatment, in the presence of Treg. CD8+ T cells from naïve or TMB mice were isolated and co-cultured with CD4+CD25+ Treg cells (5:1 ratio), in the presence of different concentrations of trilaciclib as indicated. IFNγ production was determined 3 days after the treatment and normalized with untreated control. (n=3) (*p<0.05, **p<0.01) C. Violin plot of expression levels of NFAT regulated genes determined by single-cell RNA-seq of tumor-infiltrating CD3+ T cells from KP GEMM mice 7 days after trilaciclib treatment. D. t-Distributed Stochastic Neighbor Embedding (t-SNE) plot showing distinct homogenous groups of T cells identified with density based clustering (dbscan). E. Heat map showing transcriptional levels of genes from each cell that are important for T cell activation and suppression, and IL-2 and TCR signaling. The status of each cell including treatment status and group identification is shown below the heat map as bar graphs. Each column represents one cell.
Figure 4B:
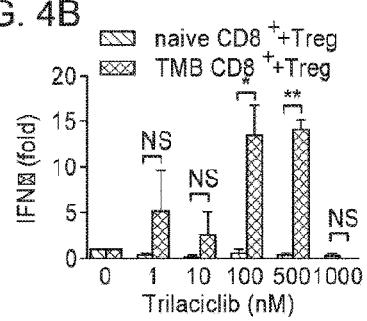
Figure 11A:
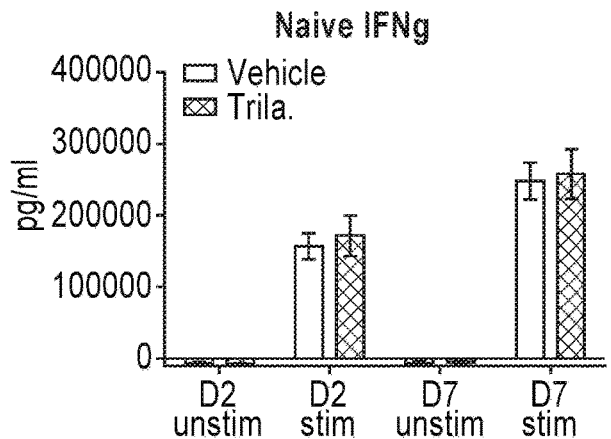
FIG. 11. Tumor antigen experienced T cells are more sensitive to CDK4/6 inhibition. A. Naive C57BL/6 mice were treated with trilaciclib (100 mg/kg, IP) or vehicle for three days. Two and seven days after the final treatment, splenocytes were isolated and stimulated with α-CD3/CD28 antibodies for 72 hours to measure IFNγ production by ELISA. B. C57BL/6 mice were implanted with B16F10 tumor cells. Seven days post implantation mice were treated with trilaciclib (100 mg/kg, IP) or vehicle for 5 days. Five days post final treatment splenocytes were isolated and stimulated with α-CD3/CD28 antibodies for IFNγ production by ELISA. C. IL-2 production from Tconv (CD4+ CD25−) cells after trilaciclib treatment. Tconv cells were isolated from either naive or tumor bearing (TMB) mice and treated with trilaciclib at indicated concentrations, in the presence of CD3 and CD28 antibodies. IL-2 production was determined 3 days after the treatment as percentage. (n=3) IFNγ production in CD8+ T cells alone from naive or TMB mice after treatment with trilaciclib, as shown by percentage (D) or fold change (E). (n=3) F. Increased IFNγ production in CD8+ T cells by trilaciclib in the presence of Tregs. CD8+ T cells from naive or TMB mice were isolated and co-cultured with CD4+CD25+ regulatory T cells (5:1 ratio), in the presence of different concentrations of trilaciclib as indicated. IFNγ production was determined 3 days after the treatment as shown as percentage. (n=3).
Figure 11B:
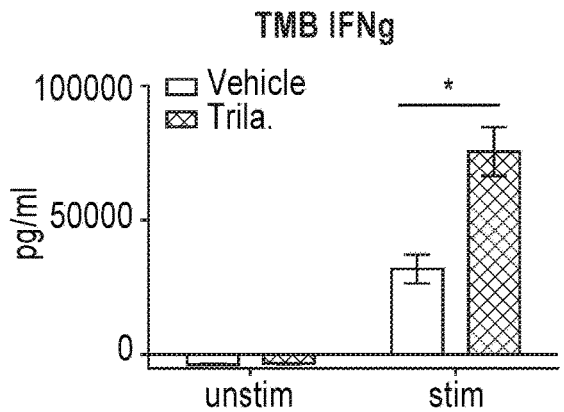
Figure 11C:
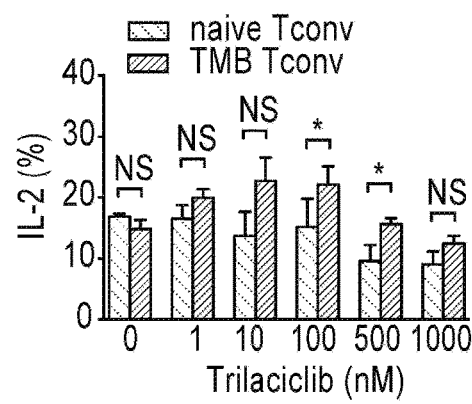
Figure 11D:
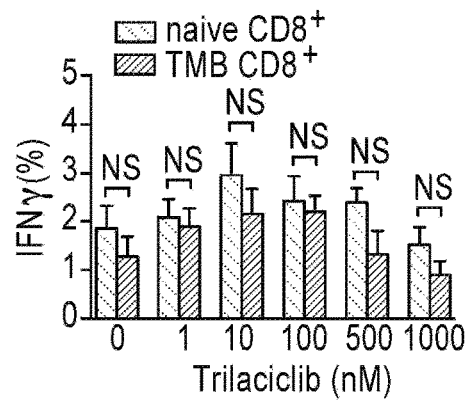
Figure 11E:
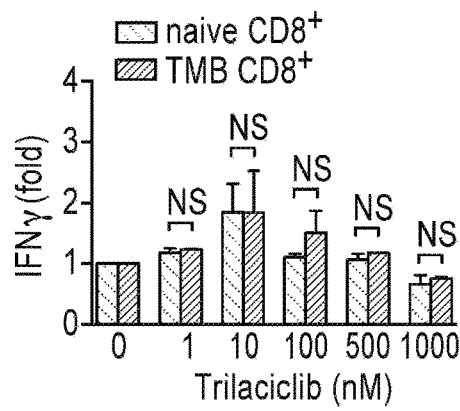
Figure 11F:
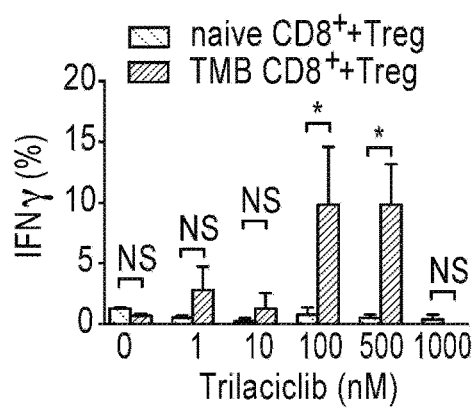
Figure 12A:
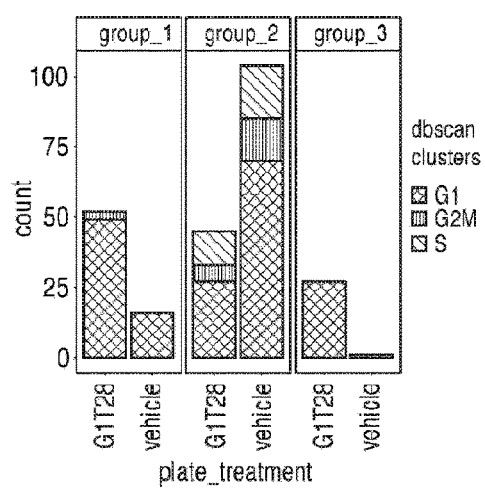
FIG. 12. Short-term CDK4/6 inhibition alters the cell cycle status of tumor infiltrating T cells. A. Bar graph of cell cycle status of T cells, as analyzed by single-cell RNA-seq, from each group of cells with or without trilaciclib treatment, determined by cyclone classification tool. B. 2D t-SNE plot with cell cycle stage overlaid to depict the status of each cell. C. The human KRAS-TP53 mutant NSCLC cell line H358 was treated with CDK4/6 inhibitors (100 nM) for 24 hrs. Cell lysate were collected for Western blot showing changes in the levels of phospho-Rb, p-AKT and p-ERK. D. Changes in cell cycle status of H358 after treatment by CDK4/6 inhibitors in panel (C). E. Tumor-infiltrating CD3+ T cells were isolated from lung tumors from KP GEMM mice after 7 days of treatment with trilaciclib and analyzed by single-cell RNA-seq. Tumor infiltrating T cells were sorted for single-cell RNA-seq analysis. These cells from either trilaciclib treated or control group were identified as three homogeneous groups based on dimension reduction with t-SNE combined with density based clustering (db-scan). Violin plot showing NFAT regulated genes expression among all three groups.
Figure 12B:
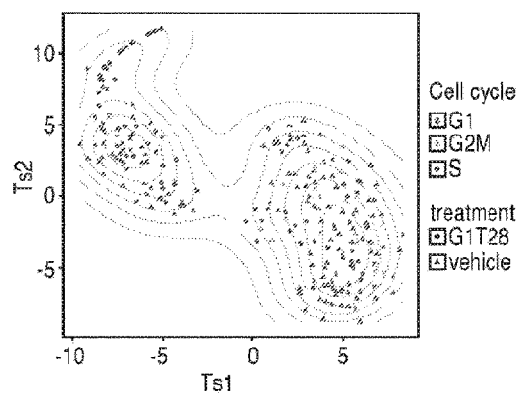
Figure 12C:
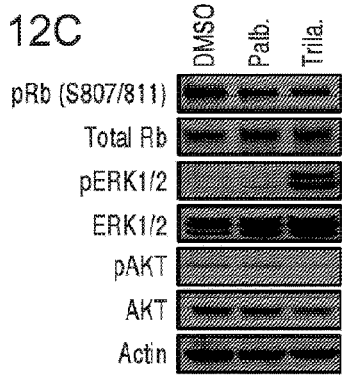
Figure 12D:
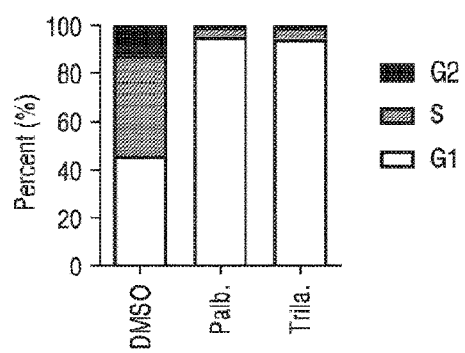
Figure 12E:
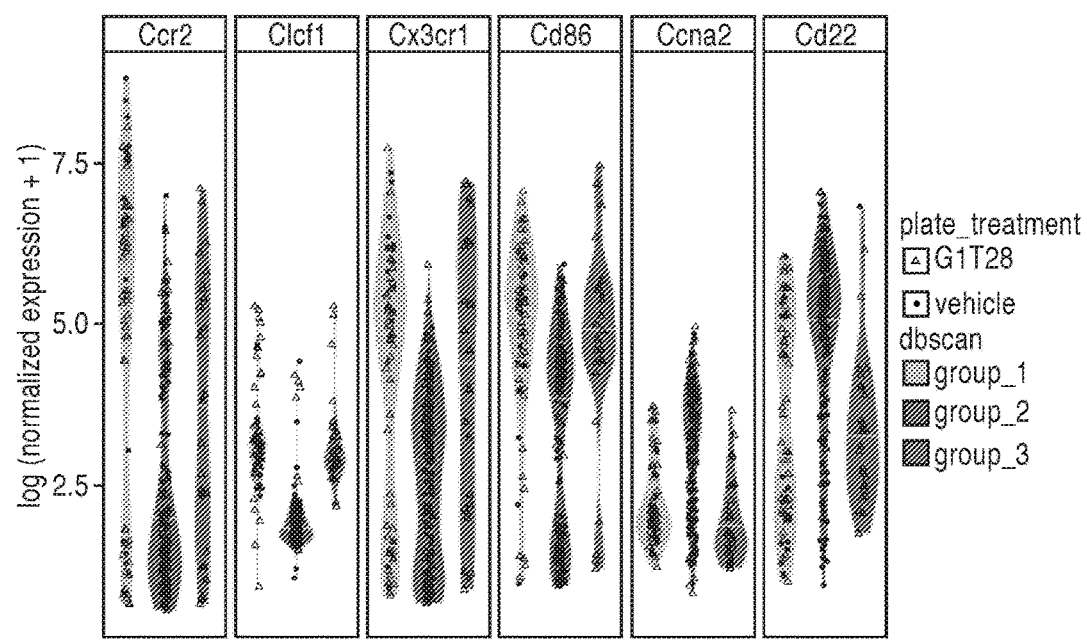

Example 4: Tumor Antigen-Experienced T Cells More Sensitive to CDK4/6 Inhibition than Naïve T Cells As a recent report demonstrated that lymphocyte proliferation inhibition by CDK4/6i is transient and reversible (27), it is possible that properly timed and sequenced doses of CDK4/6i can activate effector T cells without adversely suppressing their proliferation. To evaluate the impact of CDK4/6i on T cell activation, IFNγ secretion was evaluated. Total splenocytes isolated from tumor-bearing mice, but not naïve mice, treated with trilaciclib in vivo demonstrated increased IFNγ secretion (FIG. 11A, 11B). This finding was further confirmed by treatment with trilaciclib ex vivo, which increased IL-2 production only in cells from tumor-bearing mice (FIG. 4A, FIG. 11C). Moreover, although CDK4/6i did not significantly alter IFNγ secretion by $CD8^+$ cytotoxic T cells alone (FIG. 11D, 11E), co-culture of splenic $CD8^+$ T cells from tumor-bearing mice with Tregs in the presence of trilaciclib relieved Treg-mediated suppression, as IFNγ production increased by ~10 fold. In contrast, the effect of CDK4/6i on IFNγ production from naïve $CD8^+$ T cells co-cultured with Tregs was minimal (FIG. 4B, FIG. 11F). These data suggest that CDK4/6i can augment effector T cell function even in the presence of Tregs.

To further investigate the effects of CDK4/6 inhibition on tumor-infiltrating T cells in vivo, we performed single-cell RNA sequencing (RNA-seq) on $CD3^+$ T cells isolated from KP GEMM lung tumors. Gene Ontology (GO) analysis revealed enrichment for processes related to lymphocyte activation and proliferation (Table 2).

TABLE 2

GO Ontology analysis results

| GO Term | Description | P-value | FDR q-value | Enrichment | N | B | n | b |
| --- | --- | --- | --- | --- | --- | --- | --- | --- |
| 1. GO:0002376 | immune system process | 1.36E−17 | 1.70E−13 | 5.2 | 10930 | 822 | 92 | 36 |
| 2 GO:0050778 | positive regulation of immune response | 2.47E−10 | 1.54E−06 | 7.57 | 10930 | 251 | 92 | 16 |
| 3 GO:0048584 | positive regulation of response to stimulus | 2.49E−09 | 1.04E−05 | 3.35 | 10930 | 1029 | 92 | 29 |
| 4 GO:0002696 | positive regulation of leukocyte activation | 3.49E−09 | 1.09E−05 | 8.49 | 10930 | 182 | 92 | 13 |
| 5 GO:0050776 | regulation of immune response | 3.79E−09 | 9.48E−06 | 5.41 | 10930 | 395 | 92 | 18 |
| 6 GO:0050867 | positive regulation of cell activation | 5.53E−09 | 1.15E−05 | 8.17 | 10930 | 189 | 92 | 13 |
| 7 GO:0002684 | positive regulation of immune system process | 9.08E−09 | 1.62E−05 | 4.81 | 10930 | 469 | 92 | 19 |
| 8 GO:0051251 | positive regulation of lymphocyte activation | 1.04E−08 | 1.63E−05 | 8.75 | 10930 | 163 | 92 | 12 |
| 9 GO:0042127 | regulation of cell proliferation | 1.97E−08 | 2.74E−05 | 3.49 | 10930 | 852 | 92 | 25 |
| 10 GO:0006955 | immune response | 3.30E−08 | 4.12E−05 | 5.02 | 10930 | 402 | 92 | 17 |
| 17 GO:0002429 | immune response-activating cell surface receptor signaling pathway | 1.28E−07 | 9.38E−05 | 13.39 | 10930 | 71 | 92 | 8 |
| 21 GO:0050670 | regulation of lymphocyte proliferation | 1.80E−07 | 1.07E−04 | 8.8 | 10930 | 135 | 92 | 10 |
| 28 GO:0050671 | positive regulation of lymphocyte proliferation | 5.24E−07 | 2.34E−04 | 11.18 | 10930 | 85 | 92 | 8 |
| 30 GO:0001819 | positive regulation of cytokine production | 6.12E−07 | 2.55E−04 | 6.04 | 10930 | 236 | 92 | 12 |
| 39 GO:0060326 | cell chemotaxis | 1.24E−06 | 3.96E−04 | 10 | 10930 | 95 | 92 | 8 |
| 40 GO:0016477 | cell migration | 1.42E−06 | 4.45E−04 | 4.69 | 10930 | 355 | 92 | 14 |
| 43 GO:0001817 | regulation of cytokine production | 2.25E−06 | 6.54E−04 | 4.51 | 10930 | 369 | 92 | 14 |
| 44 GO:0006935 | chemotaxis | 2.38E−06 | 6.77E−04 | 7.69 | 10930 | 139 | 92 | 9 |
| 74 GO:0051480 | regulation of cytosolic calcium ion concentration | 1.08E−05 | 1.83E−03 | 9.14 | 10930 | 91 | 92 | 7 |
| 92 GO:0006874 | cellular calcium ion homeostasis | 4.64E−05 | 6.30E−03 | 6.13 | 10930 | 155 | 92 | 8 |
| 95 GO:0007204 | positive regulation of cytosolic calcium ion concentration | 5.12E−05 | 6.74E−03 | 9.02 | 10930 | 79 | 92 | 6 |
| 97 GO:0055074 | calcium ion homeostasis | 5.81E−05 | 7.49E−03 | 5.94 | 10930 | 160 | 92 | 8 |
| 109 GO:0051482 | positive regulation of cytosolic calcium ion concentration involved in phospholipase | 9.07E−05 | 1.04E−02 | 32.4 | 10930 | 11 | 92 | 3 |

Enrichment (N, B, n, b) is defined as follows:
N = total number of genes
B = total number of genes associated with a specific GO term
n = number of genes in the top of the user's input list or in the target set when appropriate
b = number of genes in the intersection
Enrichment = (b/n)/(B/N)

Figure 4C:
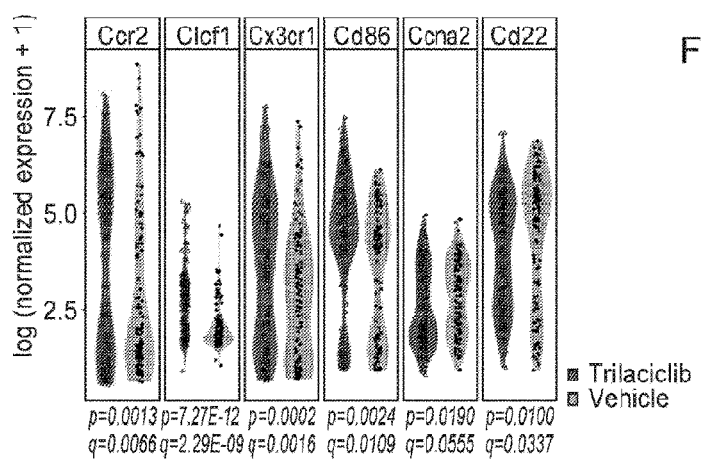

Several reported NFAT targets were upregulated by trilaciclib, including Ccr2, Clcf1, Cx3cr1 and CD86 (FIG. 4C, Table 3), consistent with our in vitro findings (FIG. 2). Conversely, we observed downregulation of Ccna2 and Cd22, which are negatively regulated by NFATs (FIG. 4C, Table 3). Thus, single-cell RNA-seq data was consistent with our in vitro findings indicating that inhibition of CDK4/6 de-represses NFAT activity.

TABLE 3

Selected genes reported to be regulated by NFAT

| | log2(G1T28 vs vehicle) |
|---|---|
| Ccr2[61] 3.090597614 | Ccr21 3.090597614 |
| Ece1[62] 2.973761813 | Ece12 2.973761813 |
| Clcf1[63] 1.470080066 | Clcfl3 1.470080066 |
| Il7r[64] 1.461492037 | Il7r4 1.461492037 |
| Cx3cr1[22] 1.23291456 | Cx3cr15 1.23291456 |
| Aif1[65] 1.044858682 | Aifl6 1.044858682 |
| Tnfsf8[63] 1.037029284 | Tnfsf83 1.037029284 |
| Il2ra[66] 0.941288346 | Il2ra7 0.941288346 |
| Ccnd1[67] 0.822259494 | Ccnd18 0.822259494 |
| Ccl5[63] 0.741580164 | Ccl53 0.741580164 |
| Cxcl1[68] 0.717471837 | Cxcl19 0.717471837 |
| Ccl2[63, 69] 0.628587426 | Ccl23,10 0.628587426 |
| Cd86[70] 0.620956798 | Cd8611 0.620956798 |
| Csf1[63] 0.596550748 | Csfl3 0.596550748 |
| Ccna2[71] −1.194273245 | Ccna212 −1.194273245 |
| Cd22[72] −1.231585552 | Cd2213 −1.231585552 |

Figure 4D:
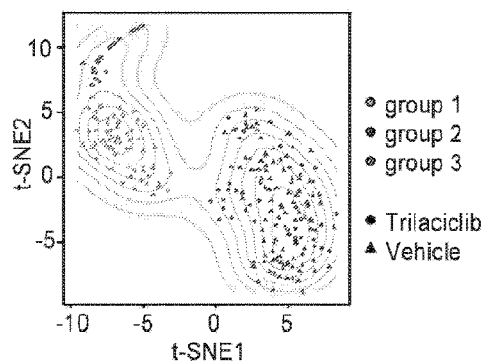
Figure 13A:
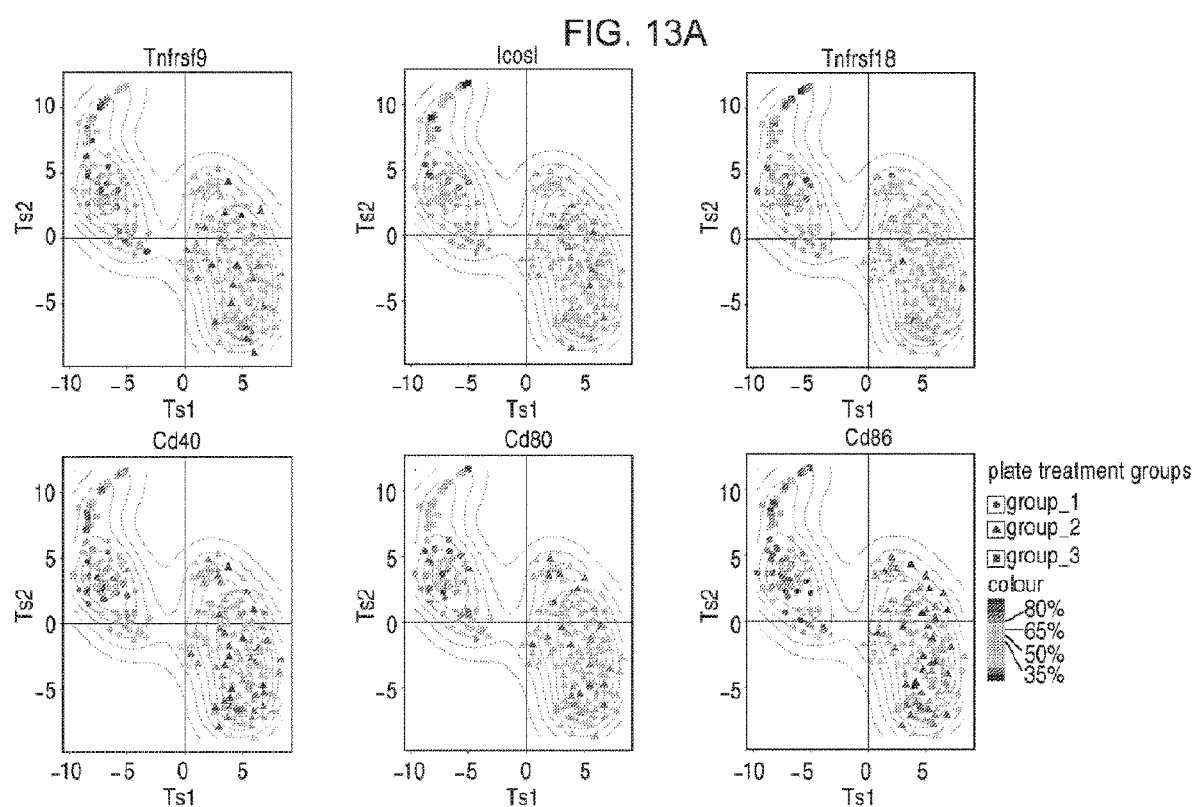
FIG. 13. CDK4/6 inhibition induces changes in the expression of activation and suppression marker genes in tumor-infiltrating T cells. A. Tumor infiltrating CD3+ T cells were isolated from $Kras^{G12D}Trp53^{fl/fl}$ GEMM mice treated with trilaciclib for 7 days and analyzed by single-cell RNA-seq. According to gene expression signatures, 2D t-Distributed Stochastic Neighbor Embedding (t-SNE) plot of RNA-seq gene signatures were overlaid with T cell activation marker genes (A) and suppression marker genes (B) for all three groups of cells from trilaciclib treated or control mice.
Figure 13B:
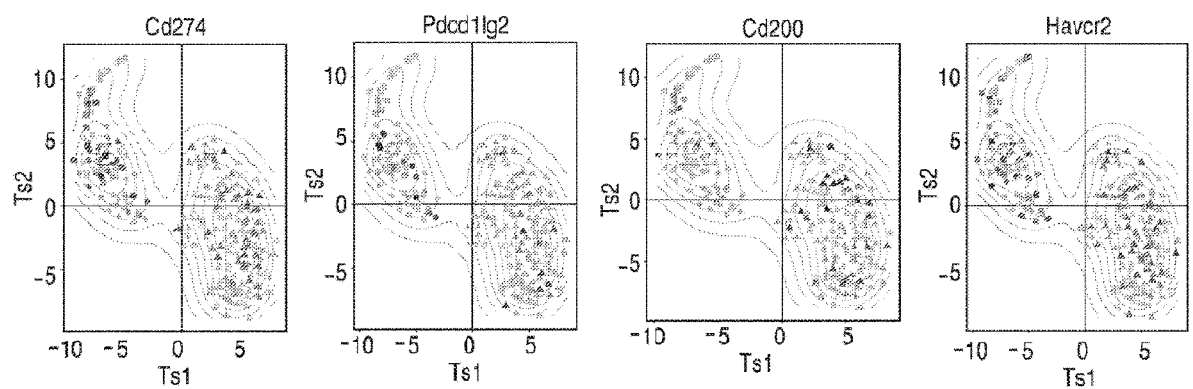

We further analyzed the T cell RNA-seq data by unsupervised density based clustering on t-Distributed Stochastic Neighbor Embedding (t-SNE) analysis to separate cells into three different groups (clusters) according to gene expression signatures (FIG. 4D). One group was comprised almost exclusively of cells from trilaciclib-treated mice (group 3). A second group contained cells predominantly from trilaciclib treated mice, but also from vehicle treated animals (group 1). The final group (group 2) represented a mixture of cells from vehicle and trilaciclib-treated mice (FIG. 4D). Trilaciclib treatment significantly increased IL-2 signaling activation in group 3, as well as in group 1, to a lesser extent. This activation includes upregulation of IL-2 receptors IL-2Rα, IL-2Rβ and IL-2Rγ (FIG. 4E). Treatment with trilaciclib increased the proportion of T cells in the G1 phase in groups 1 and 3 (FIG. 12A), confirming on-target pharmacodynamic effects in these cells. Compared to cells in group 2, cells from groups 1 and 3 showed evidence of highly activated NFAT signaling (FIG. 12E), along with heightened upregulation of activation markers, including 4-1BB (Tnfrsf9), Icosl, GITR (Tnfrsfl8), CD40 and CD86 (FIG. 4E, FIG. 13A). Compared with group 1, cells in group 3 showed greater downregulation of inhibitory markers (42), including Pd-11 (Cd274), Pd-12 (Pdcd11g2), Tim3 (Havcr2), Cd200 and its receptors (FIG. 4E, FIG. 13B). Additionally, these cells demonstrated greater TCR signaling, manifested by upregulation of Zap70, Lat, Skap1 and Cd6, which are important for continued T cell activation after TCR engagement, as well as for effector T cell function (FIG. 4E). Interestingly, these hyperactive cells were primarily in the G1 phase (FIG. 12B), consistent with the effect of CDK4/6 inhibition on traversal from G1 to S in both cancer cells and immune cells (FIG. 12). Therefore, despite inhibitory effects on cell cycle progression, short-term exposure to a CDK4/6i resulted in a gene transcription signature consistent with enhanced T cell function.

Figure 5A:
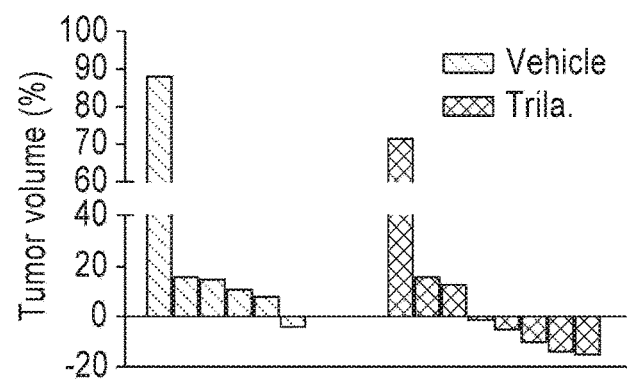
FIG. 5. CDK4/6 inhibitor elicits anti-tumor immunity and enhance cell death induced by anti-PD-1 antibody ex vivo. A. Quantification of tumor volume changes by MRI scan after treatment with trilaciclib. Left panel, waterfall plot shows tumor volume response to the treatment. Each column represents one mouse. Right panel, representative MRI scan images (one out of 24 scanned images of each mouse) show mice lung tumors before and after the treatment. Circled areas, heart. B. Live (AO=green)/Dead (PI=red) analysis of murine derived organotypic tumor spheroid (MDOTS) cultured in 3-D microfluidic culture at day 0, day 3 and day 6 following treatment of CDK4/6 inhibitors trilaciclib or palbociclib (100 nM) alone or in combination with PD-1 antibody (10 µg/ml) as indicated. Upper panel, quantification results of live/dead analysis; lower panel, representative images of deconvolution fluorescence microscopy shows live/dead cells at day 6 after indicated treatment. Statistical analysis is calculated by comparing the indicated treatment group with DMSO+IgG group at day 6. (*p<0.05, p<0.01, *p<0.001) Scale bar, 50 µm C. Cytokine secretion from MC38 MDOTS were expressed as log 2-fold change (L2FC) relative to untreated control after indicated treatment.
Figure 5A:
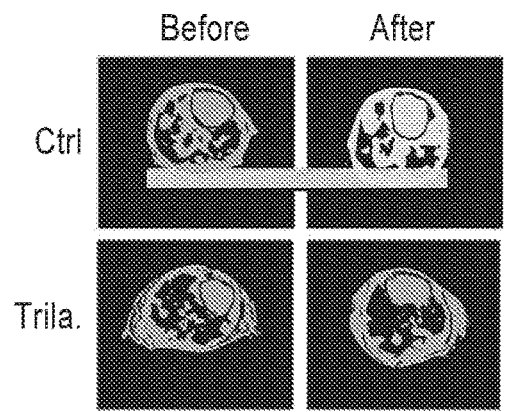
Figure 5B:
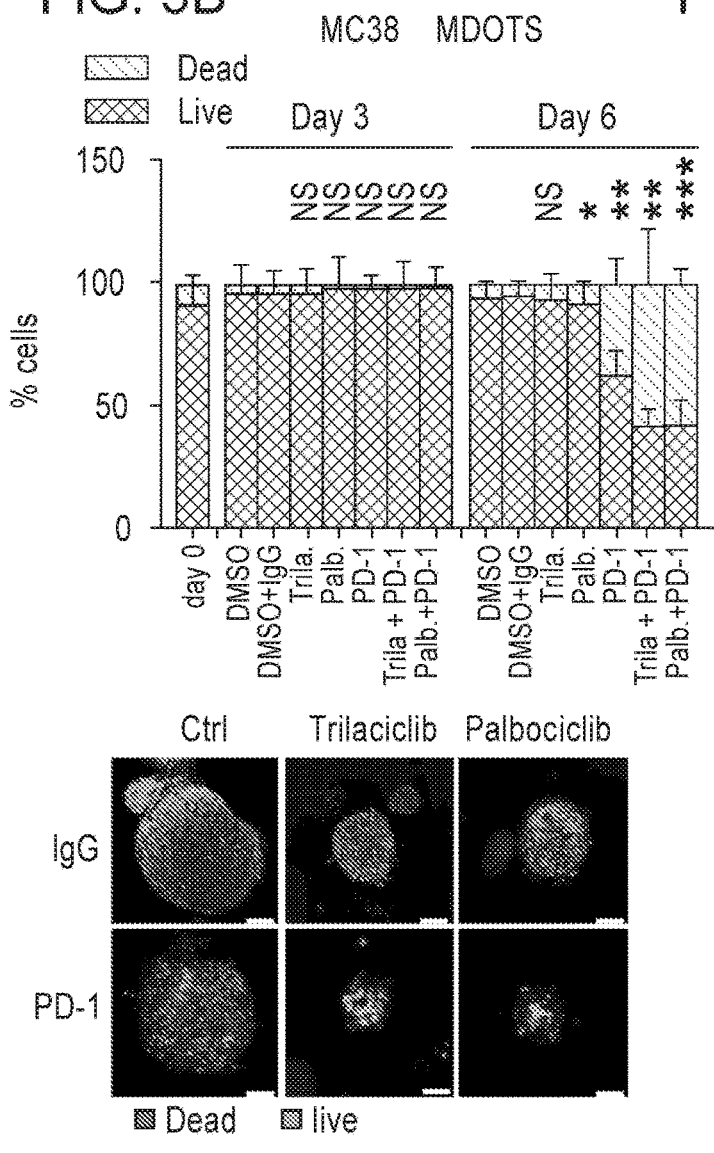
Figure 5C:
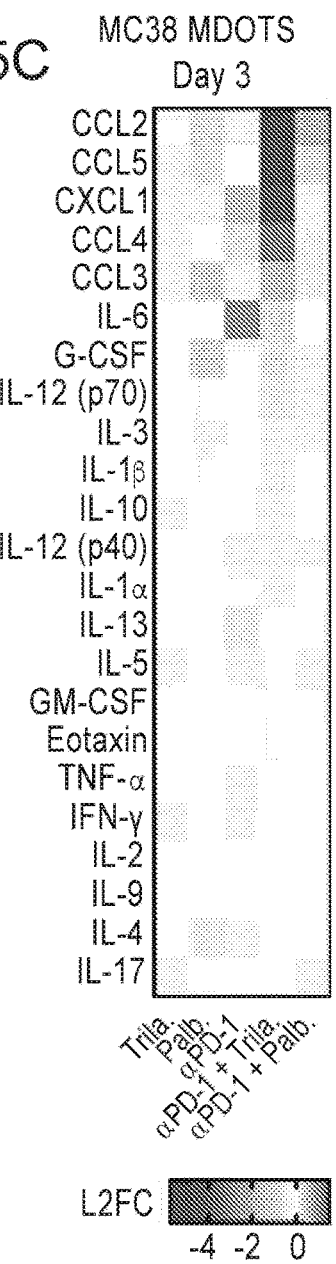
Figure 14A:
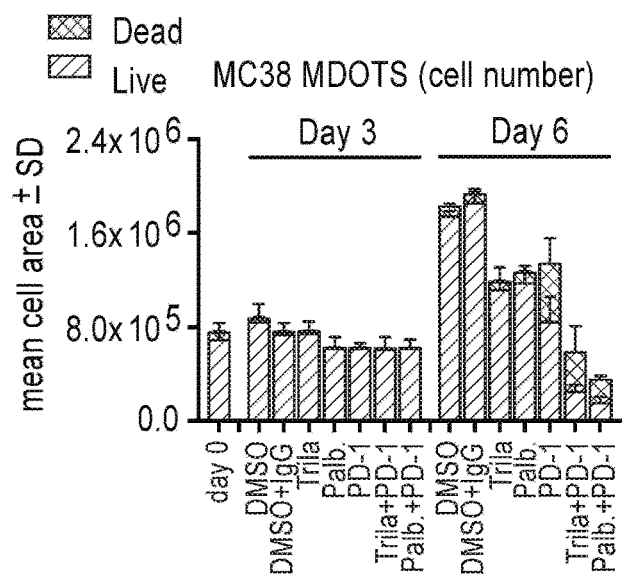
FIG. 14. Combination treatment of CDK4/6 inhibitor and anti-PD-1 antibody elicits anti-tumor immunity. A. Murine-derived organotypic tumor spheroid (MDOTS) were cultured in 3-D microfluidic system, and cell viability was quantified by staining with Live (AO=green)/Dead (PI=red) at day 0, day 3 and day 6 after treatment of CDK4/6 inhibitors (100 nM) alone or in combination with PD-1 antibody (10 μg/ml) as indicated. Data displayed as absolute cell number. B. Quantification of Live/Dead percentage of MDOTS generated from MC38 tumor implanted in $Rag1^{-/-}$ mice. The result was quantified at day 6 after indicated treatment. Statistical analysis is calculated by comparing the indicated treatment group with control group at day 6. C. Live/Dead analysis of MDOTS cultured in 3-D microfluidic culture and treated with CDK4/6 inhibitors trilaciclib or palbociclib (100 nM) with PD-1 antibody (10 μg/ml) without or with neutralization antibodies anti-IFN-γ (10 μg/ml) or anti-CCL5 (10 μg/ml) as indicated 6 days after the treatment. The result is displayed as percentage. Statistical analysis is calculated by comparing the indicated treatment group with control group at day 6 (*p<0.05,**p<0.01).
Figure 14B:
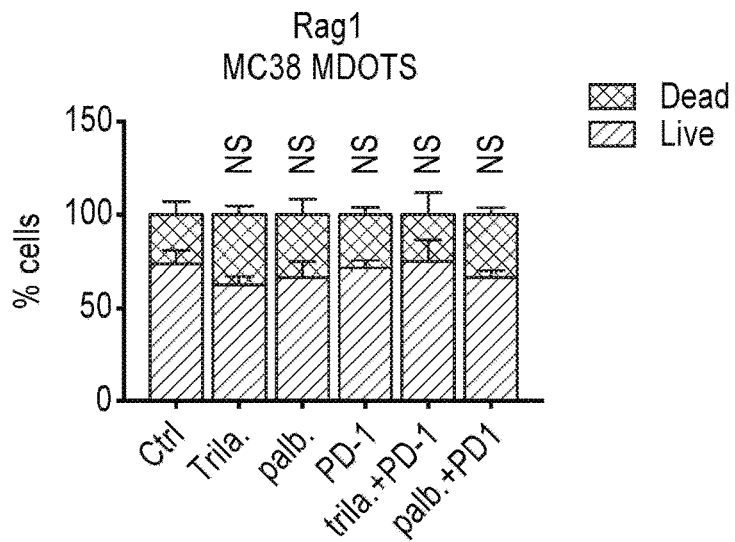
Figure 14C:
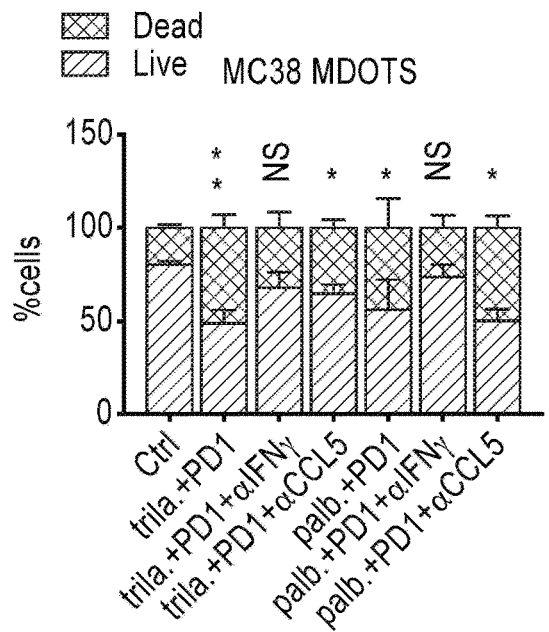

Example 5: CDK4/6 Inhibition Augments Anti-PD-1 Antibody Induced Anti-Tumor Immunity We next examined effects of CDK4/6i on tumor burden. CDK4/6i alone was not sufficient to eradicate tumors despite reduced tumor proliferation and increased T cell activation and infiltration in the KP GEMM model (FIG. 5A) consistent with a previous report that palbociclib reduces the growth of Kras-driven murine lung tumors (43). We therefore evaluated the ability of CDK4/6i to complement PD-1 blockade. As Kras mutant GEMMs are not responsive to checkpoint blockade (3, 44), in part due to a low levels of somatic mutations (45), we utilized the murine syngeneic colon adenocarcinoma model MC38. We first demonstrated that anti-PD-1 combined with CDK4/6i synergistically induced cell death ex vivo in MC38 murine-derived organotypic tumor spheroids (MDOTS) (28) (FIG. 5B, FIG. 14A). Furthermore, combination treatment of CDK4/6i with PD-1 blockade down-regulated levels of CCL2, CXCL1 and CCL3, which negatively regulate the Th1 response (FIG. 5C). However, when MDOTS were generated from tumors grown in Rag1$^{-/-}$ immunodeficient mice, which lack both B and T lymphocytes, or when the Th1 response was blocked by addition of an anti-IFNγ neutralizing antibody, we no longer observed synergistic effects of CDK4/6i combined with anti-PD-1 treatment (FIG. 14B, 14C). In contrast, addition of a neutralizing antibody against CCL5 has no such rescue effect (FIG. 14C), suggesting that the T cells are the key cellular mediators of the anti-tumor activity of CDK4/6i.

Figure 6A:
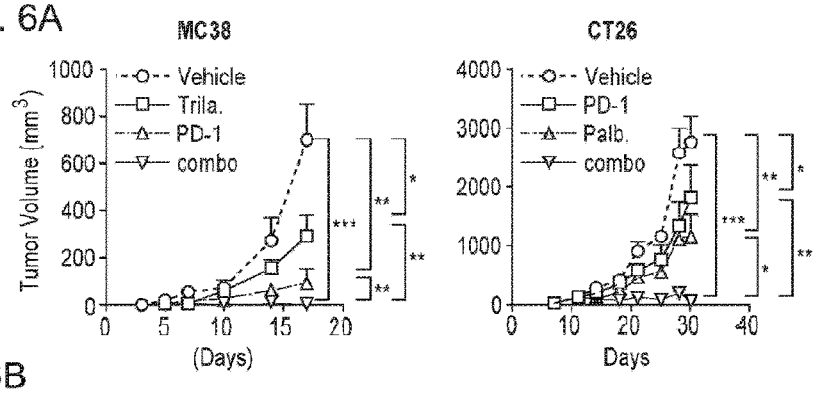
FIG. 6. Combination treatment of CDK4/6 inhibitor synergize anti-PD-1 antibody induced anti-tumor immunity through T cell. A. Tumor growth curves of MC38 (left) or CT26 (right) treated with CDK4/6 inhibitor or PD-1 antibody alone or in combination. MC38 murine cancer cells were injected subcutaneously into C57BL/6 mice. The mice were treated with either CDK4/6 inhibitor (trilaciclib or palbociclib, 100 mg/kg) intermittently (3 days on, 4 days off) with or without PD-1 antibody (200 µg/mouse, 3 times a week) as indicated starting from day 3 (MC38) or day 7 (CT26). Tumor volumes were monitored every 2 to 3 days. Each graph shows representative results from two independent experiments. (left panel, n=8; right panel, n=10) (*p<0.05, p<0.01, *p<0.001) B. Individual traces of tumor volume of CT26 tumors over time after treatment with palbociclib and anti-PD-1, either alone or in combination (n=8). C. Quantification of cytokine production produced by MC38 tumor infiltrating T lymphocytes. At the end of the treatment (day 17), mice were sacrificed and TILs were isolated from the tumor for cytokine analysis for IL-2 from CD4+ T cells (left panel) and IFNγ from CD8+ T cells (right panel). (*p<0.05, p<0.01, *p<0.001) D. Cytokine production of IFNγ from CD8+ T cells from inguinal lymph nodes of mice with MC38 tumors treated with trilaciclib at the end of treatment (day 17). E. Tumor growth curves of CT26 treated with palbociclib (100 mg/kg) and PD-1 antibody (200 μg/mouse) with or without anti-CD4 (400 μg/mouse) or anti-CD8 (400 μg/mouse) depletion antibodies. The depletion antibody treatment started at day −3 before tumor implantation was continued twice a week. Palbociclib and PD-1 were dosed at the same schedule shown in panel (D) starting from day 7. The graph shows representative result of two independent experiments, and different people performed the dosing and tumor measurement. (n=10) (*p<0.001, **p<0.0001).
Figure 6B:
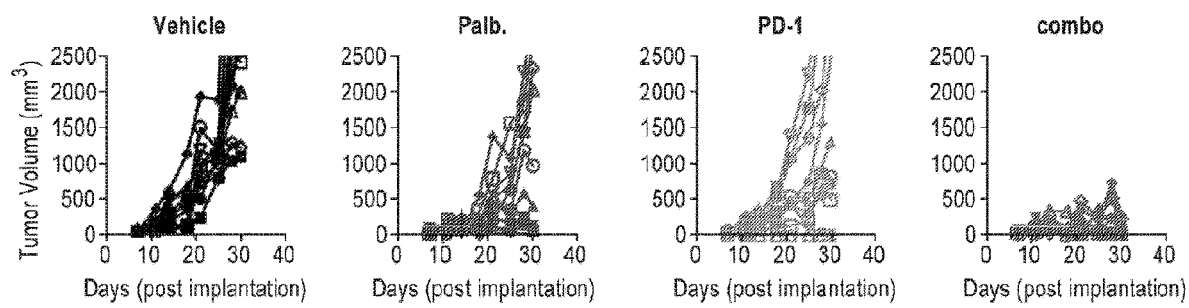

Example 6: T Cells are Required for Anti-Tumor Immunity Induced by Combinational Treatment of CDK4/6 Inhibitor and Anti-PD-1 Antibody As previously reported, in vivo PD-1 blockade induced partial tumor growth inhibition in the MC38 model (46); however, consistent with the results in MDOTS, the addition of intermittent exposure to trilaciclib nearly eliminated tumor growth (FIG. 6A, left panel). Furthermore, we found that treatment with palbociclib in combination with PD-1 blockade had a similar effect in mice bearing tumors derived from CT26 colon carcinoma cells (47), which are far less responsive to PD-1 blockade alone (FIG. 6A, right panel, FIG. 6B).

Figure 6C:
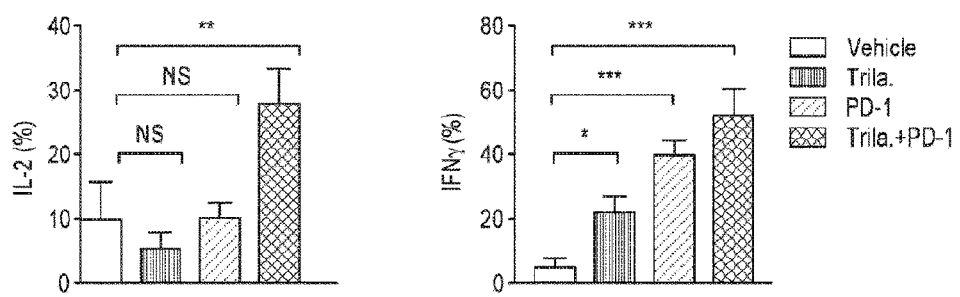
Figure 6D:
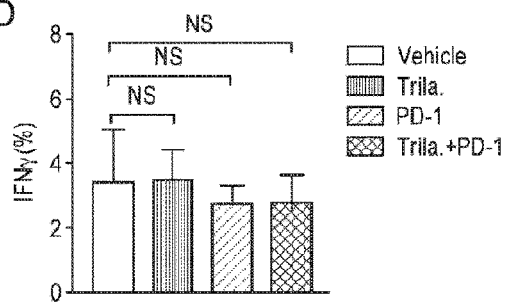
Figure 6E:
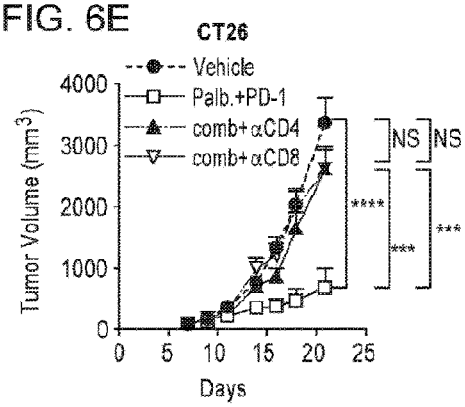
Figure 15A:
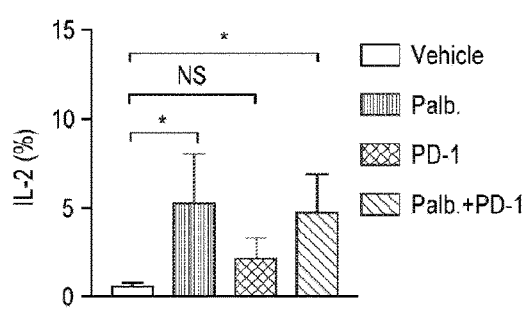
FIG. 15. Combination treatment of CDK4/6 inhibitor and anti-PD-1 antibody on established tumor. A. Quantification of IL-2 production produced by CT26 tumor infiltrating CD4+ T lymphocytes 2 days after the last treatment (day 32), (*p<0.05, p<0.01, *p<0.001). B. Cytokine production from inguinal lymph nodes of mice with MC38 tumors treated with trilaciclib. At the end of the treatment (day 17), mice were sacrificed and inguinal lymph nodes were isolated for cytokine analysis for IL-2 from $CD4^+$. C. Survival curve of MC38 murine cancer cells were injected subcutaneously into C57BL/6 mice. The mice were treated with either CDK4/6 inhibitor (Palbociclib, 100 mg/kg) intermittently (3 days on, 4 days off) with or without PD-1 antibody (200 μg/mouse, 3 times a week) starting from day 7. Mice were sacrificed when the tumor volume is above 2500 mm³ or the animal has reached protocol study endpoint. D. Individual tumor volume change of each mouse from each treatment group from panel (C).
Figure 15B:
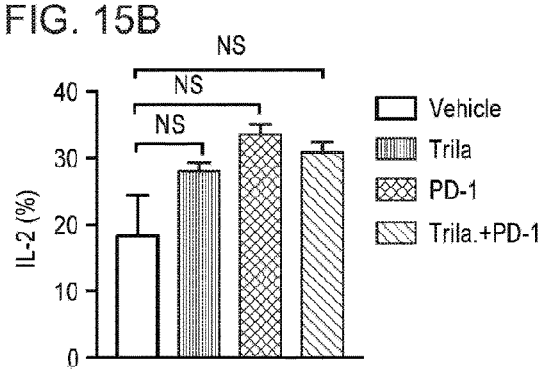
Figure 15C:
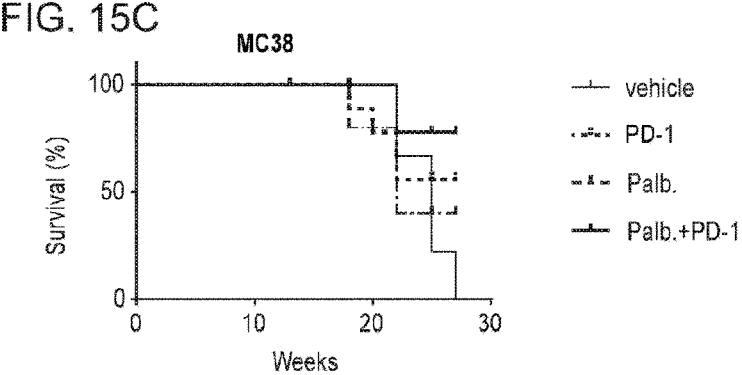
Figure 15D:
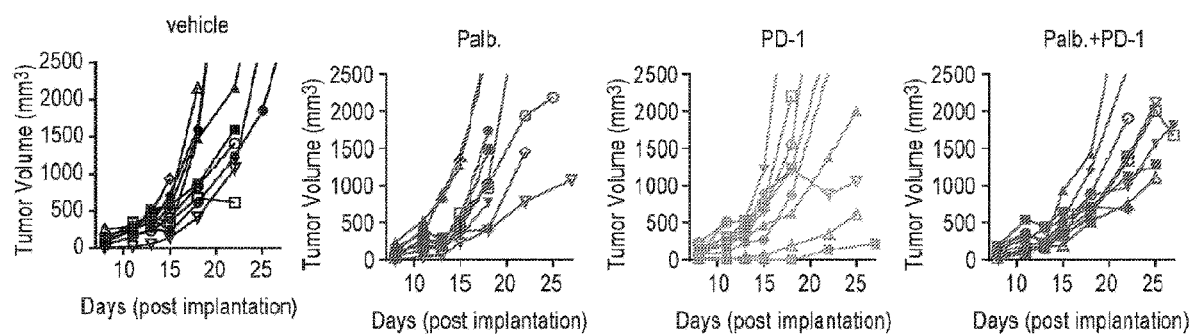
Figure 16:
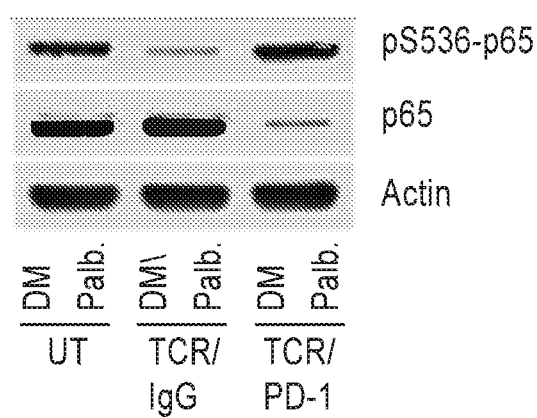
FIG. 16. Effect of TCR stimulation and CDK4/6 inhibition on phosphorylation of NFkB. Immunoblot for phospho-s536-p65 and total p65 from lysates from PD-1-Jurkat cells treated as indicated for 18 h.

Profiling of TILs from MC38 tumors revealed that anti-PD-1 alone increased CD8+ IFNγ production but not CD4+ IL-2 production (FIG. 6C). Thus, in this model, PD-1 blockade increased the cytotoxicity of CD8+ T cells, but did not increase T cell proliferation through IL-2. Addition of trilaciclib to PD-1 blockade resulted in ~10-fold increase in levels of IFNγ in CD8+ TILs and ~2-fold increase in CD4+ IL-2 production (FIG. 6C). The increase in IL-2 was also observed in the CT26 model treated with palbociclib alone or in combination with PD-1 (FIG. 15A). Of note, in the MC38 model, IL-2 production was also increased in the murine inguinal lymph nodes (FIG. 15B), albeit to a lesser extent compared to TILs, while IFNγ levels remained unchanged (FIG. 6D). Importantly, we found that depletion of either CD4$^+$ or CD8$^+$ T cells in the CT26 model reversed the anti-tumor effect induced by combined treatment of palbociclib and anti-PD-1 (FIG. 6E). As T cell depletion completely ablated the anti-tumor activity of the combination treatment, the predominant anti-tumor activity of palbociclib in this model could not be independent of T cells (i.e. a direct anti-proliferative effect on tumor cells due to tumor cell CDK4/6 inhibition). Instead, our results demonstrate that palbociclib amplifies the T cell dependent antitumor effects of PD-1 blockade. Finally, combination treatment of CDK4/6i and PD-1 blockade was superior to single agents alone in treating established tumors, although eventual relapse was evident in all treatment groups (FIG. 15C, 15D). Thus, CDK4/6 inhibitors greatly potentiate the effects of PD-1 blockade in vivo, and the major factors of the CDK4/6i-induced anti-tumor immune response are T cells.

REFERENCES

1. Borghaei H, Paz-Ares L, Horn L, Spigel D R, Steins M, Ready N E, et al. Nivolumab versus Docetaxel in Advanced Nonsquamous Non-Small-Cell Lung Cancer. The New England journal of medicine 2015; 373:1627-39.
2. Robert C, Schachter J, Long G V, Arance A, Grob J J, Mortier L, et al. Pembrolizumab versus Ipilimumab in Advanced Melanoma. The New England journal of medicine 2015; 372:2521-32.
3. Rizvi N A, Hellmann M D, Snyder A, Kvistborg P, Makarov V, Havel J J, et al. Cancer immunology. Mutational landscape determines sensitivity to PD-1 blockade in non-small cell lung cancer. Science 2015; 348:124-8.
4. Pardoll D M. The blockade of immune checkpoints in cancer immunotherapy. Nature reviews Cancer 2012; 12:252-64.
5. Leach D R, Krummel M F, Allison J P. Enhancement of antitumor immunity by CTLA-4blockade. Science 1996; 271:1734-6.
6. Phan G Q, Yang J C, Sherry R M, Hwu P, Topalian S L, Schwartzentruber D J, et al. Cancer regression and autoimmunity induced by cytotoxic T lymphocyte-associated antigen 4 blockade in patients with metastatic melanoma. Proceedings of the National Academy of Sciences of the United States of America 2003; 100:8372-7.
7. Nishimura H, Nose M, Hiai H, Minato N, Honjo T. Development of lupus like autoimmune diseases by disruption of the PD-1 gene encoding an ITIM motif-carrying immunoreceptor. Immunity 1999; 11:141-51.
8. Dong H, Strome S E, Salomao D R, Tamura H, Hirano F, Flies D B, et al. Tumor associated B7-H1 promotes T-cell apoptosis: a potential mechanism of immune evasion. Nature medicine 2002; 8:793-800.
9. Brahmer J R, Drake C G, Wollner I, Powderly J D, Picus J, Sharfman W H, et al. Phase I study of single-agent anti-programmed death-1 (MDX-1106) in refractory solid tumors: safety, clinical activity, pharmacodynamics, and immunologic correlates. Journal of clinical oncology: official journal of the American Society of Clinical Oncology 2010; 28:3167-75.
10. Sharma P, Allison J P. Immune checkpoint targeting in cancer therapy: toward combination strategies with curative potential. Cell 2015; 161:205-14.
11. Mahoney K M, Rennert P D, Freeman G J. Combination cancer immunotherapy and new immunomodulatory targets. Nature reviews Drug discovery 2015; 14:561-84.
12. Kaluza K M, Thompson J M, Kottke T J, Flynn Gilmer H C, Knutson D L, Vile R G. Adoptive T cell therapy promotes the emergence of genomically altered tumor escape variants. International journal of cancer Journal international du cancer 2012; 131:844-54.
13. Kelderman S, Schumacher T N, Haanen J B. Acquired and intrinsic resistance in cancer immunotherapy. Molecular oncology 2014; 8:1132-9.
14. Koyama S, Akbay E A, Li Y Y, Herter-Sprie G S, Buczkowski K A, Richards W G, et al. Adaptive resistance to therapeutic PD-1 blockade is associated with upregulation of alternative immune checkpoints. Nature communications 2016; 7:10501.
15. Adams J L, Smothers J, Srinivasan R, Hoos A. Big opportunities for small molecules in immuno-oncology. Nature reviews Drug discovery 2015; 14:603-22.
16. Sullivan R J, Lorusso P M, Flaherty K T. The intersection of immune-directed and molecularly targeted therapy in advanced melanoma: where we have been, are, and will be. Clinical cancer research: an official journal of the American Association for Cancer Research 2013; 19:5283-91.
17. Akbay E A, Koyama S, Carretero J, Altabef A, Tchaicha R I, Christensen C L, et al. Activation of the PD-1 pathway contributes to immune escape in EGFR-driven lung tumors. Cancer discovery 2013; 3:1355-63.
18. Ebert P J, Cheung J, Yang Y, McNamara E, Hong R, Moskalenko M, et al. MAP Kinase Inhibition Promotes T Cell and Anti-tumor Activity in Combination with PD-L1 Checkpoint Blockade. Immunity 2016; 44:609-21.
19. Wells A D, Morawski P A. New roles for cyclin-dependent kinases in T cell biology: linking cell division and differentiation. Nature reviews Immunology 2014; 14:261-70.
20. Scheicher R, Hoelbl-Kovacic A, Bellutti F, Tigan A S, Prchal-Murphy M, Heller G, et al. CDK6 as a key regulator of hematopoietic and leukemic stem cell activation. Blood 2015; 125:90-101.
21. Min I M, Pietramaggiori G, Kim F S, Passegue E, Stevenson K E, Wagers A J. The transcription factor EGR1 controls both the proliferation and localization of hematopoietic stem cells. Cell stem cell 2008; 2:380-91.
22. Macian F. NFAT proteins: key regulators of T-cell development and function. Nature reviews Immunology 2005; 5:472-84.
23. Quigley M, Pereyra F, Nilsson B, Porichis F, Fonseca C, Eichbaum Q, et al. Transcriptional analysis of HIV-specific CD8+ T cells shows that PD-1 inhibits T cell function by upregulating BATF. Nature medicine 2010; 16:1147-51.
24. Garcia C A, Benakanakere M R, Alard P, Kosiewicz M M, Kinane D F, Martin M. Antigenic experience dictates functional role of glycogen synthase kinase-3 in human CD4+ T cell responses. Journal of immunology 2008; 181:8363-71.
25. Ohteki T, Parsons M, Zakarian A, Jones R G, Nguyen L T, Woodgett J R, et al. Negative regulation of T cell proliferation and interleukin 2 production by the serine threonine kinase GSK-3. The Journal of experimental medicine 2000; 192:99-104.
26. Bisi J E, Sorrentino J A, Roberts P J, Tavares F X, Strum J C. Preclinical Characterization of G1T28: A Novel CDK4/6 Inhibitor for Reduction of Chemotherapy-Induced Myelosuppression. Molecular cancer therapeutics 2016; 15:783-93.
27. He S, Roberts P J, Sorrentino J A, Bisi J E, Storrie-White H, Tiessen R G, et al. Transient CDK4/6 inhibition protects hematopoietic stem cells from chemotherapy-induced exhaustion. Science translational medicine 2017; 9.
28. Jenkins R W, Aref A R, Lizotte P H, Paweletz C P, Zhou C W, Bowden M, et al. Ex Vivo Profiling of PD-1 Blockade Using Organotypic Tumor Spheroids. Manuscript unpublished.
29. Veinotte L, Gebremeskel S, Johnston B. CXCL16-positive dendritic cells enhance invariant natural killer T 29. cell-dependent IFN-gamma production and tumor control. Oncoimmunology 2016; 5:e1160979.
30. Peng D, Kryczek I, Nagarsheth N, Zhao L, Wei S, Wang W, et al. Epigenetic silencing of TH1-type chemokines shapes tumour immunity and immunotherapy. Nature 2015; 527:249-53.
31. Anders L, Ke N, Hydbring P, Choi Y J, Widlund H R, Chick J M, et al. A systematic screen for CDK4/6 substrates links FOXM1 phosphorylation to senescence suppression in cancer cells. Cancer cell 2011; 20:620-34.
32. Bienkiewicz E A, Lumb K J. Random-coil chemical shifts of phosphorylated amino acids. Journal of biomolecular NMR 1999; 15:203-6.
33. Tholey A, Lindemann A, Kinzel V, Reed J. Direct effects of phosphorylation on the preferred backbone conformation of peptides: a nuclear magnetic resonance study. Biophysical journal 1999; 76:76-87.
34. Porter C M, Havens M A, Clipstone N A. Identification of amino acid residues and protein kinases involved in the regulation of NFATc subcellular localization. The Journal of biological chemistry 2000; 275:3543-51.
35. Macian F, Garcia-Rodriguez C, Rao A. Gene expression elicited by NFAT in the presence or absence of cooperative recruitment of Fos and Jun. The EMBO journal 2000; 19:4783-95.
36. Chen Z, Cheng K, Walton Z, Wang Y, Ebi H, Shimamura T, et al. A murine lung cancer co-clinical trial identifies genetic modifiers of therapeutic response. Nature 2012; 483:613-7.
37. Asghar U, Witkiewicz A K, Turner N C, Knudsen E S. The history and future of targeting cyclin-dependent kinases in cancer therapy. Nature reviews Drug discovery 2015; 14:130-46.
38. Chang J T, Ciocca M L, Kinjyo I, Palanivel V R, McClurkin C E, Dejong C S, et al. Asymmetric proteasome segregation as a mechanism for unequal partitioning of the transcription factor T-bet during T lymphocyte division. Immunity 2011; 34:492-504.
39. Denkert C, Loibl S, Noske A, Roller M, Muller B M, Komor M, et al. Tumor-associated lymphocytes as an independent predictor of response to neoadjuvant chemotherapy in breast cancer. Journal of clinical oncology: official journal of the American Society of Clinical Oncology 2010; 28:105-13.
40. Balkwill F R, Mantovani A. Cancer-related inflammation: common themes and therapeutic opportunities. Seminars in cancer biology 2012; 22:33-40.
41. Grivennikov S, Karin E, Terzic J, Mucida D, Yu G Y, Vallabhapurapu S, et al. IL-6 and Stat3 are required for survival of intestinal epithelial cells and development of colitis-associated cancer. Cancer cell 2009; 15:103-13.
42. Crawford A, Angelosanto J M, Kao C, Doering T A, Odorizzi P M, Barnett B E, et al. Molecular and transcriptional basis of CD4(+) T cell dysfunction during chronic infection. Immunity 2014; 40:289-302.
43. Puyol M, Martin A, Dubus P, Mulero F, Pizcueta P, Khan G, et al. A synthetic lethal interaction between K-Ras oncogenes and Cdk4 unveils a therapeutic strategy for non-small cell lung carcinoma. Cancer cell 2010; 18:63-73.
44. Schumacher T N, Schreiber R D. Neoantigens in cancer immunotherapy. Science 2015; 348:69-74.
45. McFadden D G, Politi K, Bhutkar A, Chen F K, Song X, Pirun M, et al. Mutational landscape of EGFR-, MYC-, and Kras-driven genetically engineered mouse models of lung adenocarcinoma. Proceedings of the National Academy of Sciences of the United States of America 2016.
46. Ngiow S F, Young A, Jacquelot N, Yamazaki T, Enot D, Zitvogel L, et al. A Threshold Level of Intratumor CD8+ T-cell PD1 Expression Dictates Therapeutic Response to Anti-PD1. Cancer research 2015; 75:3800-11.
47. Duraiswamy J, Kaluza K M, Freeman G J, Coukos G. Dual blockade of PD-1 and CTLA-4 combined with tumor vaccine effectively restores T-cell rejection function in tumors. Cancer research 2013; 73:3591-603.
48. De Simone M, Arrigoni A, Rossetti G, Gruarin P, Ranzani V, Politano C, et al. Transcriptional Landscape of Human Tissue Lymphocytes Unveils Uniqueness of Tumor-Infiltrating T Regulatory Cells. Immunity 2016; 45:1135-47.
49. Kollmann K, Heller G, Schneckenleithner C, Warsch W, Scheicher R, Ott R G, et al. A Kinase-Independent Function of CDK6 Links the Cell Cycle to Tumor Angiogenesis. Cancer cell 2016; 30:359-60.
50. Handschick K, Beuerlein K, Jurida L, Bartkuhn M, Muller H, Soelch J, et al. Cyclin-dependent kinase 6 is a chromatin-bound cofactor for NF-kappaB-dependent gene expression. Molecular cell 2014; 53:193-208.
51. Buss H, Handschick K, Jurrmann N, Pekkonen P, Beuerlein K, Muller H, et al. Cyclin-dependent kinase 6 phosphorylates NF-kappaB P65 at serine 536 and contributes to the regulation of inflammatory gene expression. PLoS One 2012; 7:e51847.
52. Martinez G J, Pereira R M, Aijo T, Kim E Y, Marangoni F, Pipkin M E, et al. The transcription factor NFAT promotes exhaustion of activated CD8 (+) T cells. Immunity 2015; 42:265-78.
53. Infante J R, Cassier P A, Gerecitano J F, Witteveen P O, Chugh R, Ribrag V, et al. A Phase I Study of the Cyclin-Dependent Kinase 4/6 Inhibitor Ribociclib (LEE011) in Patients with Advanced Solid Tumors and Lymphomas. Clin. Cancer Res. 2016; 22:5696 705.
54. Cadoo K A, Gucalp A, Traina T A. Palbociclib: an evidence-based review of its potential in the treatment of breast cancer. Breast Cancer (Dove Med Press) 2014; 6:123-33.
55. Fabian M A, Biggs W H, 3rd, Treiber D K, Atteridge C E, Azimioara M D, Benedetti M G, et al. A small molecule-kinase interaction map for clinical kinase inhibitors. Nature biotechnology 2005; 23:329-36.
56. Dobin A, Davis C A, Schlesinger F, Drenkow J, Zaleski C, Jha S, et al. STAR: ultrafast universal RNA-seq aligner. Bioinformatics 2013; 29:15-21.
57. Bray N L, Pimentel H, Melsted P, Pachter L. Near-optimal probabilistic RNA-seq quantification. Nature biotechnology 2016; 34:525-7.
58. Soneson C, Love M I, Robinson M D. Differential analyses for RNA-seq: transcript-level estimates improve gene-level inferences. F1000Research 2015; 4:1521.
59. Risso D, Ngai J, Speed T P, Dudoit S. Normalization of RNA-seq data using factor analysis of control genes or samples. Nature biotechnology 2014; 32:896-902.
60. Scialdone A, Natarajan K N, Saraiva L R, Proserpio V, Teichmann S A, Stegle O, et al. Computational assignment of cell-cycle stage from single-cell transcriptome data. Methods 2015; 85:54-61.
61. Jung, H. & Miller, R. J. Activation of the nuclear factor of activated T-cells (NFAT) mediates upregulation of CCR2 chemokine receptors in dorsal root ganglion (DRG) neurons: a possible mechanism for activity-dependent transcription in DRG neurons in association with neuropathic pain. Mol. Cell Neurosci. 37, 170-177, doi: 10.1016/j.mcn.2007.09.004 (2008).

62. Zhou, B. et al. Characterization of Nfatc1 regulation identifies an enhancer required for gene expression that is specific to pro-valve endocardial cells in the developing heart. Development 132, 1137-1146, doi:10.1242/dev.01640 (2005).
63. Yu, H. B. et al. NFATc2 mediates epigenetic modification of dendritic cell cytokine and chemokine responses to dectin-1 stimulation. Nucleic Acids Res. 43, 836-847, doi:10.1093/nar/gku1369 (2015).
64. Blomberg, K. E. et al. Transcriptional signatures of Itk-deficient CD3+, CD4+ and CD8+ T cells. BMC Genomics 10, 233, doi: 10.1186/1471-2164-10-233 (2009).
65. Berglund, L. M. et al. NFAT regulates the expression of AIF-1 and IRT-1: yin and yang splice variants of neointima formation and atherosclerosis. Cardiovasc. Res. 93, 414-423, doi:10.1093/cvr/cvr309 (2012).
66. Kim, H. P. & Leonard, W. J. The basis for TCR-mediated regulation of the IL-2 receptor alpha chain gene: role of widely separated regulatory elements. EMBO J. 21, 3051-3059, doi:10.1093/emboj/cdf321 (2002).
6.7 Karpurapu, M. et al. Cyclin D1 is a bona fide target gene of NFATc1 and is sufficient in the mediation of injury-induced vascular wall remodeling. J. Biol. Chem. 285, 3510-3523, doi:10.1074/jbc.M109.063727 (2010).
68. Zhang, S., Luo, L., Wang, Y., Gomez, M. F. & Thorlacius, H. Nuclear factor of activated T cells regulates neutrophil recruitment, systemic inflammation, and T-cell dysfunction in abdominal sepsis. Infect. Immun. 82, 3275-3288, doi:10.1128/IAI.01569-14 (2014).
69. Busch, R. et al. NFATc1 releases BCL6-dependent repression of CCR2 agonist expression in peritoneal macrophages from *Saccharomyces cerevisiae* infected mice. Eur. J. Immunol. 46, 634-646, doi:10.1002/eji.201545925 (2016).
70. Paine, A. et al. IL-2 upregulates CD86 expression on human CD4 (+) and CD8(+) T cells. J. Immunol. 188, 1620-1629, doi:10.4049/jimmunol.1100181 (2012).
71. Mognol, G. P., Carneiro, F. R., Robbs, B. K., Faget, D. V. & Viola, J. P. Cell cycle and apoptosis regulation by NFAT transcription factors: new roles for an old player. Cell Death Dis. 7, e2199, doi:10.1038/cddis.2016.97 (2016).
72. Bhattacharyya, S. et al. NFATc1 affects mouse splenic B cell function by controlling the calcineurin—NFAT signaling network. J. Exp. Med 0.208, 823-839, doi:10.1084/jem.20100945 (2011).

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a tumor in a subject comprising administering to said subject a CDK4/6 inhibitor and an immune checkpoint inhibitor, wherein the CDK4/6 inhibitor is palbociclib, and wherein the immune checkpoint inhibitor is an anti-PD-1 antibody, wherein the anti-PD-1 antibody is administered 3 times a week, wherein the CDK4/6 inhibitor is administered for 2 or 3 days prior to administration of the checkpoint inhibitor, and wherein the CDK4/6 inhibitor is administered for 3 days on followed by 4 days off, wherein the tumor is a colorectal tumor.

2. The method of claim 1, wherein treating the tumor comprises decreasing tumor burden in a subject.

3. The method of claim 1, wherein treating the tumor comprises increasing T-cell infiltration of the tumor.

4. The method of claim 1, wherein the CDK4/6 inhibitor is administered to the subject in an amount sufficient to increase T-cell activation.

5. The method of claim 1, wherein the CDK4/6 inhibitor is administered in an amount sufficient to increase IL-2 and/or IFN-γ production in a tumor infiltrating lymphocyte (TIL).

6. The method of claim 5, wherein said TIL is a CD8+ T-cell, a CD4+ T-cell, a T effector cell, a T helper cell or a T regulatory cell.

7. The method of claim 1, wherein the CDK4/6 inhibitor is administered in an amount sufficient to increase CXCL-9 and/or CXCL-10 production.

* * * * *